(12) United States Patent
Dreyfus

(10) Patent No.: US 7,928,216 B2
(45) Date of Patent: Apr. 19, 2011

(54) NUCLEASE RESISTANT EXTERNAL GUIDE SEQUENCES FOR TREATING INFLAMMATORY AND VIRAL RELATED RESPIRATORY DISEASES

(75) Inventor: David H. Dreyfus, New Haven, CT (US)

(73) Assignee: Yale University, New Haven, CT (US)

( * ) Notice: Subject to any disclaimer, the term of this patent is extended or adjusted under 35 U.S.C. 154(b) by 380 days.

(21) Appl. No.: 11/118,875

(22) Filed: Apr. 29, 2005

(65) Prior Publication Data

US 2005/0277613 A1 Dec. 15, 2005

Related U.S. Application Data

(60) Provisional application No. 60/566,968, filed on Apr. 29, 2004.

(51) Int. Cl.
*C07H 21/04* (2006.01)
*A61K 31/715* (2006.01)

(52) U.S. Cl. .......................................... 536/24.5; 514/44

(58) Field of Classification Search ........................ None
See application file for complete search history.

(56) References Cited

U.S. PATENT DOCUMENTS

| 5,624,824 | A | 4/1997 | Yuan et al. ................... 435/91.2 |
| 5,728,521 | A | 3/1998 | Yuan et al. ........................ 435/6 |
| 5,869,248 | A | 2/1999 | Yuan et al. ........................ 435/6 |
| 6,057,153 | A * | 5/2000 | George et al. ............... 435/320.1 |
| 6,610,478 | B1 | 8/2003 | Takle et al. ........................ 435/6 |
| 6,822,087 | B1 * | 11/2004 | Renzi ........................... 536/24.5 |
| 2003/0211583 | A1 | 11/2003 | Stein ............................ 435/91.2 |
| 2004/0175384 | A1 * | 9/2004 | Mohapatra et al. ........ 424/146.1 |

FOREIGN PATENT DOCUMENTS

| WO | WO 93/01286 | 1/1993 |
| WO | WO 93/22434 | 11/1993 |
| WO | WO 95/24489 | 9/1995 |
| WO | WO96/21731 | 7/1996 |
| WO | WO 99/66037 | 12/1999 |
| WO | WO 02/46417 | 6/2002 |

OTHER PUBLICATIONS

Kristoffersen et al. (1994) Arch. Virol. 138:85-93.*
Ennaciri et al. (2007) J. Leukocyte Biology 81:625-631.*
Agrawal et al., "Oligodeoxynucleoside phosphoramidates and phosphorothioates as inhibitors of human immunodeficiency virus", *Proc. Natl. Acad. Sci. USA*, 85: 7079-7083 (1988).
Anderson, et al., "Effect of cystic fibrosis on inhaled aerosol boluses", *Am. Rev. Respir. Dis.*, 140: 1317-1324 (1989).
Arava et al., "Specific gene expression in pancreatic beta-cells: cloning and characterization of differentially expressed genes", *Diabetes*, 48(3):552-556 (1999).
Aronica, et al., "Susceptibility to allergic lung disease regulated by recall responses of dual-receptor memory T cells", *J. Allergy Clin. Immunol.*, 114(6):1441-1448 (2004).
Blackburn, et al., "Adenosine mediates IL-13-induced inflammation and remodeling in the lung and interacts in an IL-13-adenosine amplification pathway", *J. Clin. Invest.*, 112(3):332-344 (2003).
Borish, et al., "Efficacy of soluble IL-4 receptor for the treatment of adults with asthma", *J. Allergy Clin.Immunol.*, 107(6):963-70 (2001).
Brown, et al., "Serologic Evidence of Prenatal Influenza in the Etiology of Schizophrenia", *Arch. Gen. Psychiatry*, 61(8):774-780 (2004).
Bueving, et al., "Influenza vaccination in children with asthma: randomized double-blind placebo-controlled trial", *Am. J. Respir. Crit. Care Med.*, 169(4):488-493 (2003).
Christy, et al., "Effectiveness of influenza vaccine for the prevention of asthma exacerbations", *Arch. Dis. Child*, 89(8):734-735 (2004).
Chu and Paul, "Expressed genes in interleukin-4 treated B cells identified by cDNA representational difference analysis", *Mol Immunol*, 35:487-502 (1998).
Cohn, et al., "Asthma: mechanisms of disease persistence and progression", *Annu. Rev. Immunol.*, 22:789-815 (2004).
Dahl, et al., "Viral-induced T helper type 1 responses enhance allergic disease by effects on lung dendritic cells", *Nat. Immunol.*, 5(3):337-343 (2004).
De Longueville, "What are the candidate groups for pharmacotherapeutic intervention to prevent asthma?", *Pediatr. Allergy Immunol.*, 11(Suppl. 13):41-44 (2000).
Dent, et al., "T helper type 2 inflammatory disease in the absence of interleukin 4 and transcription factor STAT6", *Proc Natl Acad Sci U S A*, 95:13823-13828 (1998).
Desmet, et al., "Selective blockade of NF-kappa B activity in airway immune cells inhibits the effector phase of experimental asthma", *J. Immunol.*, 173(9):5766-5775 (2004). Dreyfus, et al., "An RNA external guide sequence ribozyme targeting human interleukin-4 receptor alpha mRNA", *Int. Immunopharmacol.*, 4(8):1015-1027 (2004).
Elias, "The relationship between asthma anc COPD. Lessons from transgenic mice", *Chest*, 126(2Suppl.):111S.-116S (2004).
Essner, et al., "Functional interleukin-4 receptor and interleukin-2 receptor common gamma chain in human gastric carcinoma: a possible mechanism for cytokine-based therapy", *J. Gastrointest. Surg.*, 5:81-90 (2001).
ETAC Study Group, "Allergic factors associated with the development of asthma and the influence of cetitizine in a double-blind, randomised, placebo-controlled trial: First results of ETAC(R)", *Pediatr. Allergy Immunol.*, 9(3):116-124 (1998).

(Continued)

*Primary Examiner* — Richard Schnizer
(74) *Attorney, Agent, or Firm* — Ivor R. Elrifi, Esq.; Mintz Levin Cohn Ferris Glovsky and Popeo P.C.

(57) ABSTRACT

External Guide Sequence (EGS) are described that target proteins required for generation and modification of the immunoglobulin and T-cell repertoire that are useful for treatment or prevention of inflammatory or related diseases. Formulations suitable for administration of an EGS for treatment of inflammatory or related disease are described. The formulations may be administered via inhalation, injection, or orally. The formulations may be in the form of an ointment, lotion, cream, gel, drop, suppository, spray, liquid, powder, granule, solution, suspension, capsule, or tablet. Methods of treating inflammatory or related diseases by administering an effective amount of an EGS in a pharmaceutically acceptable carrier are also described. In preferred embodiments, the disease is asthma, allergic rhinitis, food allergies, atopic skin disease such as eczema, IL-4 and/or IL-13 dependent malignancies, IL-4 and/or IL-13 dependent autoimmune diseases, atopic diseases, the flu, and diseases caused by IL-4 dependent replication of viruses.

5 Claims, 5 Drawing Sheets

OTHER PUBLICATIONS

Finotto, et al., Treatment of allergic airway inflammation and hyper-responsiveness by antisense-induced local blockade of GATA-3 expression, *J. Exp. Med.*, 193:1247-1260 (2001).

Frippiat, et al., "The recombination-activating gene 1 of Pleurodeles waltl (urodele amphibian) is transcribed in lymphoid tissues and in the central nervous system", *Immunogenetics*, 52(3-4):264-275 (2001).

Galizzi, et al., "Molecular cloning of a cDNA encoding the human interleukin 4 receptor", *Int. Immunol.*, 2(7):669-675 (1990).

Ge, et al., "Inhibition of influenza virus production in virus-infected mice by RNA interference", *Proc. Natl. Acad. Sci. USA*, 101(23):8676-8681 (2004).

Georas, et al., "Stat6 inhibits human interleukin-4 promoter activity in T cells", *Blood*, 92:4529-4538 (1998).

Gessner and Rollinghoff, "Biologic functions and signaling of the interleukin-4 receptor complexes", *Immunobiology*, 201(3-4):285-307 (2000).

Gopalan, et al., "RNase P: variations and uses", *J Biol Chem*, 277:6759-62 (2002).

Gorman, "Does parental exposure to influenza raise the risk of schizophrenia?", *Time*, 164(7):80 (2004).

Graber, et al., "The distribution of IL-13 receptor alpha1 expression on B cells, T cells and monocytes and its regulation by IL-13 and IL-4", *Eur. J. Immuno.*, 28:4286-4298 (1998).

Grossman and Paul, "Autoreactivity, dynamic tuning and selectivity", *Curr. Opin. Immunol.*, 13:687-698 (2001).

Grunewald, et al., Upon prolonged allergen exposure IL-4 and IL-4Ralpha knockout mice produce specific IgE leading to anaphylaxis, *Int Arch Allergy Immunol*, 125:322-8 (2001).

Grunig, "IL-13 and adenosine: partners in a molecular dance?", *J. Clin.Invest.*, 112(3):329-31 (2003).

Guerrier-Takada, et al., "Inactivation of gene expression using ribonuclease P and external guide sequences", *Methods Enzymol*, 313:442-56 (2000).

Hackstein, et al., "A novel polymorphism in the 5' promoter region of the human interleukin-4 receptor alpha-chain gene is associated with decreased soluble interleukin-4 receptor protein levels", *Immunogenetics*, 53:264-269 (2001).

Hall, Interleukin-4 receptor alpha gene variants and allergic disease, *Respir. Res.*, 1:6-8 (2000).

Hansen and Kaattari, "The recombination activation gene 1 (RAG1) of rainbow trout (*Oncorhynchus mykiss*): cloning, expression, and phylogenetic analysis", *Immunogenetics*, 42(3):188-195 (1995).

Heasman, "Morpholino oligos: making sense of antisense?", *Dev. Biol.*, 243(2):209-214 (2002).

Heidenreich and Eckstein, "Hammerhead ribozyme-mediated cleavage of the long terminal repeat RNA of human immunodeficiency virus type 1", *J. Biol. Chem.* 267:1904-1909 (1992).

Herrick, et al., "Th2 responses induced by epicutaneous or inhalational protein exposure are differentially dependent on IL-4", *J. Clin. Invest.*, 105:765-775 (2000).

Hershey, et al., "The association of atopy with a gain-of-function mutation in the alpha subunit of the interleukin-4 receptor", *N. Engl. J. Med.*, 337:1720-1725(1997).

Hilton, et al., "Cloning and characterization of a binding subunit of the interleukin 13 receptor that is also a component of the interleukin 4 receptor", *Proc. Natl. Acad. Sci. USA*, 93(1):497-501 (1996).

Howard, et al., "Gene-gene interaction in asthma: IL4RA and IL13 in a Dutch population with asthma", *Am. J. Hum. Genet.*, 70:230-236 (2002).

Kalliomaki, et al., "Probiotics in primary prevention of atopic disease: a randomised placebo-controlled trial", *Lancet*, 357:1076-1079 (2001).

Karp and Wills-Karp, "Complement and IL-12: yin and yang", *Microbes Infect.*, 3:109-119 (2001).

Kash, et al., "Global host immune response: pathognesis and transcriptional profiling of type A influenza viruses expressing the hemagglutinin and neuraminidase genes from the 1918 pandemic virus", *J. Virol.*, 78(17):9499-9511 (2004).

Keegan, et al., "Similarities and differences in signal transduction by interleukin 4 and interleukin 13: analysis of Janus kinase activation", *Proc. Natl. Acad. Sci. USA*, 92:7681-7685 (1995).

Kelly-Welch, et al., "Transgenic expression of insulin receptor substrate 2 in murine B cells alters the cell density-dependence of IgE production in vitro and enhances IgE production in-vivo", *J. Immunol.*, 172(7):4545-4555 (2004).

Klein, et al., "Interleukin-4 and interleukin-4 receptor gene polymorphisms in inflammatory bowel diseases", *Genes Immun.*, 2:287-289 (2001).

Kuperman, et al., "Direct effects of interleukin-13 on epithelial cells cause airway hyperreactivity and mucus overproduction in asthma", *Nat. Med.*, 8:885-889 (2002).

Lee, et al., "Early growth response gene 1-mediated apoptosis is essential for transforming growth factor beta1-induced pulmonary fibrosis", *J.Exp. Med.*, 200(3):377-89 (2004).

Lee, et al., "Vascular endothelial growth factor (VEGF) induces remodeling and enhances TH2-mediated sensitization and inflammation in the lung", *Nat. Med.*, 10(10):1095-103 (2004).

Ma, et al., "Intracellular mRNA cleavage induced through activation of RNase P by nuclease-resistant external guide sequences", *Nat Biotechnol.*, 18(1):58-61 (2000).

Ma, et al., "Nuclease-resistant external guide sequence-induced cleavage of target RNA by human ribonuclease p", *Antisense Nucleic Acid Drug Dev.*, 8:415-426 (1998).

Martinez, et al., "Asthma and wheezing in the first six years of life. The Group Health Medical Associates", *N. Engl. J. Med.*, 332:133-138 (1995).

Mitsuyasu, et al., "Ile50Val variant of IL4R alpha upregulates IgE synthesis and associates with atopic asthma", *Nat. Genet.* 19:119-120 (1998).

Mohrs, et al., "Differences between IL-4- and IL-4 receptor alpha-deficient mice in chronic leishmaniasis reveal a protective role for IL-13 receptor signaling", *J. Immunol.*, 162:7302-7308 (1999).

Moller, et al., "Pollen immunotherapy reduces the development of asthma in children with seasonal rhinoconjunctivitis (the PAT-study),"*J. Allergy Clin. Immunol.*, 109:251-256 (2002).

Mosley, et al., "The murine interleukin-4 receptor: molecular cloning and characterization of secreted and membrane bound forms", *Cell*, 59(2):335-348 (1989).

Mountford, et al., "Signaling via interleukin-4 receptor alpha chain is required for successful vaccination against schistosomiasis in BALB/c mice", *Infect. Immun.*, 69:228-236 (2001).

Murch, "Toll of allergy reduced by probiotics", *Lancet*, 357:1057-1059 (2001).

Nelms, et al., "The IL-4 receptor: signaling mechanisms and biologic functions", *Annu Rev* Immunol, 17:701-38 (1999).

Nguyen-Van-Tam and Hampson, "The epidemiology and clinical impact of pandemic influenza", *Vaccine*, 21(16):1762-1768 (2003).

Noben-Trauth, et al., "An interleukin 4 (IL-4)-independent pathway for CD4+ T cell IL-4 production is revealed in IL-4 receptor-deficient mice", *Proc Natl Acad Sci U S A*, 94:10838-43 (1997).

Noben-Trauth, et al., "IL-4 secreted from individual naive CD4+ T cells acts in an autocrine manner to induce Th2 differentiation", *Eur J* Immunol, 32:1428-33 (2002).

Nyce and Metzger, "DNA antisense therapy for asthma in an animal model", *Nature*, 385(6618):721-725 (1997).

Olavesen, et al., "Analysis of single-nucleotide polymorphisms in the interleukin-4 receptor gene for association with inflammatory bowel disease", *Immunogentics*, 51:1-7 (2000).

Paolella, et al., "Nuclease resistant ribozymes with high catalytic activity", *EMBO J.*, 11: 1913-1919 (1992).

Park, et al., "Complement activation is critical to airway hyper-responsiveness after acute ozone exposure", *Am. J. Respir. Crit. Care Med.*, 169(6):726-732 (2004).

Patino and Martinez, "Interactions between genes and environment in the development of asthma", *Allergy*, 56:279-286 (2001).

Patton and Platz, "Routes of delivery: case studies. (2) Pulmonary delivery of peptides and proteins for systemic action", *Advanced Drug Delivery Reviews*, 8:179-196 (1992).

Pieken, et al., "Kinetic characterization of ribonuclease-resistant 2'-modified hammerhead ribozymes", *Science*, 253: 314-317 (1991).

Plasterk, "RNA silencing: the genome's immune system", *Science*, 296:1263-1265 (2002).

Plehn-Dujowich, et al., "Effective inhibition of influenza virus production in cultured cells by external guide sequences and ribonuclease P", *Proc Natl Acad Sci U S A*, 95: 7327-32 (1998).

Poynter, et al., "NF-kappa B activation in airways modulates allergic inflammation but not hyperresponsiveness", *J. Immunol.*, 173(11):7003-7009 (2004).

Quelle, et al., "Cloning of murine Stat6 and human Stat6, Stat proteins that are tyrosine phosphorylated in responses to IL-4 and IL-3 but are not required for mitogenesis", *Mol. Cell. Biol.*, 15(6):3336-3343 (1995).

Radu, et al., "A targeted mutation in the IL-4Ralpha gene protects mice against autoimmune diabetes", *Proc Natl Acad Sci U S A*, 97:12700-12704 (2000).

Raj and Liu, "Engineering of RNase P ribozyme for gene-targeting applications", *Gene*, 313:59-69 (2003).

Ralevic and Burnstock, "Receptors for purines and pyrimidines", *Pharmacological Reviews*, 50(3):413-492(1998).

Risma, et al., "V75R576 IL-4 receptor alpha is associated with allergic asthma and enhanced IL-4 receptor function", *J. Immunol.*, 169:1604-1610 (2002).

Rosenwasser, et al., "Genetics of atopy and asthma: the rationale behind promoter-based candidate gene studies (IL-4 and IL-10)", *Am J Respir Crit Care Med*, 156:S152-5 (1997).

Ryzhov, et al., "Adenosine-activated mast cells induce IgE synthesis by B lymphocytes: an A2B-mediated process involving Th2 cytokines IL-4 and IL-13 with implications for asthma", *J. Immunol.*, 172(12):7726-7733 (2004).

Sandrasagra, et al., "Discovery and development of respirable antisense therapeutics for asthma", *Antisense Nucleic acid Drug Dev.*, 12:177-181 (2002).

Sarin, et al., "Inhibition of acquired immunodeficiency syndrome virus by oligodeoxynucleoside methylphosphonates", *Proc. Natl. Acad. Sci. USA*, 85:7448-7794 (1988).

Schatz, et al., "The V(D)J recombination activating gene, RAG-1", *Cell*, 59(6):1035-1048 (1989).

Schwarze and Gelfand, "Respiratory viral infections as promoters of allergic sensitization and asthma in animal models", *Eur. Respir.*, 19(2):341-349 (2002).

Shaw, et al., "Modified deoxyoligonucleotides stable to exonuclease degradation in serum", *Nucleic Acids Res*, 19: 747-750 (1991).

Shimoda, et al., "Lack of IL-4-induced Th2 response and IgE class switching in mice with disrupted Stat6 gene", *Nature*, 380:630-3 (1996).

So, et al., "Corticosteroid inhibits IL-4 signaling through down-regulation of IL-4 receptor and STAT6 activity", *FEBS Lett*, 518(1-3):53-9 (2002).

Solberg, et al., "Genomic characterization of equine interleukin-4 receptor alpha-chain (IL4R)", *Vet. Immunol. Immunopathol.*, 97(3-4):187-194 (2004).

Steinke and Borish, "Th2 cytokines and asthma. Interleukin-4: its role in the pathogenesis of asthma, and targeting it for asthma treatment with interleukin-4 receptor antagonists", *Respir. Res.*, 2:66-70 (2001).

Strome, et al., "Interleukin 4 receptor-directed cytotoxin therapy for human head and neck squamous cell carcinoma in animal models", *Clin. Cancer Res.*, 8:281-286 (2002).

Tan, et al., "Epidemiology of respiratory viruses in patients hospitalized with near-fatal asthma, acute exacerbations of asthma, or chronic obstructive pulmonary disease", *Am. J. Med.*, 115(4):272-277 (2003).

Tansey, "The Challenges in the Development of Metered Dose Inhalation Aerosols Using Ozone-Friendly Propellants", *Spray Technol. Market*, 4: 26-29 (1994).

Taube, et al., "Inhibition of complement activation decreases airway inflammation and hyperresponsiveness", *Am. J. Respir. Crit. Care Med.* 168(11):1333-1341 (2003).

Terabe, et al., "NKT cell-mediated repression of tumor immunosurveillance by IL-13 and the IL-4R-STAT6 pathway", *Nat. Immunol.*, 1:515-520 (2000).

Timsina, et al., "Drug delivery to the respiratory tract using dry powder inhalers", *Int. J. Pharm.*, 101:1-13 (1995).

Tomkinson, et al., "A murine IL-4 receptor antagonist that inhibits IL-4- and IL-13-induced responses prevents antigen-induced airway eosinophilia and airway hyperresponsiveness", *J. Immunol.* 166:5792-5800 (2001).

Tompkins, et al., "Protection against lethal influenza virus challenge by RNA interference in vivo", *Proc. Natl. Acad. Sci. USA*, 1010(23):8682-8686 (2004).

Tsitoura, et al., "Respiratory infection with influenza A virus interferes with the induction of tolerance to aeroallergens", *J. Immunol.*, 165(6):3484-3491 (2000).

Umetsu, "Flu strikes the hygiene hypothesis", *Nat. Med.*, 10(3):232-234 (2004).

Vercelli, et al., "The monocyte/IgE connection: may polymorphisms in the CD14 gene teach us about IgE regulation?", *Int. Arch. Allergy Immunol.*, 124(1-3):20-24 (2001).

Warren and Berton, "Induction of germ-line gamma 1 and epsilon Ig gene expression in murine B cells. IL-4 and the CD40 ligand-CD40 interaction provide distinct but synergistic signals", *J. Immunol.*, 155:5637-5646 (1995).

Wills-Karp, et al., "The germless theory of allergic disease: revisiting the hygiene hypothesis", *Nat. Rev. Immunol.*, 1:69-75 (2001).

Wills-Karp, "The gene encoding interleukin-13: a susceptibility locus for asthma and related traits", *Respir. Res.*, 1:19-23 (2000).

Wills-Karp, et al., "Interleukin-13: central mediator of allergic asthma", *Science*, 282:2258-2261 (1998).

Yu, et al., "Cleavage of highly structured viral RNA molecules by combinatorial libraries of hairpin ribozymes. The most effective ribozymes are not predicted by substrate selection rules", *J. Biol. Chem.*, 273, 23524-23533 (1998).

Zarlenga, et al., "Molecular cloning of the swine IL-4 receptor alpha and IL-13 receptor 1-chains: effects of experimental Toxoplasma gondii, Ascaris suum and Trichuris suis infections on tissue mRNA levels", *Vet. Immunol. Immunopathol.*. 101(3-4):223-34 (2004).

Zarrin, et al., "Cloning and characterization of the human recombination activating gene 1 (RAG1) and RAG2 promoter regions", *J. Immunol.*, 159(9):4382-4394 (1997).

Zhang and Altman, "Inhibition of the expression of the human RNase P protein subunits Rpp21, Rpp25, Rpp29 by external guide sequences (EGSs) and siRNA", *J. Mol. Biol.*, 342:1077-1083 (2004).

Zhou, et al., "Transgenic plant-derived siRNAs can suppress propagation of influenza virus in mammalian cells", *FEBS Letters* 577:345-350 (2004).

Zhou, et al., "Identification of NF-kappa B-regulated genes induced by TNFalpha utilizing expression profiling and RNA interference", *Oncogene*, 22(13):2054-2064 (2003).

Zhu, et al., "Analysis of the major patterns of B cell gene expression changes in response to short-term stimulation with 33 single ligands", *J. Immunol.*, 173(12):7141-7149 (2004).

Zhu, et al., "IL-13-induced chemokine responses in the lung: role of CCR2 in the pathogenesis of IL-13-induced inflammation and remodeling", *J. Immunol.*, 168(6):2953-62 (2002).

Zhu, et al., "Stat6 is necessary and sufficient for IL-4's role in Th2 differentiation and cell expansion", *J. Immunol.*, 166:7276-81 (2001).

Izikawa, et al, "Inhibition of IL-4 receptor upregulation on B cells by antisense oligonucleotide suppresses IL-4-induced human IgE production", *Clinical and Experimental Immunology*, 100(3):383-9 (1995).

\* cited by examiner

Target mRNA

RNAse P cleavage of Target mRNA

FIG. 1C

```
AGA UCA GGA GUUCG AGA CCAGC CUG GU GCC
 |              |              |
140            150            160
UU G CAU CU CCA AUG G GGU GGC UUU G CU C
 |              |              |
170            180            190
                                    EGS1
UGG GCU CCU GUU CCC UG UG AGC UGC CUG GU
 |              |              |
200            210            220

CCU GCU GCA GG UGG CAAGC UCU GGG AA CAU
 EGS2          |              |
              230            240            250

GAA GGU CUU GCA GGA GCC CAC CUG CGU CUC
 |              |              |
260            270            280

CGA CUA CAU GAG CAU CU CUA CU UGC GA GUG
 |              |              |
290            300            310

GAA GAU GAA UGG UCC CAC
 |              |
320            330
```

FIG. 2

EGS501 Primer

5'   T7 promoter                          tRNA sequence
TAATACGACTCACTATAG CTGCAG AGCAAGCAGACTCTAAATC
                   PstI   IL4r'

EGS301 Primer
    5'
    HindIII      AcStem           tRNA sequence
    AAGCTTTAAA AATGGTGGGTGGCGAAGGATTCGAACC
         DraI      IL4r'

NUCLEASE RESISTANT EXTERNAL GUIDE SEQUENCES FOR TREATING INFLAMMATORY AND VIRAL RELATED RESPIRATORY DISEASES

CROSS-REFERENCE TO RELATED APPLICATIONS

This application claims priority to U.S. Provisional Application No. 60/566,968 entitled "Nuclease Resistant External Guide Sequences for Treating Inflammatory and Related Diseases" by David H. Dreyfus, filed Apr. 29, 2004.

STATEMENT REGARDING FEDERALY SPONSORED RESEARCH

The Federal Government has certain rights in the invention disclosed herein by virtue of Grant No. GM19422 from the National Institute of Health to David H. Dreyfus.

FIELD OF THE INVENTION

The present invention generally relates to external guide sequences (EGS) for endogenous RNAses for treating inflammatory and related diseases.

BACKGROUND OF THE INVENTION

Atopic diseases such as asthma, allergic rhinitis, food allergies, anaphylaxis and eczema result from a complex interplay between environmental factors and genetic factors (Vercelli, et al., *Int. Arch. Allergy Immunol.* 124:20-24 (2001) and Patino and Martinez, *Allergy* 56:279-286 (2001)). Infants at risk for asthma and other atopic diseases demonstrate increased expression of Immunoglobulin E (IgE) and increased numbers of peripheral eosinophils (Martinez, et al., *N. Engl. J. Med.* 332:133-138 (1995)), reflecting increased expression of cytokines such as interleukin-4 (IL-4) and 13 (IL-13), denoted TH2 (T Helper 2) cytokines, and relatively decreased expression of cytokines such as interferon g and interleukin-12 (IL-12), denoted TH1 (T Helper 1) cytokines (Wills-Karp, et al., *Nat, Rev. Immunol.* 1:69-75 (2001)).

Influenza virus is increasingly identified as a public health concern capable of overwhelming the existing health care system in the event of a pandemic strain. Pandemic strains are capable of causing mortality and morbidity in healthy immuno-competent adults. A paradigm for emergence of pandemic influenza is the 1918 pandemic that occurred due to emergence of a novel influenza strain of the H1N5 subtype with increased human mortality and morbidity (Kash, et al., *J. Virol.* 78(17):9499-9511 (2004)). Another paradigm is the current outbreak of avian influenza of the H5N1 subtype circulating in Asia that may directly infect humans, also with significantly increased mortality relative to more typical human adapted strains (Nguyen-Van and Hampson, *Vaccine* 21(16):1762-1768 (2003)). Influenza viral pathogenesis is magnified by the viral strategy of rapid mutation, facilitated by a viral genome of multiple segments that can re-assort independently between strains in co-infected cells.

The rapid emergence of different antigenic determinants on viral coat proteins requires yearly adjustments of vaccine targets and insures that there will be years in which conventional vaccines are inadequate. While molecular biology will provide more rapid strategies for vaccine production, an opportunity exists for the development of therapies for those individuals for whom vaccine protection is inadequate either by augmentation of host immune mechanisms or by anti-viral strategies that do not rely on vaccines or host immune response. Concerns regarding emergence of a pandemic strain underscore the lack of an effective therapy for influenza and the limitations of existing vaccine strategies. Vaccines may be of little use in the very young and elderly, or in patients with asthma or other chronic respiratory disease (Christy, et al., *Arch. Dis. Child* 89(8):734-735 (2004); Tan, et al., *Am. J. Med.* 115(4):272-277 (2003); and Bueving, et al., *Am. J. Respir. Crit. Care Med.* 169(4):488-493 (2003)). Unfortunately, these are exactly the patients most at risk of death from influenza infection. Pregnant women are also a subgroup at particular risk of influenza infection since there exists a correlation between infection in the first trimester and brain disorders in the exposed fetus including schizophrenia or other neurological abnormalities that may manifest many years after birth (Brown, et al., *Arch. Gen. Psychiatry* 61(8):774-780 (2004) and Gorman, *Time* 164(7):80 (2004)).

A current paradigm proposes that atopic diseases result from an imbalance in cytokine expression with increased expression of TH2 cytokines and relatively decreased expression of TH1 cytokines imprinted in infancy or early childhood (Patino and Martinez, *Allergy* 56:279-286 (2001)). In support of this paradigm, therapies directed at restoring cytokine balance in early childhood can ameliorate or even prevent atopic disease (Kalliomaki, et al., *Lancet* 357:1076-1079 (2001) and Murch, *Lancet* 357:1057-1059 (2001)). Potent antihistamines or other anti-inflammatory medications given to children at risk for asthma significantly delayed the incidence of subsequent asthma in children with IgE-mediated allergy, apparently by preventing histamine and proallergic cytokine release from degranulation of mast cells (Anoymous, *Pediatr. Allergy Immunol.* 9:116-124 (1998); Moller, et al., *J. Allergy Clin. Immunol.* 109:251-256 (2002); and de Longueville, *Pediatr. Allergy Immunol.* 11(Suppl. 13):41-44 (2000)).

The cellular receptors for IL-4 and IL-13 share a common subunit termed the IL-4 receptor α chain, but differ in subunit shared with the IL-4 receptor α chain (Keegan, et al., *PNAS USA* 92:7681-7685 (1995) and Gessner and Rollinghoff, *Immunobiology* 201:285-307 (2000)). Because of receptor sharing, IL-4 and IL-13 share some common effects on target cells including promotion of IgE synthesis and eosinophil survival, but also different effects upon other target cells. For example, IL-4 receptors but not IL-13 receptors are readily detected on the surface of T lymphocytes although IL-13 receptors may nonetheless be expressed intra-cellularly (Graber, et al., *Eur. J. Immuno.* 28:4286-4298 (1998)). Conversely, IL-13 but not IL-4 expression seems to promote changes in epithelial tissue architecture and mucous expression in the lung (Kuperman, et al., *Nat. Med.* 8:885-889 (2002) and Wills-Karp, et al., *Science* 282:2258-2261 (1998). In humans, mutations in the shared IL-4 receptor α chain are associated with atopic disease, although not in all populations studied (Hackstein, et al., *Immunogenetics* 53:264-269 (2001); Hall, *Respir. Res.* 1:6-8 (2000); Hershey, et al., *N. Engl. J. Med.* 337:1720-1725 (1997); Howard, et al., *Am. J. Hum. Genet.* 70:230-236 (2002); Karp and Wills-Karp, *Microbes Infect.* 3:109-119 (2001); Mitsuyasu, et al., *Nat. Genet.* 19:119-120 (1998); Olavesen, et al., *Immunogentics* 51:1-7 (2000); and Risma, et al., *J. Immunol.* 169:1604-1610 (2002)). In murine models, knockout of the IL-4 receptor shared IL-4 receptor α chain and knockouts of the IL-4 receptor activated STAT-6 signaling factor almost completely eliminate the allergic phenotype although some atopic response can be rescued with prolonged allergic stimulation (Gessner and Rollinghoff, *Immunobiology* 201:285-307 (2000); Grunewald, et al., *Int Arch Allergy Immunol* 125:322-8 (2001); Nelms, et al., *Annu Rev Immunol* 17:701-38

(1999); Noben-Trauth, et al., *Proc Natl Acad Sci USA* 94:10838-43 (1997); Noben-Trauth, et al., *Eur J Immunol* 32:1428-33 (2002); Quelle, et al., *Mol Cell Biol* 15:3336-43 (1995); Shimoda, et al., *Nature* 380:630-3 (1996); So, et al., *FEBS Lett* 518:53-9 (2002); and Zhu, et al., *J Immunol* 166: 7276-81 (2001)). Selective blockade of the IL-4/IL-13 receptor with a mutated IL-4 competitive peptide antagonist also blocked allergic sensitization in the mouse (Tomkinson, et al., *J. Immunol.* 166:5792-5800 (2001)).

These observations illustrate the importance of the IL-4/IL-13 signaling pathway as a target for pharmacologic intervention to prevent or treat allergic diseases. Knockout of the shared IL-4 receptor α chain required for both IL-4 and IL-13 eliminated both IgE production and asthma-like lung pathology, suggesting a unique role for IL-13 in asthma and some atopic skin diseases (Wills-Karp, et al., *Science* 282:2258-2261 (1998); Wills-Karp, *Respir. Res.* 1:19-23 (2000); and Herrick, et al., *Clin. Invest.* 105:765-775 (2000)). A recent clinical trial of a soluble fragment of the human shared IL-4 receptor α chain capable of binding IL-4 (but not IL-13) showed some effectiveness in severe asthmatics (Steinke and Borish, *Respir. Res.* 2:66-70 (2002)). Importantly, no adverse effects related to loss of IL-4 function were noted in the lung or systemically in these human subjects.

IL-4 and IL-13 are also required for systemic immunity to some bacterial and parasitic infections (Karp and Wills-Karp, *Microbes Infect.* 3:109-119 (2001); Mountford, et al., *Infect. Immun.* 69:228-236 (2001); and Mohrs, et al., *J. Immunol.* 162:7302-7308 (1999)), and receptor inactivation could result in increased infections in targeted tissues. Targeted inactivation of the IL-4 receptor α chain to particular tissues such as lung or other tissues such as the digestive tract where polymorphisms of the IL-4 receptor are associated with inflammatory bowel disease (Klein, et al., *Genes Immun.* 2:287-289 (2001)) could be of benefit to prevent systemic immunodeficiency. Systemic immuno-modulation via targeted inactivation of the IL-4 receptor α chain might also be of benefit under some circumstances since loss of the IL-4/IL-13 receptor prevents the onset of systemic autoimmune diabetes in the mouse (Grossman and Paul, *Curr. Opin. Immunol.* 13:687-698 (2001) and Radu, et al., *PNAS USA* 97:12700-12704 (2000) and some tumors are also responsive to IL-4 Strome, et al., *Clin. Cancer Res.* 8:281-286 (2002); Essner, et al., *J. Gastrointest. Surg.* 5:81-90 (2001); and ter-abe, et al., *Nat. Immunol.* 1:515-520 (2000)). IL4 has also been shown to differentially modulate HIV1 replication in primary cells of the monocyte/macrophage lineage. The imbalance of IL4/IL13 TH2 cytokines over TH1 cytokines is thought to facilitate replication of viruses including the HIV-1, Influenza, and Epstein-Barr virus.

It is therefore an object of the present invention to provide nuclease resistant EGS that provide a therapy for respiratory diseases, IL-4 and/or IL-13 dependent systemic diseases, and viruses.

It is further an object of the present invention to provide EGS that target proteins required for generation and modification of the immunoglobulin and T-cell repertoire.

It is further an object of the present invention to provide EGS that target viral replication.

It is further an object of the present invention to provide formulations for inhalation containing EGS and methods for treating inflammatory and related diseases utilizing such formulations.

It is further an object of the present invention to provide a formulation that inactivates IL-4 receptror α chain and methods of use thereof.

BRIEF SUMMARY OF THE INVENTION

RNA oligonucleotides termed External Guide Sequence (EGS) and RNAi have been described that target specific gene expression by site-specific cleavage of mRNA. EGS serve as an RNA catalyst or ribozyme by directing bound mRNA to the endogenous ribonuclease, such as ubiquitous cellular enzyme RNAse P in bacteria and its homologue in humans and other mammals. EGS are described that target proteins required for generation and modification of the immunoglobulin and T-cell repertoire that are useful for treatment or prevention of inflammatory or related diseases, by inhibiting or reducing one or more symptoms of the diseases or disorders. EGS are described that target cytokines, cytokine receptors, or transcription factors involved in asthma and that target the Influenza virus. In one embodiment, an EGS is described that targets human interleukin (IL)-4 receptor α mRNA, an important cytokine receptor in the pathogenesis of asthma and allergic disease expressed in pulmonary tissues. In another embodiment, an EGS is described that targets signal transducer and activator of transcription 6 (STAT6), which participates in a signaling pathway which is initiated by IL-4 and IL-13. In another embodiment, an EGS is described that targets Adenosine Recptor A1 (A1). Adenosine is a multipurpose signal molecule that regulates a variety of cellular functions and is released under conditions of physiological stress. The actions of adenosine are mediated through four receptors subtypes (A1, A2A, A2B and A3). A1 is the primary form of adenosine receptor expressed in epithelial cells and is upregulated in asthma. In another embodiment, an EGS is described that targets the recombination activating RAG-1 RNA, essential for proper formation and function of B cell and T cell receptors. RAG-1 acts together with RAG-2 as a heterodimer in the initiation of the process of antigen receptor gene segment assembly. In another embodiment, EGS are described that target genes of the Influenza virus.

Formulations suitable for administration of an EGS for treatment of inflammatory or related disease are described. The formulations may be administered via inhalation, injection, orally, or may be in the form of an ointment, lotion, cream, gel, drop, suppository, spray, liquid, powder, granule, solution, suspension, capsule, or tablet. The formulations contain an effective amount of EGS to reach a final EGS concentration of 1 micromolar or less in pulmonary extracellular fluid to decrease levels of targeted mRNA for days or weeks.

Methods of treating inflammatory or related diseases by administering an effective amount of an EGS in a pharmaceutically acceptable carrier are also described. In preferred embodiments, the inflammatory disease is asthma, allergic rhinitis, food allergies, atopic skin disease such as eczema, IL-4 and/or IL-13 dependent malignancies, IL-4 and/or IL-13 dependent autoimmune diseases, and atopic diseases. In another preferred embodiment the disease is caused by the Influenza virus or IL-4 dependent replication of viruses such as HIV-1 and Epstein-Barr virus.

In one embodiment, nuclease resistant EGS are formulated for pulmonary delivery of catalytic RNA oligonucleotides, referred to as EGS-related Respirable Anti-Sense Oligonucleotide Sequences) or ERASONS, as a novel therapy in asthma and other atopic diseases. These EGS, as well as small nuclease resistant nucleotide sequences and related DNA expression vectors described herein, are expected to be useful in therapy of asthma and related respiratory diseases.

BRIEF DESCRIPTION OF THE DRAWINGS

FIG. 1c is the tRNA sequences including the T, variable and anti-codon loops that form a structure termed an external guide sequence (EGS) (SEQ ID NO:100) shown bound to mRNA target. EGS contains complementary sequences binding to a target RNA through complementary 5' and 3' regions. Predicted cleavage site of the target mRNA (arrow) shown.

FIG. 2 is T1 Nuclease mapping of the human shared IL-4 receptor a chain mRNA (SEQ ID NO:101). T1 nuclease sensitive G residues are underlined. The start codon of the IL-4 receptor α chain open reading frame is shown in bold type. Nucleotide numbers correspond to positions in the full-length RNA determined by cDNA sequencing and confirmed in this work. Potential EGS targets are shown in italics, with EGS1 and 2 targets shown surrounded by rectangular boxes.

FIG. 4a shows that in Ramos cells, activation of IL-4 transcription was significantly increased with a functional T loop versus mutated T loop as shown, human EGS sequence phIL4Re 1.1 versus mutated T-loop control phIL4Rmute1.1 (denoted Tmut) (p<0.05). Activation of IL-4 gene reporter was significantly greater with sequence matched human EGS either cotransfected phIL4Re1.1 or mutated T-loop control phIL4Rmute 1.1 (denoted Tmut) versus mismatched murine controls either pmIL4Re1.1 or pmIL4Rmute1.1 (p<0.05). Effects of mutated Tloop control phIL4Rmute1.1 presumably are due to some conventional antisense RNA effects in the absence of RNAse P. After addition of ionomycin, activation of IL-4 reporter was similar (p>0.05) with either co-transfected phIL4Re1.1 or mutated T-loop control phIL4Rmute1.1. IL-4 gene expression was not detectable above background with either pmIL4Re1.1 or pmIL4Rmute1.1 which contain complementary region differences at two nucleotides from corresponding human sequences in the EGS homologous regions.

FIG. 4b shows that in 45/2w11 cells, basal transcription increased in a dose-dependent manner with co-transfection of full-length pEGS1.1 (denoted E for transfection of 1 mcg pEGS1.1 and 0.5E for 0.5 mcg). NF-κB reporter denoted NFluc was included in some experiments as a control for non-specific effects of IL4 and ionomycin, results of NF-κB reporter are shown normalized to IL4 reporter by a factor of 10 l. A decrease in expression of the human IL-4 reporter was evident (p<0.05) with addition of IL-4 in the absence of EGS1 as shown, but transcription of both human IL-4 and NF-κB reporter were otherwise independent of IL-4 in the presence of EGS1 expression.

DETAILED DESCRIPTION OF THE INVENTION

Figure 1A:
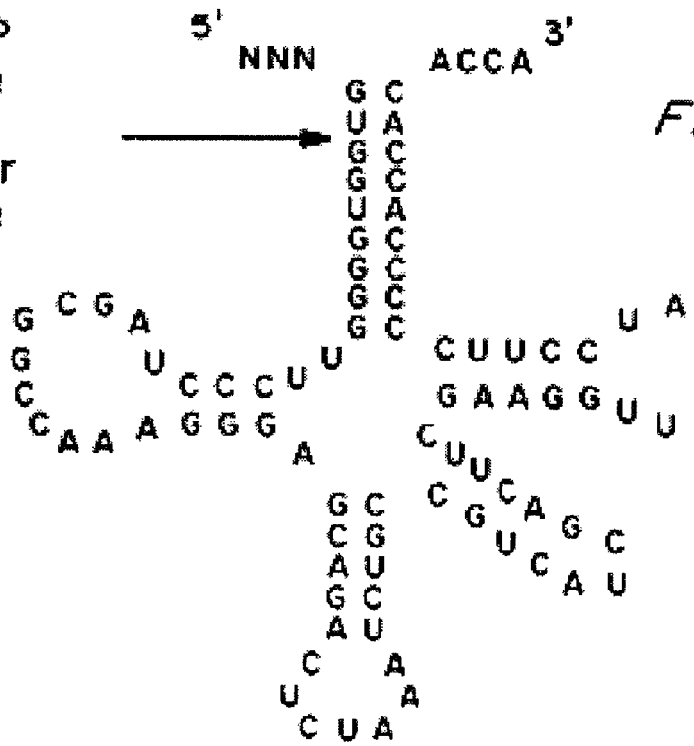
FIG. 1*a* is the structure and sequence of endogenous human tyrosine tRNA precursor RNA (SEQ ID NO:98) with site of precursor cleavage by RNAse P indicated by arrow.

RNA enzymes targeting respiratory diseases for therapy are described. Defined RNA sequences termed EGS (External Guide Sequences) are described that target regions of the influenza virus transcriptosome and mRNA from respiratory cytokines predicted or demonstrated to be effectively targeted by RNAse P. Specific targets include, but are not limited to, key conserved influenza genes and the shared IL4/IL13 common chain2 as well as other key inflammatory pathways such as NF-κB, TGF-β, adenosine and complement receptors.

Antisense technology is a promising gene-targeting approach for use in basic research and therapeutic applications. The gene-targeting agents include, but are not limited to, antisense oligonucleotides, antisense catalytic molecules (ribozyme or DNA enzyme), or an antisense molecule with an additional (guide) sequence, otherwise known as external guide sequences (EGS), that targets the mRNA for degradation by endogenous RNases such as RNase L and RNase P. It has been shown that binding of ribozymes and antisense phosphothioate molecules to their target RNAs can to be rate-limiting in vivo (Yu, et al., *J. Biol. Chem.* 273, 23524-23533 (1998)). EGS have several unique features over other gene-targeting agents. Targeting with these molecules results in irreversible cleavage of RNA that can be catalytic. Moreover, this targeting approach uses the cellular endogenous RNase P (or its equivalent) for degradation of the target mRNA and, therefore, assures the stability and efficiency of the targeting enzymes in the cellular environment. RNAse P/EGS Technology Ribonuclease P(RNase P) is a ribonucleoprotein complex found in all organisms. It is highly active in cells and is responsible for the maturation of 5' termini of all tRNAs, which account for approximately 2% of total cellular RNA. Human RNase P has at least nine polypeptides and a RNA subunit (H1 RNA). One of the unique features of RNase P is its ability to recognize structures, rather than the sequences, of substrates. This allows RNase P to hydrolyze different natural substrates in vivo or in vitro. Accordingly, any complex of two RNA molecules that resembles a tRNA molecule can be recognized and cleaved by RNase P. One of the RNA molecules is called the external guide sequence (EGS). An mRNA sequence can be targeted for RNase P cleavage by using EGSs to hybridize with the target RNA and direct RNase P to the site of cleavage. The EGSs used to direct human RNase P for targeted cleavage resemble three-quarters of a tRNA molecule and consist of two sequence elements: a targeting sequence complementary to the mRNA sequence and a guide sequence, which is a portion of the natural tRNA sequence and is required for RNase P recognition.

The region of the EGS complementary to target mRNA is in general shorter than the approximately 21 to 23 nucleotide complimentary region of a conventional antisense DNA oligonucleotide. This should reduce the possibility of off-site cleavage of other mRNA. Reduced off-site cleavage by EGS is also an advantage of EGS relative to RNAi, another new gene targeting approach in which 22 or 23 nucleotide double-stranded RNA oligonucleotides introduced into cells serve as a catalyst for degradation by the endogenous RNA Induced Silencing Complex (RISC) (Plasterk, *Science* 296:1263-1265 (2002)). Another potential advantage of EGS versus RNAi or other antisense technologies is due to the presence of large amounts of RNAse P present in all cells at all times. For RNAi expression of the RISC must be induced, may not be induced in all cell types, and may be saturated by multiple mRNA targets, these limitations due not appear to apply to EGS.

Applications of RNase P/EGS Technology

Current therapies for asthma and related atopic diseases are effective but inadequate from several perspectives. First, while inhaled agents such as corticosteroids and long acting beta agonists or leukotriene antagonists can block the symptoms of asthma, these agents do not arrest the progress of the disease or subsequent tissue remodeling. EGS therapy that targets IL4/13 and other inflammatory cytokines directly as primary prevention of asthma is described. Second existing therapy requires daily or more frequent dosing leading to problems with compliance particularly in the young. EGS therapy could be on a weekly basis due to prolonged effects of EGS upon receptor expression and function. Finally, newer targeted molecules with longer duration of action such as the anti-IgE receptor omalizumab (xolair) are very costly and difficult to administer, produce and store. EGS are stable, readily prepared in large quantities resulting in cost savings and highly cost effective and easy to administer due to their unique chemical properties and mechanism of active. EGS cost is estimated to be minimal in comparison with existing therapies such as vaccines which must be re-designed yearly or small molecules which must be taken daily for prophylaxis.

EGS targeting specific molecular targets such as cytokine receptors has the advantages of rational and inexpensive design principles and the potential to target multiple molecular targets. Conventional antisense DNA termed RASONS (Nyce and Metzger, *Nature* 385:721-725 (1997); Sandrasagra, et al., *Antisense Nucleic acid Drug Dev.* 12:177-181 (2002); and Finotto, et al., *J. Exp. Med.* 193:1247-1260 (2001)) has been introduced in an attempt to regulate cytokine expression in these diseases. Catalytic RNA external guide sequences (EGS) (Gopalan, et al., *J Biol Chem* 277:6759-62 (2002); Guerrier-Takada, et al., *Methods Enzymol* 313:442-56 (2000); Plehn-Dujowich, et al., *Proc Natl Acad Sci USA* 95: 7327-32 (1998); and Rosenwasser, et al., *Am J Respir Crit Care Med* 156:S152-5 (1997)) and the recently discovered phenomena of RNA interference or RNAi (Plasterk, *Science* 296:1263-1265 (2002)) utilize small RNA molecules introduced into eukaryotic cells to inactivate a particular target RNA. Targeted inactivation of the IL-4 receptor α chain can provide a means of modulating the combined pathogenic effects of IL-4 and IL-13 with a single therapeutic agent. Importantly, eliminating receptor expression would modulate autocrine and paracrine signaling (signaling between the cell and itself or cells in close contact) as well as signaling through soluble cytokine release.

A number of applications of molecules include therapy of allergic and autoimmune diseases and asthma, based on the assumption that these molecules are able to decrease expression of the functional IL-4 receptor α chain in vivo. Previous studies have demonstrated that EGS-based RNA inactivation of targeted mRNA in vivo can be orders of magnitude more effective than gene inactivation by conventional antisense DNA oligonucleotides (Guerrier-Takada, et al., *Methods Enzymol* 313:442-56 (2000) and Plehn-Dujowich, et al., *Proc Natl Acad Sci USA* 95: 7327-32 (1998)) which have a different mechanism of action either by steric blocking of mRNA translation or by causing DNA/mRNA hybrid degradation by endogenous RNAse H (Nyce and Metzger, *Nature* 385:721-725 (1997) and Sandrasagra, et al., *Antisense Nucleic acid Drug Dev.* 12:177-181 (2002)). If delivered effectively to pulmonary tissues, inhaled EGS ribozymes can have advantages over conventional antisense DNA oligonucleotides because of their ability to act as a co-catalyst for the ubiquitous RNAse P and the potential for a single EGS to recycle through multiple rounds of mRNA cleavage. However, applications of EGS technology to therapy of asthma and other atopic diseases have not been described previously.

Altman and co-workers first showed that a respiratory illness could be targeted by RNAse P and EGS using influenza virus (Plehn-Dujowich and Altman, *PNAS USA* 95:7327-7332 (1998). Dreyfus et al., published after the priority date of the present application, subsequently demonstrated that a similar strategy could target the shared IL4/IL13 receptor chain, and proposed inhalation therapy of respiratory illness with small nuclease resistant EGS sequences (Dreyfus, et al., *Int. Immunopharmacol.* 4(8):1015-1027 (2004)). A number of viral diseases and other cellular gene pathways have been targeted by RNAse P using EGS, potentially leading to therapies for other chronic illness such as HIV/AIDS, hepatitis, and cancer (Raj and Liu, *Gene* 313:59-69 (2003)). EGS are not gene therapy because they do not cause permanent alteration of gene expression, but are an epigenetic therapy in which exogenous nucleic acids transiently alter gene expression. Importantly, respiratory diseases are ideal targets for nucleic acid based epigenetic therapy since negatively charged small nucleic acids with either DNA or RNA based backbones are spontaneously taken up into the pulmonary epithelium in an active state with or without carrier molecules.

Gene targeting with small nuclease resistant EGS eliminates the need for gene therapy or stable transfection of cells with viral vectors to generate EGS. Applications of EGS technology as innovative therapy for respiratory diseases are described. Because IL4/IL13 signaling utilize a common receptor chain denoted the IL4 receptor common chain, elimination of both IL4 and IL 13 was possible by a single gene targeting reagent described herein. The mRNA sequences of molecules known or suspected to be important in the pathogenesis of asthma and related respiratory diseases were screened to identify those targets with the EGS target consensus GNNNNNU located intproximity to the mRNA start codon (see Table 1 and Table 2).

Interestingly, some evidence suggests that influenza and other pathogenic respiratory viruses may induce an asthma-like state in the lungs with increased TH2 cytokines such as IL4 and IL13 possibly augmented rather than suppressed by TH1 cytokines such as interferon, providing a link between viral infections and more chronic lung diseases (Umetsu, *Nat. Med.* 10(3):232-234 (2004) and Dahl, et al., *Nat. Immunol.* 5(3):337-343 (2004). Thus respiratory viral pathogenesis can illustrate and respond to therapy directed at both mechanisms of viral pathogenesis and also suggest novel strategies for asthma and related post viral respiratory illness (Tsitoura, et al., *J. Immunol.* 165(6):3484-3491 (2000) and Schwarze and Gelfand, *Eur. Respire.* 19(2):341-349 (2002).

More recently others have shown that small double stranded RNA oligonucleotides denoted RNAi can also block the replication of influenza in vitro and in vivo (Ge, et al., *PNAS USA* 101(23):8676-8681 (2004); Tompkins, et al., *PNAS USA* 1010(23):8682-8686 (2004); and Zhou, et al., *FEBS Letters* 577:345-350 (2004)). Studies of RNAi are relevant to EGS for several reasons. First RNAi and EGS are both examples of small RNA molecules that direct mRNA targets for degradation by cellular enzymes, the RISC complex in the case of RNAi and RNAse P in the case of EGS. The existence of these endogenous enzyme complexes increases the potency of mRNA degradation relative to conventional anti-sense therapies which rely on steric interference with mRNA translation or targeting mRNA to the relatively low potency RNAse H (Heasman, *Dev. Biol.* 243(2):209-214 (2002)). These studies are an important milestone since they validate that nucleic acid based epigenetic therapies can be efficacious and appear to be safe in animal models of an important respiratory disease.

RNAse P targeting by EGS has advantages over RISC targeting with RNAi since RNAse P, an enzyme required for all replicating cells is more abundant than RISC which is induced only by certain inflammatory stimuli such as viral infections in cells (Plasterk, *Science* 296:1263-1265 (2002). Unlike double stranded RNA or similar RNAi which can in some circumstances turn on cellular inflammation, EGS are single stranded upon entry into the cell and remain primarily single stranded even when bound to target mRNA due to the non-based paired T-loop of the EGS. RNAi also seems to have unpredictable off targeting effects such as gene silencing or inflammatory response related to the antiviral functions of the RISC complex. Some viruses including influenza encode proteins that specifically inactivate RNAi. If the inflammatory and non-specific effects of RNAi upon cells do not prevent its eventual use in some applications such as for therapy of pandemic influenza, the possibility also exists for synergy between RNAi and EGS to permit multiple gene targeting or increased mRNA elimination since the effects of EGS occur in the cell nucleus while the effects of RNAi occur in the cytoplasm.

I. External Guide Sequences

An EGS is designed to base pair through hydrogen bonding mechanism with a target mRNA to form a molecular structure similar to that of a transfer RNA (tRNA). The EGS/mRNA target is then cleaved and inactivated by RNAse P. EGS are not consumed in this reaction, but instead can recycle as a catalyst through multiple cycles of target mRNA cleavage leading to target inactivation more effectively than conventional anti-sense DNA oligonucleotides. EGS combine the specificity of conventional antisense DNA for gene targeting with the catalytic potency of RNAse P. RNAse P is present in abundant quantities in all viable eukaryotic cells where it serves to process transfer RNA (tRNA) by cleavage of a precursor transcript.

Small RNA sequences have been described that target eukaryotic mRNA for degradation by endogenous RNAse P, a ubiquitous cellular enzyme that generates mature transfer RNA (tRNA) from precursor transcripts (Gopalan, et al., *J. Biol. Chem.* 277:6759-6762 (2002); Guerrier-Takada and Altman, *Methods Enzymol.* 313:442-456 (2000); and Plehn-Dujowich and Altman, *PNAS USA* 95:7327-7332 (1998)). A small RNA termed an External Guide Sequence (EGS) can be designed that mimics certain structural features of a tRNA molecule when it forms a bimolecular complex with another RNA sequence contained within a cellular messenger RNA (mRNA) (see FIG. 1). Thus, any mRNA can in principle be recognized as a substrate for RNAse P with both the EGS and RNAse P participating as cocatalysts although due to the complexity of the binding and cleavage steps the kinetics of the reaction are difficult to predict in vitro or in vivo (Gopalan, et al., *J. Biol. Chem.* 277:6759-6762 (2002) and Guerrier-Takada and Altman, *Methods Enzymol.* 313:442-456 (2000)).

Design of an EGS requires both knowledge of the mRNA primary sequence to be cleaved by RNAse P as well as the secondary structure of the mRNA sequences in the mRNA. EGS sequences must be complementary to the primary sequence of the targeted mRNA and the sequences in the mRNA must be exposed in a single-stranded conformation within the mRNA secondary structure in order to bind to the EGS. Secondary structure of target mRNA can be approximated by computer modeling or determined empirically using nucleases or other RNA cleaving reagents well known to one of ordinary skill in the art. This analysis may be useful in locating regions of mRNA for targeting with complementary oligonucleotides including conventional DNA antisense oligonucleotides and catalytic RNA.

RNAase P is a ribonucleoprotein having two components, an RNA component and a protein component. The RNA component of RNAase P is responsible for the catalytic cleavage which forms the mature 5' ends of all transfer RNAs. RNAase P is endogenous to all living cells that have been examined. During the studies on recognition of substrate by RNAase P, it was found that *E. Coli* RNAase P can cleave synthetic tRNA-related substrates that lack certain domains, specifically, the D, TψC and anticodon stems and loops, of the normal tRNA structure. For bacterial RNAse P a half-turn of an RNA helix and a 3' proximal CCA sequence contain sufficient recognition elements to allow the reaction to proceed. Using these principles, any RNA sequence can be converted into a substrate for bacterial RNAase P by using an external guide sequence, having at its 5' terminus nucleotides complementary to the nucleotides 3' to the cleavage site in the RNA to be cleaved and at its 5' terminus the nucleotides NCCA (N is any nucleotide).

EGS for promoting RNAase P-mediated cleavage of RNA has also been developed for use in eukaryotic systems as described by U.S. Pat. No. 5,624,824 to Yuan, et al., U.S. Pat. No. 6,610,478 to Takle, et al., WO 93/22434 to Yale University, WO 95/24489 to Yale University, and WO 96/21731 to Innovir Laboratories, Inc. As used herein, "external guide sequence" and "EGS" refer to any oligonucleotide or oligonucleotide analog that forms, in combination with a target RNA, a substrate for RNAase P.

Figure 1B:
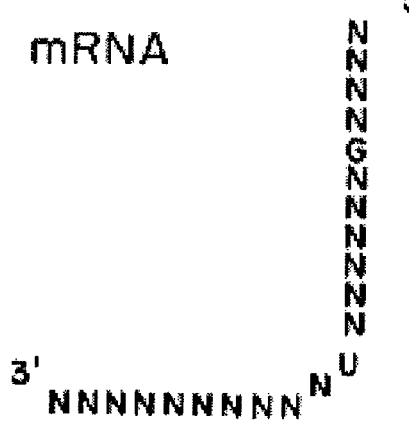
FIG. 1b is the target mRNA (SEQ ID NO:99) containing consensus 5' GNNNNNU without intrastrand base pairing that can be directed to RNAse P cleavage.

An external guide sequence for promoting cleavage by RNAase P contains sequences which are complementary to the target RNA and which forms secondary and tertiary structures similar to portions of a tRNA molecule (see FIG. 1A). In eukaryotes, including mammals, tRNAs are encoded by families of genes that are 73 to 150 base pairs long. tRNAs assume a secondary structure with four base paired stems known as the cloverleaf structure. The tRNA contains a stem, a D loop, a Variable loop, a TψC loop, and an anticodon loop. In one form, the EGS contains at least seven nucleotides which base pair with the target sequence 3' to the intended cleavage site to form a structure like the stem, nucleotides which base pair to form stem and loop structures similar to the TψC loop, the Variable loop and the anticodon loop, followed by at least three nucleotides that base pair with the target sequence to form a structure like the D loop.

Preferred guide sequences for eukaryotic RNAase P consist of a sequence which, when in a complex with the target RNA molecule, forms a secondary structure resembling that of a tRNA cloverleaf or parts thereof. The desired secondary structure is determined using conventional Watson-Crick base pairing schemes to form a structure resembling a tRNA. Since RNAse P recognizes structures as opposed to sequences, the specific sequence of the hydrogen bonded regions is less critical than the desired structure to be formed. The EGS and the target RNA substrate should resemble a sufficient portion of the tRNA secondary and tertiary structure to result in cleavage of the target RNA by RNAase P. The sequence of the EGS can be derived from any tRNA. The sequences and structures of a large number of tRNAs are well known to one of ordinary skill in the art and can be found at least online at URL rna.wustl.edu/tRNAdb. The consensus sequence for RNAse P recognition of tRNA molecules is GNNNNNU. The sequence obtained from the stem of the tRNA is altered to be complementary to the identified target RNA sequence. Target RNA is mapped by techniques well known to one of ordinary skill in the art for the consensus sequence. Such techniques include digestion of the target mRNA with T1 nuclease. Digestion with T1 nuclease cleaves RNA after guanine (G) residues that are exposed in solution and single-stranded, but not after G residues that are buried in the RNA secondary structure or base paired into doublestranded regions. The reaction products form a ladder after size fractionation by gel-electrophoresis. A T1 sensitive site is detected as a dark band is compared to the target mRNA sequence to identify RNAse P consensus sequences. The complimentary sequence from the target mRNA is used for the EGS. The complementary sequences may consist of as few as seven nucleotides, but preferably include eleven nucleotides, in two sections which base pair with the target sequence and which are preferably separated by two unpaired nucleotides in the target sequence, preferably UU, wherein the two sections are complementary to a sequence 3' to the site targeted for cleavage.

Figure 1C:
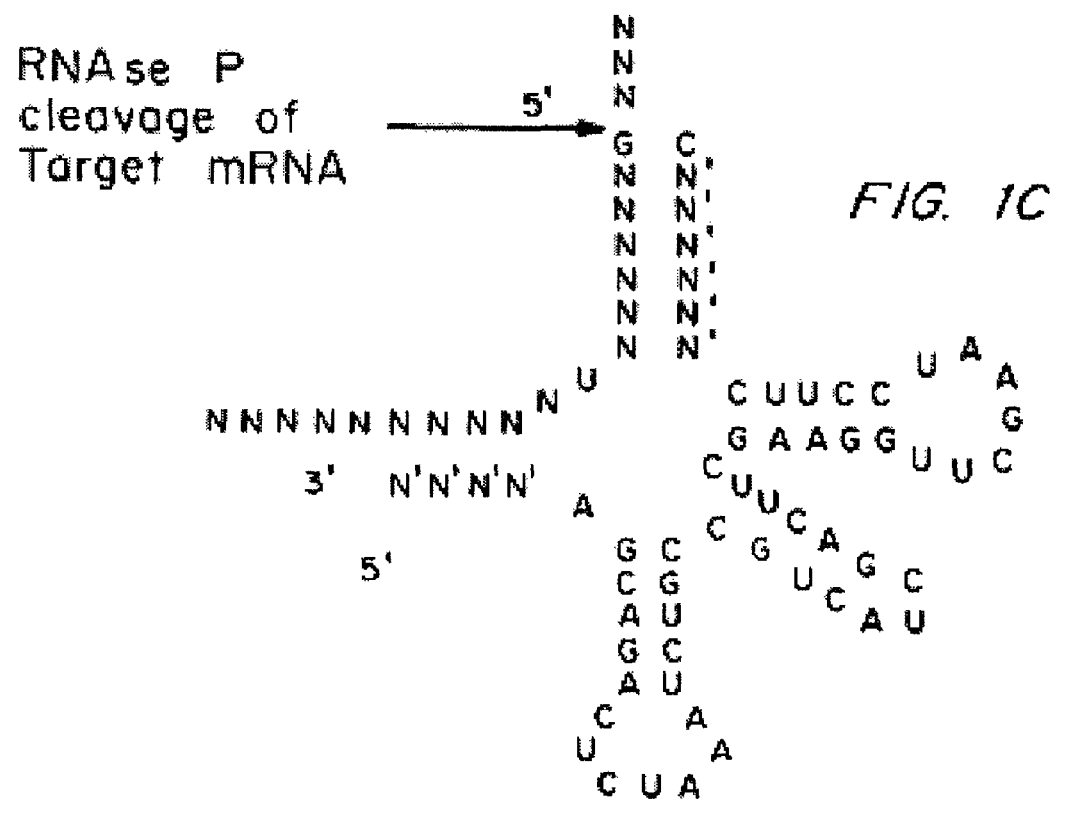

The remaining portion of the guide sequence, which is required to cause RNAase P catalytic RNA to interact with the EGS/target RNA complex, is herein referred to as an RNAase P binding sequence. The anticodon loop and the Variable loop can be deleted and the sequence of the TψC loop can be changed without decreasing the usefulness of the guide sequence. An example of a external guide sequence in association with a target RNA molecule is shown in FIG. 1C. External guide sequences can also be derived using in vitro evolution techniques (see U.S. Pat. No. 5,624,824 to Yuan, et al. and WO 95/24489 to Yale University).

Suitable EGS include, but are not limited to, EGS targeting the interleukin-4 receptor α chain, the stat-6 transcription factor (STAT6), the adenosine 1 receptor (A1), and the RAG-1 recombinase which are all required for generation and modification of the immunoglobulin and T-cell repertoire. The IL-4 receptor α chain gene has been cloned in swine, horses, sheep, mice, and humans (Zarlenga, et al., *Vet. Immunol. Immunopathol.* 101(3-4):223-34 (2004), Solberg, et al., *Vet. Immunol. Immunopathol.* 97(3-4):187-194 (2004), Hilton, et al., *PNAS USA,* 93(1):497-501 (1996), Mosley, et al., *Cell* 59(2):335-348 (1989), and Galizzi, et al., *Int. Immunol.* 2(7):669-675 (1990). The STAT 6 gene has been cloned in mice and humans (Quelle, et al., *Mol. Cell. Biol.* 15(6):3336-3343 (1995), Arava, et al., *Diabetes* 48(3):552-556 (1999). The Rag-1 gene has been cloned in trout, salamanders, mice, and humans (Zaarin, et al., *J. Immunol.* 159(9):4382-4394 (1997), Hansen and Kaattari, *Immunogenetics* 42(3):188-195 (1995), Frippiat, et al., *Immunogenetics* 52(3-4):264-275 (2001) and Schatz, et al., *Cell* 59(6):1035-1048 (1989). The adenosine receptor genes have been cloned in a variety of species, including humans, dogs, sheep, rabbits, mice, and guinea pigs (reviewed in Ralevic and Burnstock, *Pharmacological Reviews* 50(3):413-492(1998)). In a preferred embodiment the EGS targets the IL-4 receptor α chain. For each of these target genes choice of specific targeted sequences was suggested by their location of these sequences in proximity to the AUG start codon of the respective mRNA and a match to the RNAse P consensus GNNNNNU required for RNAse P cleavage. These targets all are postulated to play a role in human asthma, other pulmonary diseases, and other inflammatory diseases and can be inactivated by inhalation of EGS.

The sequences are as follows:
Targeting Sequence Flanking AUG of IL-receptor-alpha mRNA murine AUGGGGCGGCUUUGCACCA (SEQ ID NO: 1)
human AUGGGGUGGCUUUGCUCUG (SEQ ID NO: 2)

m = 2' O methyl
d = deoxy
Fl = fluorescein 5' label
dUmUAmGAAmU = T loop
mUAAmGAmUdU = reversed T loop mIL4Re1 = active EGS (murine)
mUmGmGmUmGmCmAmGmAmAmGmGdUmUAmGAAmUmC(SEQ ID NO: 3)
mCmUmUmCmGmCmCmGmCmCmCmAmCmA mIL4Re1mut = reversed T loop control (murine)
mUmGmGmUmGmCmAmGmAmAmGmGdUmUAmGaamUmC(SEQ ID NO: 4)
mCmUmUmCmGmCmCmGmCmCmCmAmCmA mIL4Re1 = active EGS/Fitc 5' labeled (murine) (Fl)
mUmGmGmUmGmCmAmGmAmAmGmGdUmUAmGAAmUmC(SEQ ID NO: 5)
mCmUmUmCmGmCmCmGmCmCmCmAmCmA hIL4Re1 = active EGS (human)
mCmAmGmAmGmCmAmGmAmAmGmGdUmUAmGAAmUmC(SEQ ID NO: 6)
mCmUmUmCmGmCmCmAmCmCmAmCmA hIL4Re1mut = reversed T loop control (human)
mCmAmGmAmGmCmAmGmAmAmGmGmUAAmGAmUdUmC(SEQ ID NO: 7)
mCmUmUmCmGmCmCmAmCmCmAmCmA hIL4Re1F = active EGS/Fitc 5' labeled (human) (Fl)
mCmAmGmAmGmCmAmGmAmAmGmGdUmUAmGAAmUmC(SEQ ID NO: 8)
mCmUmUmCmGmCmCmAmCmCmAmCmA Targeting Sequence Flanking AUG of STAT6 mRNA murine AUGUCUCUGUGGGGCCUA (SEQ ID NO: 9)
human AUGUCUCUGUGGGGUCUG (SEQ ID NO: 10)

m = 2' O methyl
d = deoxy
Fl = fluorescein 5' label
dUmUAmGAAmU = T loop
mUAAmGAmUdU = reversed T loop mSTAT6e1 = active EGS (murine)
mUmAmGmGmCmCmCmGmAmAmAmGmGdUmUAmGAAmUm (SEQ ID NO: 11)
CmCmUmUmCmCmAmGmAmGmAmCmAmCmA mSTAT6e1mut = reversed T loop control (murine)
mUmAmGmGmCmCmCmGmAmAmAmGmGmUAAmGAmUdUm (SEQ ID NO: 12)
CmCmUmUmCmCmAmGmAmGmAmCmAmCmA mSTAT6e1F = active EGS/Fitc 5' labeled (murine) (Fl)
mUmAmGmGmCmCmCmGmAmAmAmGmGdUmUAmGAAmUm (SEQ ID NO: 13)
CmCmUmUmCmCmAmGmAmGmAmCmAmCmA hSTAT6e1 = active EGS (human)
mCmAmGmAmCmCmCmCmGmAmAmAmGmGdUmUAmGAAmUm (SEQ ID NO: 14)
CmCmUmUmCmCmAmGmAmGmAmCmAmCmA hSTAT6e1mut = reversed T loop control (human)
mCmAmGmAmCmCmCmCmGmAmAmAmGmGmUAAmGAmUdUm (SEQ ID NO: 15)
CmCmUmUmCmCmAmGmAmGmAmCmAmCmA hSTAT6e1F = active EGS/Fitc 5' labeled (human) (Fl)
mCmAmGmAmCmCmCmCmGmAmAmAmGmGdUmUAmGAAmUm (SEQ ID NO: 16)
CmCmUmUmCmCmAmGmAmGmAmCmAmCmA Synthetic Oligonucleotide Sequences were:

phIL4Re1.1 (targeting human IL4R GGGTGGCTTTGCT (SEQ ID NO: 17), T loop underlined)

S5' (SEQ ID NO: 18)
GAGCAACGTCATCGACTTCGAAGGTTCGAATCCTTCGCCA
CCCACCATTTTTAA,

A5' (SEQ ID NO: 19)
AGCTTTAAAAATGGTGGGTGGCGAAGGATTCGAACCTTCGAAGTCGA
TGACGTTGCTCTGCA, phIL4Rmute1.1 (control for phIL4Re1.1, mutant T loop underlined)

```
S5'                                          (SEQ ID NO: 20)
GAGCAACGTCATCGACTTCGAAGGGATCCGCCTTCGCCACCCACCAT
TTTTAA,

A5'                                          (SEQ ID NO: 21)
AGCTTTAAAAATGGTGGGTGGCGAAGGCGGATCCCCTTCGAAGTCGA
TGACGTTGCTCTGCA pmIL4Re1.1 (targeting murine IL4R GGGTGGCTTTGCT
(SEQ ID NO: 22), T loop underlined)

S5'                                          (SEQ ID NO: 23)
GTGCAACGTCATCGACTTCGAAGGTTCGAATCCTTCGCCGCCCACCA
TTTTTAA

A5'                                          (SEQ ID NO: 24)
AGCTTTAAAAATGGTGGGCGGCGAAGGATTCGAACCTTCGAAGTCGA
TGACGTTGCACTGCA
pmIL4Rmute1.1 (control for pmIL4R, mutant T loop
underlined)

S5'                                          (SEQ ID NO: 25)
GTGCAACGTCATCGACTTCGAAGGGGATCCGCCTTCGCCGCCCACCA
TTTTTAA

A5'                                          (SEQ ID NO: 26)
AGCTTTAAAAATGGTGGGCGGCGAAGGCGGATCCCCTTCGAAGTCGA
TGACGTTGCACTGCA
```

Targeting Sequence Flanking AUG of Adenosine Receptor mRNA

```
murine ATGCCGCCGTACATCTCG                   (SEQ ID NO: 27)
human  ATGCCGCCCTCCATCTCA                   (SEQ ID NO: 28)

m = 2' O methyl
d = deoxy
Fl = fluorescein 5' label
dUmUAmGAAmU = T loop
mUAAmGAmUdU = reversed T loop mARe1 = active EGS (murine)
mCmGmAmGmAmUmGmGmAmAmGmGdUmUAmGAAmUm (SEQ ID NO: 29)
CmCmUmUmCmCmGmGmCmGmGmCmAmCmCmA mARe1mut = reversed T loop control for mARe1
mCmGmAmGmAmUmGmGmAmAmGmGmUAAmGAmUdUm (SEQ ID NO: 30)
CmCmUmUmCmCmGmGmCmGmGmCmAmCmCmA mARe1F = active EGS/Fitc 5' labeled mARe1
(Fl)mCmGmAmGmAmUmGmGmAmAmGmGdUmUAmGA (SEQ ID NO: 31)
AmUmCmCmUmUmCmCmGmGmCmGmGmCmAmCmCmA hARe1 = active EGS (human)
mUmGmAmGmAmUmGmGmAmAmGmGdUmUAmGAAmUm (SEQ ID NO: 32)
CmCmUmUmCmCmGmGmCmGmGmCmAmCmCmA
```

Targeting Sequence Flanking AUG of RAG1 mRNA

```
murine ATGGCTGCCTCCTTGCCGTCT               (SEQ ID NO: 33)
human  ATGGCAGCCTCTTTCCCACCC               (SEQ ID NO: 34)

m = 2' O methyl
d = deoxy
Fl = fluorescein 5' label
dUmUAmGAAmU = T loop
mUAAmGAmUdU = reversed T loop mRAG1e1 = active EGS (murine)
mCmGmGmCmAmAmGmGmAmAmGmGdUmUAmGAAmUm (SEQ ID NO: 35)
CmCmUmUmCmGmGmCmAmGmCmCmAmCmCmA mRAG1mute1 = reversed T loop control for mRAG1e1
mCmGmGmCmAmAmGmmGmAmAmGmGUAAmGAmUdUm (SEQ ID NO: 36)
CmCmUmUmCmGmGmCmAmGmCmCmAmCmCmA mRAG1e1F = active EGS/Fitc 5' labeled mRAG1e1
(Fl)mCmGmGmCmAmAmGmGmAmAmGmGdUmUAmGA (SEQ ID NO: 37)
AmUmCmCmUmUmCmGmGmCmAmGmCmCmAmCmCmA hRAG1e1 = active EGS (human)
mUmGmGmAmAmAmGmAmAmGmGdUmUAmGAAmUm (SEQ ID NO: 38)
CmCmUmUmCmGmGmCmUmGmCmCmAmCmCmA
```

Suitable EGS also include, but are not limited to, the EGSs generated from the target sequences listed in Tables 1 and 2. Table 1 lists target sequences, for asthma cytokines, cytokine receptors, and related genes. Table 2 lists target sequences for genes of the influenza virus. Target sequences were identified either by match to consensus GNNNNNU nuclease S1 mapping and confirmed in vivo (IL4R E, Flu E), or by proximity to the start codon of the target mRNA and match to consensus GNNNNNU (other target sequences).

Asthma cytokine genes IL-4, IL-13 common receptor alpha and IL13 cytokine and related transcription factor STAT6 were identified as candidates for EGS therapy based upon match to consensus and review of existing literature (Dreyfus, et al., *Int. Immunopharmacol.* 4(8):1015-27 (2004); Borish, et al., *J. Allergy Clin. Immunol.* 0.107.(6.): 963-70 (2001); Chu and Paul, *Mol Immunol* 35:487-502 (1998); Dent, et al., *Proc Natl Acad Sci USA* 95:13823-13828 (1998); Grunig, *J. Clin. Invest.* 112(3):329-31 (2003); Wills-Karp, et al., *Science* 282:2258-2261 (1998); Zhu, et al., *J Immunol* 166:7276-7281 (2001); and Zhu, et al., *J. Immunol.* 168(6):2953-62 (2002)). Adenosine also acts through multiple receptors, particularly the ADE1 receptor to increase transcription of IL4 and IL13 in a positive feedback loop that can also potentially be targeted by EGS (Grunig, *J. Clin. Invest.* 112(3):329-31 (2003); Blckburn, et al., *J. Clin. Invest.* 112(3):332-344 (2003); and Ryzhov, et al., *J. Immunol.* 172 (12):7726-7733 (2004)). Literature and gene sequence review also indicated other gene targets for EGS which act together with IL4 and 13 in the pathogenesis of asthma and allergy including cd40 and cd40 ligand required for activation of IgE synthesis in cooperation with IL4/13 (Warren and Berton, *J. Immunol.* 155:5637-5646 (1995) and Zhu, et al., *J. Immunol.* 173(12):7141-7149 (2004)), c3d complement receptor (Karp and Wills-Karp, *Microbes Infect.* 3:109-119 (2001); Park, et al., *Am. J. Respir. Crit. Care Med.* 169(6): 726-732 (2004); and Taube, et al., *Am. J. Respir. Crit. Care Med.* 168(11):1333-1341 (2003)), and NF-κB transcription factors p50 and p65 (Desmet, et al., *J. Immunol.* 173(9):5766-5775 (2004), Poynter, et al., *J. Immunol.* 173(11):7003-7009 (2004); and Zhou, et al., *Oncogene* 22(13):2054-2064 (2003)).

Asthma pathogenesis involves both acute inflammation mediated by IL4 and 13 and related molecules as noted above as well as permanent tissue changes or "remodeling" mediated by additional cytokines including IL-10, epithelial growth factors and TGF-B which activate the SMAD transcription factor family (Cohn, et al., *Annu. Rev. Immunol.* 22:789-815 (2004); Elias, *Chest* 126(2Suppl.): 111S.-116S (2004); Lee, et al., *J. Exp. Med.* 200(3):377-89 (2004); and Lee, et al., *Nat. Med.* 10(10): 1095-103 (2004)). Thus remodeling resulting from persistent inflammation are expected to be a target of EGS against these "remodeling" signals and receptors. A novel mechanism of pulmonary inflammation in asthma and other inflammatory lung disease may be activation of T cell receptor gene editing through transcription of the RAG genes required for both T and B cell responses to initiate the inflammatory pathway (Aronica, et al., *J. Allergy Clin. Immunol.* 114(6):1441-1448 (2004)). Thus the RAG genes are expected to be a target of EGS for treating pulmonary inflammation in asthma and other inflammatory lung disease.

TABLE 1

Target Sequences for Cytokines, Cytokine Receptors (R), and Transcription Factors (TF) Involved in Asthma

| Name | Target Sequence | Target | Species |
|---|---|---|---|
| hIl4R.E1 | AUGGGGUGGCUUUGCUCUG (SEQ ID NO: 2) | IL-4, 13 R | human |
| mIl4R.E1 | AUGGGGCGGCUUUGCACCA (SEQ ID NO: 1) | IL-4, 13 R | murine |
| hIl4R.E3 | GAAGGUCUUGCAGGAGC (SEQ ID NO: 39) | IL-4, 13 R | human |
| hStat6.E1 | AUGUCUCUGUGGGGUCUG (SEQ ID NO: 10) | STAT6 TF IL-4, 13 | human |
| mStat6.E1 | AUGUCUCUGUGGGGCCUA (SEQ ID NO: 9) | STAT6 TF IL-4, 13 | murine |
| hStat6.E2 | AUGUCUCUGUGGGGCUCUGGUCUCC (SEQ ID NO: 40) | STAT6 TF IL-4, 13 | human |
| hIL13.E1 | AUGGCGCUUUUGUUGACCACGGU (SEQ ID NO: 41) | IL-13 cytokine | human |
| hIL13.E2 | AUGGCGCUUUUGUUGACCACGGU (SEQ ID NO: 42) | IL-13 cytokine | human |
| hCD40L.E1 | GUUUUUCUUAUCACC (SEQ ID NO: 43) | CD40 ligand | human |
| hCD40L.E2 | GAAGGCUUUGUGA (SEQ ID NO: 44) | CD40 ligand | human |
| hCD40L.E3 | GAUACCAUUUCAACUUU (SEQ ID NO: 45) | CD40 ligand | human |
| hCD40.E1 | AUGGUUCGUCUGCCUCUGCA (SEQ ID NO: 46) | CD40 R | human |
| hCD40.E2 | GUCUGCCUCUGCAGUGC (SEQ ID NO: 47) | CD40 R | human |
| hCD40.E3 | GCCAUGGUUCGUCUGCCU (SEQ ID NO: 48) | CD40 R | human |
| hC3dR.E1 | GCGGGCCUGCUCGGGGUUUUC (SEQ ID NO: 49) | C3d complement R | human |
| hC3dR.E2 | GGGGUUUUCUUGGCUCUCGUC (SEQ ID NO: 50) | C3d complement R | human |
| hAdeR.E1 | AUGCCGCCCUCCAUCUCA (SEQ ID NO: 51) | Adenosine-1 R | human |
| mAdeR.E1 | AUGCCGCCGUACAUCUCG (SEQ ID NO: 52) | Adenosine-1 R | murine |
| hTGFBR1.E1 | GGGACCAUGGAGGCGGCGGUC (SEQ ID NO: 53) | TGFβ R(1) | human |
| hTGFBR1.E2 | AUGGAGGCGGCGGUCGCUGCUCCGC (SEQ ID NO: 54) | TGFβ R(1) | human |

TABLE 1-continued

Target Sequences for Cytokines, Cytokine Receptors (R), and Transcription Factors (TF) Involved in Asthma

| Name | Target Sequence | Target | Species |
|---|---|---|---|
| hTGFBR2.E1 | AUGGGUCGGGGCUGCUCAGGGGCCUG (SEQ ID NO: 55) | TGFβ R(2) | human |
| hTGFB.E1 | AUGCCGCCCUCCGGGCUGCGG (SEQ ID NO: 56) | TGFβ cytokine | human |
| hSMAD4.E1 | AUGGACAAUAUGUCUAUUAC (SEQ ID NO: 57) | TGFβ TF | human |
| hSMAD4.E2 | GAACAAAUGGACAAUAUGUCU (SEQ ID NO: 58) | TGFβ TF | human |
| hEGFR.E1 | AUGCGACCCUCCGGGACGGCCGGGG (SEQ ID NO: 59) | EGF R | human |
| hEGFR.E2 | GCAGCAUGCGACCCUCCGGGAC (SEQ ID NO: 60) | EGF R | human |
| hIL10R.E1 | AUGCUGCCGUGCCUCGUAGU (SEQ ID NO: 61) | IL-10 R | human |
| hIL10R.E2 | GUAGUGCUGCUGGCGGCGCU (SEQ ID NO: 62) | IL-10 R | human |
| hIL10.E1 | AUGCACAGCUCAGCACUG (SEQ ID NO: 63) | IL-10 cytokine | human |
| hRAG1.E1 | AUGGCAGCCUCUUUCCCACC (SEQ ID NO: 64) | VDJ Recombinase | human |
| mRAG1.E1 | AUGGCUGCCUCCAUUGCCGU (SEQ ID NO: 65) | VDJ Recombinase | murine |
| hNFκBp65 | AUGGACGAACUGUUCCCCUCA (SEQ ID NO: 66) | NFκB TF p65 | human |
| hNFκBp65 | AUGGACGAUCUGUUUCCCCUCA (SEQ ID NO: 67) | NFκB TF p65 | murine |
| hNFκBp65 | AUGGACGAACUGUUCCCCUCAUCUUC (SEQ ID NO: 68) | NFκB TF p65 | human |
| hNFκBp65 | AUGGACGAUCUGUUUCCCCUCAUCUUU (SEQ ID NO: 69) | NFκB TF p65 | murine |
| hNFκBp50 | AUGGAGAGUUGCUACAACCCAGGUCUGG (SEQ ID NO: 70) | NFκB TF p50 | human |
| hNFκBp50 | AUGGAGAGUUGCUACAACCCAGGUCUGG (SEQ ID NO: 71) | NFκB TF p50 | human |

AUG sequences for some target sequences are shown in bold face target and sequences matching GNNNNNU are underlined.

Altman and co-workers demonstrated that EGS could inactivate influenza virus replication when directed at one or two conserved genes (Plehn-Dujowich and Altman, *PNAS USA* 95:7327-7332 (1998)). This work did not propose therapy of respiratory diseases such as asthma and influenza based upon small nuclease resistant EGS1. Inhaled small nuclease resistant EGS for influenza therapy is advantageous over expression of EGS from retroviral vectors due to the observation that small nuclease resistant EGS will be selectively taken up by pulmonary tissues. EGS that inactivate influenza virus replication are identified by identifying conserved genes that match the consensus GNNNNNU in the vicinity of the AUG start codon, and confirming that EGS targets are conserved between the H1N1 strain of influenza circulating both in 1998 and at present as well as the related genes from highly pathogenic avian influenza H5N1 strains circulating currently.

TABLE 2

Target Sequences for Genes of the Influenza Virus

| Name | Target Sequence | Target | Species |
|---|---|---|---|
| FluEF.E1 | AUGGAAAGAAUAAAAGAACU (SEQ ID NO: 72) | elongation factor | Flu H1N1 |
| FluEF.E1a | AUGGAGAAUAAAAGAAUU (SEQ ID NO: 73) | elongation factor | Flu H5N1 |
| FluEF.E2 | GUCGCAGUCUCGCACCCGCG (SEQ ID NO: 74) | elongation factor | Flu H1N1 |
| FluEF.E2a | GUCACAGUCCCGCACUCGCG (SEQ ID NO: 75) | elongation factor | Flu H5N1 |
| FluEF.E3 | GUACACAUCAGGAAGACAGG (SEQ ID NO: 76) | elongation factor | Flu H1N1 |
| FluNP.E1 | GAACAGAUGGAGACUGAUGG (SEQ ID NO: 77) | nucleo-capsid | Flu H1N1 |
| FluNP.E1a | GAACAGAUGGAAACUGAUGG (SEQ ID NO: 78) | nucleo-capsid | Flu H5N1 |
| FluNP.E2 | GCCAGAAUGCCACUGAAAUCA (SEQ ID NO: 79) | nucleo-capsid | Flu H1N1 |
| FluNP.E2a | GCCAGAAUGCUACUGAGAUCA (SEQ ID NO: 80) | nucleo-capsid | Flu H5N1 |
| FluAP.E1 | AUGGAAGACUUUGUGCGCACA (SEQ ID NO: 81) | Acidic Polymerase | Flu H1N1 |
| FluAP.E1a | AUGGAAGACUUUGUGCGCACA (SEQ ID NO: 82) | Acidic Polymerase | Flu H5N1 |
| FluAP.E2 | AUGGAAGACUUUGUGCGCACA (SEQ ID NO: 83) | Acidic Polymerase | Flu H1N1 |
| FluAP.E2a | AUGGAAGACUUUGUGCGCACA (SEQ ID NO: 84) | Acidic Polymerase | Flu H5N1 |
| FluAP.E3 | GCGACAAUGCUUCAAUCCAAU (SEQ ID NO: 85) | Acidic Polymerase | Flu H1N1 |
| FluAP.E3a | GCGACAAUGCUUCAAUCCAAU (SEQ ID NO: 86) | Acidic Polymerase | Flu H5N1 |
| FluAP.E4 | GCUUCAAUCCAAUGAUCGUCG (SEQ ID NO: 87) | Acidic Polymerase | Flu H1N1 |
| FluAP.E4a | GCUUCAAUCCAAUGAUUGUCG (SEQ ID NO: 88) | Acidic Polymerase | Flu H5N1 |
| FluNS.E1 | GUCAAGCUUUCAGGUAGACUG (SEQ ID NO: 89) | Non-Structural 1,2 | Flu H1N1 |
| FluNS.E1a | GUCAAGCUUUCAGGUAGACUG (SEQ ID NO: 90) | Non-Structural 1,2 | Flu H5N1 |
| FluNS.E2 | GGUAGACUGUUUCCUUUGGCA (SEQ ID NO: 91) | Non-Structural 1,2 | Flu H1N1 |
| FluNS.E2a | GGUAGACUGCUUUCUUUGGCA (SEQ ID NO: 92) | Non-Structural 1,2 | Flu H5N1 |

AUG sequences for some target sequences are shown in bold face target and sequences matching GNNNNNU are underlined. Differences between H5N1 human (1998) and H5N1 avian (2004) indicated by italic letter.

In order to create nuclease resistant EGS, chemical modifications are made which greatly enhance the nuclease resistance of EGS without compromising their biological function of inducing or catalyzing cleavage of RNA target. For example, one or more of the bases of an EGS can be replaced by 2' methoxy ribonucleotides or phosphorothioate deoxyribonucleotides using available nucleic acid synthesis methods well known to one of ordinary skill in the art. Synthesis methods are described by, for example, PCT WO 93/01286 by Rosenberg et al. (synthesis of sulfurthioate oligonucleotides); Agrawal et al., *Proc. Natl. Acad. Sci. USA* 85: 7079-7083 (1988); Sarin et al., *Proc. Natl. Acad. Sci. USA* 85: 7448-7794 (1989); Shaw et al., *Nucleic Acids Res* 19: 747-750 (1991) (synthesis of 3' exonuclease-resistant oligonucleotides containing 3' terminal phosphoroamidate modifications).

Degradation of oligonucleotide analogues is mainly attributable to 3'-exonucleases. Various 3'-modifications known in the art can greatly decrease the nuclease susceptibility of these analogues such as introduction of a free amine to a 3' terminal hydroxyl group of the EGS molecule. Cytosines in the sequence can be methylated, or an intercalating agent, such as an acridine derivative, can be covalently attached to a 5' terminal phosphate to reduce the susceptibility of a nucleic acid molecule to intracellular nucleases.

Chemical modifications also include modification of the 2' OH group of a nucleotide's ribose moiety, which has been shown to be critical for the activity of the various intracellular and extracellular nucleases. Typical 2' modifications include, but are not limited to, the synthesis of 2'-O-Methyl oligonucleotides, as described by Paolella et al., *EMBO J.* 11: 1913-1919 (1992), and 2'-fluoro and 2'-amino-oligonucleotides, as described by Pieken et al., *Science* 253: 314-317 (1991), and Heidenreich and Eckstain, *J. Biol. Chem* 267: 1904-1909 (1992). Portions of EGS molecules can also contain deoxyribonucleotides, which improve nuclease resistance by eliminating the critical 2' OH group. Nuclease resistant EGS as described above can also be obtained from suppliers such as Dharmacon (Boulder, Colo.).

II. Formulations

It has been shown that small nuclease resistant EGS are readily taken up into T24 bladder carcinoma tissue culture cells with carrier lipids at a concentration of 1 μMolar EGS and 10 μMolar lipid transfection reagents Lipofectin or Lipofectase (Ma, et al., *Antisense Nucleic Acid Drug Dev.* 8:415-426 (1998). Uptake of these EGS was noted in both cytoplasm and nuclei of nearly every cell using 5 fluoresceinated EGS detected by confocal microscopy. Significant decreases in targeted gene expression were demonstrated in this model in the absence of observed toxicity. These studies demonstrated that modified EGS can be used for targeted gene therapy of human diseases. The formulations contain an effective amount of EGS to reach a final EGS concentration of 1 micromolar or less in pulmonary extra-cellular fluid (approximately 10-15 cc) to decrease levels of targeted mRNA for days or weeks following intranasal administration. For example, this range of EGS concentration can be achieved by intranasal instillation of 0.01 micromoles of EGS. Like conventional asthma medications it is anticipated that EGS can be shipped through the mail and stored at room temperature, but unlike conventional therapy it is expected that a single dose will have therapeutic effects for days or even weeks due to long term effects upon target protein synthesis (Ma, et al., *Nat Biotechnol.* 18(1):58-61 (2000) and Ma, et al., *Antisense Nucleic Acid Drug Dev.* 8:415-426 (1998).

Nyce et al. have shown that antisense oligodeoxynucleotides (ODNs) termed RASONS (Respirable Anti-Sense OligoNucleotide Sequences) when inhaled bind to endogenous surfactant (a lipid produced by lung cells) and are taken up by lung cells without a need for additional carrier lipids (Nyce and Metzger, *Nature,* 385:721-725 (1997). These observations indicate that oligonucleotide therapy directed at the lung has particularly favorable rational and could alter disease in the lungs without systemic effects through localized or targeted effects of the therapy to lung tissues.

For therapeutic purposes, a DNA vector encoding an EGS molecule can be utilized, such as a plasmid DNA vector or retroviral vector. Methods for creating such vectors are well known to one of ordinary skill in the art (see for example, U.S. Pat. No. 5,869,248 to Yuan, et al., U.S. Pat. No. 5,728,521 to Yuan, et al., Zhang and Altman, *J. Mol. Biol.* 342:1077-1083 (2004); and Plehn-Dujowich and Altman, *PNAS USA* 95:7327-7332 (1998)).

The EGS may be formulated in a pharmaceutically acceptable carrier, as described below. The formulation containing the EGS is useful for treating a disease, disorder, or symptom of the disease or disorder, associated with the expression or activity of a target gene. More preferably, the formulation containing the EGS is useful for treating a disease, disorder, or symptom of the disease or disorder, associated with the expression or activity of IL-4 and/or IL-13, or other targets of the EGSs described above.

In one embodiment, the formulation contains at least two EGSs, designed to target the same or different genes, and a pharmaceutically acceptable carrier. Formulations containing multiple EGSs may provide improved efficiency of inhibition as compared to compositions comprising a single EGS. In addition, formulations containing multiple EGS directed to different targets may provide improved efficacy when treating disease or a symptom of the disease. The multiple EGSs may be combined in the same formualtion, or formulated separately. If formulated individually, the formulations containing the separate EGSs may contain the same or different carriers, and may be administered using the same or different routes of administration. Moreover, the formulations containing the individual EGSs may be administered substantially simultaneously, sequentially, or at preset intervals throughout the day or treatment period.

EGS may be administered topically, locally or systemically in a suitable pharmaceutical carrier. Remington's Pharmaceutical Sciences, 15th Edition by E. W. Martin (Mark Publishing Company, 1975), discloses typical carriers and methods of preparation. EGS may also be encapsulated in suitable biocompatible microcapsules, microparticles or microspheres formed of biodegradable or non-biodegradable polymers or proteins or liposomes for targeting to cells. Such systems are well known to those skilled in the art and may be optimized for use with the appropriate EGS.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

The formulations may also be encapsulated to protect the EGS against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations are known to one of ordinary skill in the art. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP 0043075.

Formulations for parenteral administration may include sterile aqueous solutions which may also contain buffers, liposomes, diluents and other suitable additives. For intramuscular, intraperitoneal, subcutaneous and intravenous use, the EGS containing formulations will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of EGS in the cells that express the target gene. Such substances include, for example, micellar structures, such as liposomes or capsids, as described below. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In a preferred embodiment, the EGS are formulated for pulmonary delivery. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorbtion occurs. The alveoli are covered by a thin epithelium without cilia or a mucus blanket and secrete surfactant phospholipids (J. S. Patton & R. M. Platz. Adv. Drug Del. Rev. 8:179-196 (1992)).

The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung (Gonda, I. "Aerosols for delivery of therapeutic an diagnostic agents to the respiratory tract," in Critical Reviews in Therapeutic Drug Carrier Systems, 6:273-313 (1990)). The deep lung, or alveoli, are the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per $cm^3$, porous endothelial basement membrane, and it is easily accessible. Therefore, intranasal delivery of complex molecules such as EGS may provide therapies for the treatment of a number of pulmonary diseases.

The term aerosol as used herein refers to any preparation of a fine mist of particles, which can be in solution or a suspension, whether or not it is produced using a propellant. Aerosols can be produced using standard techniques, such as ultrasonication or high pressure treatment.

Carriers for pulmonary formulations can be divided into those for dry powder formulations and for administration as solutions. Aerosols for the delivery of therapeutic agents to the respiratory tract have been developed. See, for example, Adjei, A. and Garren, J. Pharm. Res., 7: 565-569 (1990); and Zanen, P. and Lamm, J.-W. J. Int. J. Pharm., 114: 111-115 (1995). For administration via the upper respiratory tract, the formulation can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (*Remington's Pharmaceutical Sciences* 16th edition, Ed. Arthur Osol, page 1445 (1980)). One skilled in the art can readily determine a suitable saline content and pH for an innocuous aqueous solution for nasal and/or upper respiratory administration.

In another embodiment, solvents that are low toxicity organic (i.e. nonaqueous) class 3 residual solvents, such as ethanol, acetone, ethyl acetate, tetrahydofuran, ethyl ether, and propanol may be used for the formulations. The solvent is selected based on its ability to readily aerosolize the formulation. The solvent should not detrimentally react with the EGS. An appropriate solvent should be used that dissolves the EGS or forms a suspension of the EGS. A suspension is also referred to as a dispersion herein. The solvent moreover should be sufficiently volatile to enable formation of an aerosol of the solution or suspension. Additional solvents or aerosolizing agents, such as freons, can be added as desired to increase the volatility of the solution or suspension.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, Calif.).

A number of pharmaceutical preparations for pulmonary delivery of drugs has been developed. For example, U.S. Pat. No. 5,230,884 to Evans et al., discloses the use of reverse micelles for pulmonary delivery of proteins and peptides. Reverse micelles are formed by adding a little water to a nonpolar solvent (e.g. hexane) to form microdroplets. In this medium, a surfactant (detergent) will orient itself with its polar heads inward, so that they are in contact with the water and the hydrophobic tails outward. The tiny droplets of water are surrounded by surfactant, and the protein to be delivered is dissolved in the aqueous phase.

U.S. Pat. No. 5,654,007 to Johnson et al., discloses methods for making an agglomerate composition containing a medicament powder (e.g. proteins, nucleic acids, peptides, etc.) wherein a nonaqueous solvent binding liquid (a fluorocarbon) is used to bind the fine particles into aggregated units. The agglomerate composition has a mean size ranging from 50 to 600 microns and is allegedly useful in pulmonary drug delivery by inhalation.

These materials can be used for delivery of formulation to the lungs, modified as necessary to deliver the correct dosage of surface modifying agent at a desired rate and to a preferred location within the lung.

Dry powder formulations ("DPFs") with large particle size have improved flowability characteristics, such as less aggregation (Visser, J., Powder Technology 58: 1-10 (1989)), easier aerosolization, and potentially less phagocytosis. Rudt, S. and R. H. Muller, J. Controlled Release, 22: 263-272 (1992); Tabata, Y., and Y. Ikada, J. Biomed. Mater. Res., 22: 837-858 (1988). Dry powder aerosols for inhalation therapy are generally produced with mean diameters primarily in the range of less than 5 microns. Ganderton, D., J. Biopharmaceutical Sciences, 3:101-105 (1992); and Gonda, I. "Physico-Chemical Principles in Aerosol Delivery," in Topics in Pharmaceutical Sciences 1991, Crommelin, D. J. and K. K. Midha, Eds., Medpharm Scientific Publishers, Stuttgart, pp. 95-115, 1992, although a preferred range is between one and ten microns in aerodynamic diameter. Large "carrier" particles (containing no drug) have been co-delivered with therapeutic aerosols to aid in achieving efficient aerosolization among other possible benefits. French, D. L., Edwards, D. A. and Niven, R. W., J. Aerosol Sci., 27: 769-783 (1996).

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different EGS may be administered to target different regions of the lung in one administration.

Formulations for pulmonary delivery include unilamellar phospholipid vesicles, liposomes, or lipoprotein particles. Formulations and methods of making such formulations containing nucleic acid are well known to one of ordinary skill in the art. Liposomes are formed from commercially available phospholipids supplied by a variety of vendors including Avanti Polar Lipids, Inc. (Birmingham, Ala.). The liposome-associated EGS is prepared by mixing a solution of the EGS with reconstituted lipid vesicles. In one embodiment, the liposome can include a ligand molecule specific for a receptor on the surface of the target cell to direct the liposome to the target cell.

Toxicity and therapeutic efficacy of such formulations can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies preferably within a range of circulating concentrations that include the ED50 with little or no toxicity. The dosage may vary within this range depending upon the dosage form employed and the route of administration utilized. For any EGS used in the method of the invention, the therapeutically effective dose can be estimated initially from cell culture assays. A dose may be formulated in animal models to achieve a circulating plasma concentration range of the EGS that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or multiply, as discussed above, the EGSs can be administered in combination with other known agents effective in treatment of diseases. In any event, the administering physician can adjust the amount and timing of EGS administration on the basis of results observed using standard measures of efficacy known in the art.

III. Method of Administration

The formulations may be administered by any means known in the art including, but not limited to oral or parenteral routes, including intravenous, intramuscular, intraperitoneal, subcutaneous, transdermal, and airway (aerosol) administration. In preferred embodiments, the formulations are administered via inhalation or nasal application to the lung. The formulations are administered to a patient in need of treatment or prophylaxis. The formulations can be administered to animals or humans. Concentration of EGS is determined to approximate 1 micromolar in pulmonary fluids, which previous studies demonstrate is optimal for gene targeting in vitro (Ma, et al., *Nat. Biotechnol.* 18(1):58-61 (2000)).

For pulmonary administration, formulations can be administered using a metered dose inhaler ("MDI"), a nebulizer, an aerosolizer, or using a dry powder inhaler. Suitable devices are commercially available and described in the literature.

Inhaled aerosols have been used for the treatment of local lung disorders including asthma and cystic fibrosis (Anderson et al., *Am. Rev. Respir. Dis.*, 140: 1317-1324 (1989)) and have potential for the systemic delivery of peptides and proteins as well (Patton and Platz, *Advanced Drug Delivery Reviews*, 8:179-196 (1992)). Considerable attention has been devoted to the design of therapeutic aerosol inhalers to improve the efficiency of inhalation therapies. Timsina et. al., *Int. J. Pharm.*, 101: 1-13 (1995); and Tansey, I. P., *Spray Technol. Market*, 4: 26-29 (1994).

The formulation may be administered alone or in any appropriate pharmaceutical carrier for administration to the respiratory system. Delivery is achieved by one of several methods. For example, the patient can mix a dried powder of EGS with solvent and then nebulize it. It may be more appropriate to use a pre-nebulized solution, regulating the dosage administered and avoiding possible loss of suspension. After nebulization, it may be possible to pressurize the aerosol and have it administered through a metered dose inhaler (MDI). Nebulizers create a fine mist from a solution or suspension, which is inhaled by the patient. The devices described in U.S. Pat. No. 5,709,202 to Lloyd, et al., can be used. An MDI typically includes a pressurized canister having a meter valve, wherein the canister is filled with the solution or suspension and a propellant. The solvent itself may function as the propellant, or the formulation may be combined with a propellant, such as freon. The formulation is a fine mist when released from the canister due to the release in pressure. The propellant and solvent may wholly or partially evaporate due to the decrease in pressure.

The formulation may be administered in other ways depending on whether local or systemic treatment is desired, and on the area to be treated. Administration may be topically, orally, by inhalation, or parenterally. The formulations are administered in dosages sufficient to inhibit expression of the target gene. The formulation may be administered once daily, or the EGS may be administered as two, three, four, five, six or more sub-doses at appropriate intervals throughout the day. In that case, the EGS contained in each sub-dose must be correspondingly smaller in order to achieve the total daily dosage. The dosage unit can also be compounded for delivery over several days, e.g., using a conventional sustained release formulation which provides sustained release of the EGS over a several day period. Sustained release formulations are well known in the art. In this embodiment, the dosage unit contains a corresponding multiple of the daily dose.

One of skill in the art will appreciate that certain factors may influence the dosage and timing required to effectively treat a subject, including but not limited to the severity of the disease or disorder, previous treatments, the general health and/or age of the subject, and other diseases present. Treatment of a subject with a therapeutically effective amount of a composition can include a single treatment or a series of treatments. Estimates of effective dosages and in vivo half-lives for the individual EGSs can be made using conventional methodologies or on the basis of in vivo testing using an appropriate animal model, as described elsewhere herein.

There are a variety of mouse models for the study of various human diseases. An albumin sensitization protocol has been developed for mice in which asthma-like pathology is induced in the murine lung by intra-peritoneal injection and subsequent nebulized bovine serum albumin (BSA). A transgenic mouse that over-expresses either IL-4 or IL-13 or other cytokines using a lung specific Clara-cell promoter regulated by levels of doxycycline can be used to simulate IL-4 and/or IL-13 dependent diseases. Mouse repositories can be found at: The Jackson Laboratory, Charles River Laboratories, Taconic, Harlan, Mutant Mouse Regional Resource Centers (MMRRC) National Network and at the European Mouse Mutant Archive. Such models may be used for in vivo testing of EGS, as well as for determining a therapeutically effective dose. Concentrations of 0 (negative control) 0.5, 1, and 10 and 50 µMolar should be sufficient to determine whether EGS are taken up by cells and functional in the murine lung using confocal microscopy. Variables to be assessed will include presence of absence of toxic effects, cell types with evidence of EGS uptake, dependence on lipid carriers such as Lipofectin and Lipofectase, and functional effects using co-staining of cells with a monoclonal antibody recognizing the murine interleukin-4 receptor α chain and or in situ cDNA hybridization. Mice will be nebulized and sacrificed for analysis at a range of time points after treatment spanning 1 to 24 hours, with 12 hour as an initial time point. Pathology in these animals after therapy with EGS and suitable controls will be determined through staining of murine lungs and other tissues post-mortem.

The efficacy of treatment can be monitored by measuring the amount of the target gene mRNA (e.g. using real time PCR) or the amount of polypeptide encoded by the target gene mRNA (Western blot analysis). The efficacy of treatment can also be determined by methods known to one of ordinary skill in the art with respect to the effect the EGS has on the symptoms of the disease to be treated.

EGS can be administered directly to humans or animal hosts for prophylaxis and therapy of influenza. For example, EGS could be fed to host poultry to provide passive resistance to pandemic strains since influenza replicates in the digestive tracts of poultry rather than in the respiratory tracts. Also, EGS can be expressed in plants for feeding to both animals and humans as both antiviral agents and imunomodulatory agents for therapy of asthma and other respiratory illness in addition to inhalation therapy of EGS. Topical therapy of atopic diseases such as eczema in early childhood targeting the key TH2 cytokines IL4 and IL13 may also prevent or delay the so called atopic march or progression noted from eczema to allergic rhinitis to asthma. The emerging pandemics predicted for influenza virus and the emerging epidemic of asthma and related atopic diseases provide a unique opportunity for application of improved technology to human respiratory diseases.

EGS can also be administered directly to humans or animal hosts for prophylaxis and therapy of asthma in humans including topical therapy of atopic diseases such as eczema in early childhood targeting the key TH2 cytokines IL4 and IL13 which may also prevent or delay the so called atopic march or progression noted from eczema to allergic rhinitis to asthma. Topical rather than systemic administration of EGS would maximize therapeutic index by minimizing effects in cytokine signaling. Similarly, early intra-nasal topical therapy of allergic rhinitis with EGS directed against TH2 cytokines can be used to prevent or delay onset of asthma in children or adults at risk. Therapy of food allergy or TH2 cytokine mediated inflammatory diseases of the digestive tract can be used via oral administration of EGS against inflammatory cytokines and receptors.

EGS and appropriate controls can be instilled into the nasal passage of live mice as a model of efficacy and pharmacokinetics of EGS in the reduction of asthma-like inflammation. Concentration of EGS will be determined empirically to approximate 1 micromolar in pulmonary fluids, which previous studies demonstrate is optimal for gene targeting in vitro. Pulmonary inflammation and asthma-like pathology can be induced in experimental induced model of asthma due to constitutive over-expression of IL-4 and IL13 and these mice can be obtained (Elias, *Chest* 126(2 Suppl.:111S-116S (2004)). Selected RNAi are designed against comparable targets such as the common IL4/13 receptor and the Stat6 transcription factor and RNAi off targeting will be determined for comparison to EGS. Murine models of cancer, lupus and diabetes prone states as well as altered physiologic states such as pregnancy and infection with other respiratory viral infections such as RSV (Respiratory Syncitial Virus), and intestinal parasite infections can also be utilized to look for altered metabolism, tissue distribution, off targeting or other pathology revealed by co-morbid states.

Similarly to EGS targeting the IL4 common chain, EGS targeting STAT-6 have been designed based upon proximity to the STAT-6 start site which has proven in other targets to be accessible to EGS and a match to the EGS consensus GNNNNNU as shown in Table 1. Organ specific cDNA libraries and purified cellular proteins obtained from mice can be analyzed for evidence of non-specific gene targeting effects, inflammation through Toll receptors or activation of cellular apoptosis pathways through p53/p21. This analysis will utilize a combination of gene chips for analysis of off targeting effects, specific PCR of relevant genes, Northern and Western blotting of whole proteins and or/EMSA of Nuclear protein extracts to look for altered expression or function of key regulatory proteins and transcription factors such as p21 and NF-κB.

Gene chip whole genome screens are readily available which examine off targeting effects at the transcriptional level of virtually the entire transcriptosome (more than 20,000 expressed sequence tags and controls, Affymetrix, Santa Clara, Calif.). Specific gene chips for 100-150 inflammatory cytokines and receptors (OligoGEArray, Superarray Bioscience, Frederick Mass.) and approximately 250 cellular apoptosis and developmental genes known to be altered by RNAi (DualChip, Eppendorf) are available. Custom DNA chips can also be designed. It is expected that EGS will have less non-specific effects and less non-specific inflammatory effects than comparable gene targeting with RNAi or conventional antisense DNA. The reason for this expectations is that 1) EGS are significantly smaller than comparable RNAi (32 modified RNA nucleotides for typical nuclease resistant EGS vs. 21-23 nucleotide double strand=42-46 total nucleotide RNAi), 2) EGS have significantly less double stranded RNA than RNAi, which is capable of triggering toll-3 innate immune receptors 3) EGS do not have DNA CpG motifs present in DNA based anti-sense, which is capable of triggering toll-9 innate immune receptors 4) EGS are based on activation of RNAse P, a housekeeping enzyme not induced or regulating the host anti-viral response in contrast to RNAi activated RISC and double strand DNA activated RNAse H. RISC and RNAse H are both members of a common recombinase pathway regulated by viral and other inflammatory signals.

Stability and quantitative tissue distribution of retained EGS are assessed by sequence analysis of EGS recovered from tissues using PCR with primers specific for the 5' and 3' termini of EGS and Northern blotting using EGS sequences. Evidence of integration of EGS into the host genome will be detected if present using PCR of genomic DNA with one primer specific for EGS and a second for host repetitive sequences and southern blotting of whole chromosomes separated by pulsed field electrophoresis and probed with labeled EGS.

Human epithelial and lymphoblastoid cell lines will be transfected with anti-asthma EGS, selected RNAi and other relevant control molecules. A number of characterized human IL4 and IL13 responsive cell epithelial cell lines are available both from the ATCC (American Type Culture Collection) and Dr. Elias that are responsive to IL4/IL13 and other inflammatory cytokines, while the human Jurkat human T-lymphoblastoid and Ramos B-lymphoblastoid cell lines responsive to IL4 and other lymphokines are available in the lab of Dr. Fuleihan2. These experiments will be conducted initially in the laboratory of Dr. Fuleihan by Drs. Fuleihan and his staff or by Dr. Dreyfus as part of an ongoing academic collaboration between Drs Dreyfus and Fuleihan2. Additional institutional agreements will be negotiated by Dr. Dreyfus on behalf of Keren and Dr. Fuleihan and the Yale Department of Pediatrics and Yale Office of grants and contracts as needed to conduct this research in collaboration with Keren staff including Dr. Smicun.

Human cells will be processed to obtain cDNA and evidence of off targeting will be determined using gene chips and other techniques known to one of skill in the art, as well as highly sensitive culture based assays for human inflammatory cytokine production at the protein level (Elispot, Cell Sciences, Canton, Mass.). Transfection will utilize lipid carriers including both carriers designed for experimental transfection of cells with nucleic acids as well as synthetic human pulmonary surfactant (Exosurf) to mimic uptake of EGS in the lung. Stability of EGS and RNAi will be determined by quantitative PCR using EGS and RNAi specific primers and other techniques such as Northern blotting of EGS specific RNA.

Thus stability and off targeting of EGS can be approximated in a model of both human unstimulated epithelial and hematopoetic cells as well as in cells in an inflammatory state induced by IL4 and IL13 and other inflammatory cytokines. Effects of EGS on cell viability, apoptosis and stability of EGS will be established in these human cell lines by PCR, Northern and Western Blotting quantitation of viral gene expression and other sensitive measures in both non-inflammatory and inflammatory cell states.

For mice studies, mice are exposed to allergic sensitizers in a murine model of asthma to determine whether blocking IL4/IL13 and other asthma related signaling molecules is sufficient to block development of an asthma-like state. A mouse model of the effects of asthma and IL4/IL13 on hematopoetic and non-hematopoetic cells in the murine lung has been developed (Kelly-Welch, et al., *J. Immunol.* 172(7): 4545-4555 (2004)) that can be used to study EGS targeting asthma inflammatory cytokines such as IL4/IL13.

IV. Diseases to be Treated

The formulations are administered in an effective amount to a patient in need of treatment or prophylaxis of inflammatory or related diseases to inhibit or reduce one or more symptoms of the disease or disorder. The formulations can be administered to animals or humans. As generally used herein, an "effective amount" of an EGS of the invention is that amount which is able to treat one or more symptoms of an inflammatory or related disease, reverse the progression of one or more symptoms of inflammatory or related disease, halt the progression of one or more symptoms of inflammatory or related disease, or prevent the occurrence of one or more symptoms of inflammatory or related disease in a subject to whom the compound or therapeutic agent is administered, as compared to a matched subject not receiving the compound or therapeutic agent. The actual effective amounts of drug can vary according to the specific drug or combination thereof being utilized, the particular composition formulated, the mode of administration, and the age, weight, condition of the patient, and severity of the symptoms or condition being treated. Dosages for a particular patient can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. In preferred embodiments, the inflammatory disease is asthma, allergic rhinitis, food allergies, atopic skin disease such as eczema, IL-4 and/or IL-13 dependent malignancies, IL-4 and/or IL-13 dependent autoimmune diseases, atopic diseases, and diseases caused by IL-4 dependent replication of viruses such as HIV-1 and Epstein-Barr virus.

Atopic diseases such as asthma, allergic rhinitis, food allergies, anaphylaxis and eczema result from a complex interplay between environmental factors and genetic factors (Vercelli, et al., *Int. Arch. Allergy Immunol.* 124:20-24 (2001) and Patino and Martinez, *Allergy* 56:279-286 (2001)). Infants at risk for asthma and other atopic diseases demonstrate increased expression of Immunoglobulin E (IgE) and increased numbers of peripheral eosinophils (Martinez, et al., *N. Engl. J. Med.* 332:133-138 (1995)), reflecting increased expression of cytokines such as interleukin-4 (IL-4) and 13 (IL-13), denoted TH2 (T Helper 2) cytokines, and relatively decreased expression of cytokines such as interferon g and interleukin-12 (IL-12), denoted TH1 (T Helper 1) cytokines (Wills-Karp, et al., *Nat. Rev. Immunol.* 1:69-75 (2001)).

A current paradigm proposes that atopic diseases result from an imbalance in cytokine expression with increased expression of TH2 cytokines and relatively decreased expression of TH 1 cytokines imprinted in infancy or early childhood (Patino and Martinez, *Allergy* 56:279-286 (2001)). In support of this paradigm, therapies directed at restoring cytokine balance in early childhood can ameliorate or even prevent atopic disease (Kalliomaki, et al., *Lancet* 357:1076-1079 (2001) and Murch, *Lancet* 357:1057-1059 (2001)). Potent antihistamines or other anti-inflammatory medications given to children at risk for asthma significantly delayed the incidence of subsequent asthma in children with IgE-mediated allergy, apparently by preventing histamine and proallergic cytokine release from degranulation of mast cells (Anoymous, *Pediatr. Allergy Immunol.* 9:116-124 (1998); Moller, et al., *J. Allergy Clin. Immunol.* 109:251-256 (2002); and de Longueville, *Pediatr. Allergy Immunol.* 11(Suppl. 13): 41-44 (2000)).

The cellular receptors for IL-4 and IL-13 share a common subunit termed the IL-4 receptor $\alpha$ chain, but differ in subunit shared with the IL-4 receptor $\alpha$ chain (Keegan, et al., *PNAS USA* 92:7681-7685 (1995) and Gessner and Rollinghoff, *Immunobiology* 201:285-307 (2000)). Because of receptor sharing, IL-4 and IL-13 share some common effects on target cells including promotion of IgE synthesis and eosinophil survival, but also different effects upon other target cells. For example, IL-4 receptors but not IL-13 receptors are readily detected on the surface of T lymphocytes although IL-13 receptors may nonetheless be expressed intra-cellularly (Graber, et al., *Eur. J. Immuno.* 28:4286-4298 (1998)). Conversely, IL-13 but not IL-4 expression seems to promote changes in epithelial tissue architecture and mucous expression in the lung (Kuperman, et al., *Nat. Med.* 8:885-889 (2002) and Wills-Karp, et al., *Science* 282:2258-2261 (1998). In humans, mutations in the shared IL-4 receptor $\alpha$ chain are associated with atopic disease, although not in all populations studied (Hackstein, et al., *Immunogenetics* 53:264-269 (2001); Hall, *Respir. Res.* 1:6-8 (2000); Hershey, et al., *N. Engl. J. Med.* 337:1720-1725 (1997); Howard, et al., *Am. J. Hum. Genet.* 70:230-236 (2002); Karp and Wills-Karp, *Microbes Infect.* 3:109-119 (2001); Mitsuyasu, et al., *Nat. Genet.* 19:119-120 (1998); Olavesen, et al., *Immunogentics* 51:1-7 (2000); and Risma, et al., *J. Immunol.* 169:1604-1610 (2002)). In murine models knockout of the IL-4 receptor shared IL-4 receptor $\alpha$ chain and knockouts of the IL-4 receptor activated STAT-6 signaling factor almost completely eliminate the allergic phenotype although some atopic response can be rescued with prolonged allergic stimulation (Gessner and Rollinghoff, *Immunobiology* 201:285-307 (2000); Grunewald, et al., *Int Arch Allergy Immunol* 125: 322-8 (2001); Nelms, et al., *Annu Rev Immunoll* 7:701-38 (1999); Noben-Trauth, et al., *Proc Natl Acad Sci USA* 94:10838-43 (1997); Noben-Trauth, et al., *Eur J Immunol* 32:1428-33 (2002); Quelle, et al., *Mol Cell Biol* 15:3336-43 (1995); Shimoda, et al., *Nature* 380:630-3 (1996); So, et al., *FEBS Lett* 518:53-9 (2002); and Zhu, et al., *J Immunol* 166: 7276-81 (2001)). Selective blockade of the IL-4/IL-13 receptor with a mutated IL-4 competitive peptide antagonist also blocked allergic sensitization in the mouse (Tomkinson, et al., *J. Immunol.* 166:5792-5800 (2001)).

These observations illustrate the importance of the IL-4/IL-13 signaling pathway as a target for pharmacologic intervention to prevent or treat allergic diseases. This application describes a novel strategy to target IL-4 and IL-13-mediated gene expression by inactivation of the receptors for these cytokines using catalytic RNA termed external guide sequences (EGS) (Gopalan, et al., *J Biol Chem* 277:6759-62 (2002); Guerrier-Takada, et al., *Methods Enzymol* 313:442-56 (2000); Plehn-Dujowich, et al., *Proc Natl Acad Sci USA* 95: 7327-32 (1998); and Rosenwasser, et al., *Am J Respir Crit Care Med* 156:S152-5 (1997)). EGS and the recently discovered phenomena of RNA interference or RNAi (Plasterk, *Science* 296:1263-1265 (2002)) utilize small RNA molecules introduced into eukaryotic cells to inactivate a particular target RNA. Small catalytic RNA targeting the IL-4/IL-13 pathway might be selectively introduced into pulmonary tissues using endogenous lung surfactants as previously described with conventional antisense DNA termed RASONS (Nyce and Metzger, *Nature* 385:721-725 (1997); Sandrasagra, et al., *Antisense Nucleic acid Drug Dev.* 12:177-181 (2002); and Finotto, et al., *J. Exp. Med.* 193:1247-1260 (2001)). Targeted inactivation of the IL-4 receptor α chain could provide a means of modulating the combined pathogenic effects of IL-4 and IL-13 with a single therapeutic agent. Importantly, eliminating receptor expression would modulate autocrine and paracrine signaling (signaling between the cell and itself or cells in close contact) as well as signaling through soluble cytokine release.

A number of applications of molecules in therapy of allergic and autoimmune diseases and asthma based on the use of these molecules to decrease expression of the functional IL-4 receptor α chain in vivo. Knockout of the shared IL-4 receptor α chain required for both IL-4 and IL-13 eliminated both IgE production and asthma-like lung pathology suggest a unique role for IL-13 in asthma and some atopic skin diseases (Wills-Karp, et al., *Science* 282:2258-2261 (1998); Wills-Karp, *Respir. Res.* 1: 19-23 (2000); and Herrick, et al., *Clin. Invest.* 105:765-775 (2000)). A recent clinical trial of a soluble fragment of the human shared IL-4 receptor α chain capable of binding IL-4 (but not IL-13) showed some effectiveness in severe asthmatics (Steinke and Borish, *Respir. Res.* 2:66-70 (2002)). Importantly, no adverse effects related to loss of IL-4 function were noted in the lung or systemically in these human subjects.

IL-4 and IL-13 are also required for systemic immunity to some bacterial and parasitic infections (Karp and Wills-Karp, *Microbes Infect.* 3:109-119 (2001); Mountford, et al., *Infect. Immun.* 69:228-236 (2001); and Mohrs, et al., *J. Immunol.* 162:7302-7308 (1999)), and receptor inactivation could result in increased infections in targeted tissues. Targeted inactivation of the IL-4 receptor α chain to particular tissues such as lung or other tissues such as the digestive tract where polymorphisms of the IL-4 receptor are associated with inflammatory bowel disease (Klein, et al., *Genes Immun.* 2:287-289 (2001)) could be of benefit to prevent systemic immunodeficiency. Systemic immuno-modulation via targeted inactivation of the IL-4 receptor α chain might also be of benefit under some circumstances since loss of the IL-4/IL-13 receptor prevents the onset of systemic autoimmune diabetes in the mouse (Grossman and Paul, *Curr. Opin. Immunol.* 13:687-698 (2001) and Radu, et al., *PNAS USA* 97:12700-12704 (2000) and some tumors are also responsive to IL-4 Strome, et al., *Clin. Cancer Res.* 8:281-286 (2002); Essner, et al., *J. Gastrointest. Surg.* 5:81-90 (2001); and terabe, et al., *Nat. Immunol.* 1:515-520 (2000)). IL4 has also been shown to differentially modulate HIV1 replication in primary cells of the monocyte/macrophage lineage. The imbalance of IL4/IL13 TH2 cytokines over TH1 cytokines is thought to facilitate replication of viruses including the HIV-1 and Epstein-Barr virus.

In one embodiment, the formulation is administered to a patient with allergic rhinitis or asthma by topical nasal application and/or inhalation. In another embodiment, the formulations are administered to a patient with a food allergy by injection or oral administration so that the formulation is absorbed by intestinal cells. In another embodiment, the formulation is applied topically to the skin to a patient with an atopic skin disease such as eczema. In another embodiment, the formulation is administered systemically to a patient with an IL-4 and/or IL-13 dependent malignancy. In another embodiment, the formulation is administered systemically to a patient with an IL-4 and/or IL-13 autoimmune disease. In another embodiment, the formulation is administered to a patient with an IL-4 and/or IL-13 autoimmune disease by targeting cells undergoing IL-4 dependent receptor editing due to IL-4 dependent expression of RAG genes. In another embodiment, the formulation is administered to a patient for treatment of IL-4 dependent replication of viruses such as HIV-1, Epstein-Barr, and the Influenza virus.

EXAMPLES

Example 1

EGS Targeting Human Interleukin-4 Receptor α mRNA

Small nuclease resistant EGS are designed against a conserved target in the human transcriptosome relevant to allergic inflammation. EGS expressed transiently in cells from a plasmid vector demonstrated that the human IL4 receptor chain shared a subunit with the IL13 receptor termed IL4Rα required for allergic inflammation. This example demonstrates IL4Rα can be targeted most effectively with an EGS expressed in cells that binds to underlined sequences in proximity to the IL4Rα start site (AUG start codon shown in italics) A*UG*GGGUGGCUUUGCUCUG (SEQ ID NO:2) and that IL4Rα can be targeted in vivo.

Materials and Methods

Restriction enzymes and other enzymes used in this work were obtained from New England Biolabs, Beverly Mass. unless specified. DNA sequences were determined with Sequenase, United States Biologicals, Cleveland, Ohio. Biochemicals were obtained from Sigma, St. Louis, Mo. Oligonucleotides were synthesized at the Keck facility, Yale Department of Molecular and Cellular Biology, New Haven, Conn. Radioactive nucleotides were obtained from Amersham, Piscataway, N.J. Plasmids were prepared and restriction fragments isolated using Quiagen reagents, (Valencia, Calif.).

Primers, Targeting Sequences and Oligonucleotides

For isolation of mRNA and cDNA from primary human lymphocytes, oligonucleotide primers denoted IL-4r5001 (5'agatcaggagttcgagacc (SEQ ID NO:104)) and IL-4r3002 (5'-gttttcactccaaatgttgac (SEQ ID NO:105)) define a predicted 544-bp fragment which spans IL-4 receptor α chain nucleotides 133 to 676 including the start site of the receptor protein at nucleotide 176. A HincII restriction enzyme site in the IL-4 receptor α chain sequence was included in the IL-4r3002 primer (underlined in IL-4r3002 sequence shown) to facilitate further analysis of the cloned DNA fragment.

A 544-bp fragment was amplified by PCR (AmpliTaq polymerase, Perkin-Elmer Cetus, Norwalk, Conn.) from primary human lymphocyte cDNA using a hybridization temperature of 56° C., and 30 amplification cycles. Amplified DNA was directly cloned into the vector pCR2.1 topo (Invitrogen, Carlsbad, Calif.) using topoisomerase. cDNA in a plasmid denoted pIL-4r1 was fully sequenced and shown to contain cDNA corresponding to the predicted IL-4r sequence in the sense orientation relative to a T7 polymerase transcription site in pCR2.1 topo. 2.3.

T1 Mapping of mRNA Transcript

The pCR2.1 vector T7 polymerase start site is positioned to express a portion of the sense transcript of IL-4 receptor α chain mRNA in pIL-4r1 spanning the mRNA translation start site. The predicted transcript includes 72 additional nucleotides of 5' leader sequence from the pCR2.1 vector linker. pIL-4r1 linearized with HincII incubated with T7 polymerase generated a predicted 616 nt mRNA (72 nt leader sequence and 544 nt cloned mRNA). This RNA was treated with RNAse-free DNAse to remove DNA template and transcribed RNA was dephosphorylated with Calf Intestinal Phosphatase (CIP). CIP was inactivated by heat treatment, and RNA was purified further by phenol extraction and ethanol precipitation. RNA was then resuspended and 5' end-labeled with T4 Polynucleotide Kinase using g32P labeled ATP. Full-length labeled RNA was purified using a 6% preparative gel and digested partially with RNAse T1 as described previously (Guerrier-Takada and Altman, *Methods Enzymol*. 313:442-456 (2000); and Plehn-Dujowich and Altman, *PNAS USA* 95:7327-7332 (1998)) using a partial base digestion ladder of the RNA as a size standard. T1 nuclease sensitive sites were identified by gel electrophoresis of partial digestion products. The labeled mRNA was digested with T1 nuclease and digestion fragments separated on a 12% and 8% sequencing gel. In this analysis, a T1 sensitive site is detected as a dark band due to cleavage of the end labeled mRNA at the site. Sequences are flanked by a ladder of fragments differing in one base increments generated by alkaline degradation of the RNA to permit localization of T1 sensitive sites. A T1 sensitive site corresponds to the junction of 3' linker sequences and 5' mRNA. All G residues in the linker sequence (migrating bellows fragment A) were highly sensitive to T1. A T1 sensitive site denoted B corresponds to G residues in proximity to the AUG start site of the mRNA subsequently targeted by EGS1. Full-length (undigested) mRNA denoted C is visible at the top of the 8% gel.

For design and synthesis of candidate EGS sequences, two T1 nuclease sensitive sites were selected for further study as targets for cleavage by EGS termed EGS1 and EGS2 as described in the text.

EGS1 and EGS2 were transcribed using T7 RNA polymerase and DNA templates generated by PCR amplification of a cloned wild type tyrosine tRNA cDNA (pTyr). Oligonucleotides EGS501 5'-taatacgactcactatagctgcagag-caagcagactctaaatc (SEQ ID NO:94) and EGS301 5'-aagctt-taaaaatggtgggtggcgaaggattcgaacc (SEQ ID NO:95) were used to generate EGS1 template and EGS502 5'-taatacgact-cactatagctgcagcctgagcagactctaaatc (SEQ ID NO:96) and EGS302 5'-aagctttaaaaatggtgtcctgcgaaggattcgaacc (SEQ ID NO:97) EGS2, respectively. Terminal phosphate 5' phosphates were added to oligonucleotides using T4 Polynucleotide Kinase prior to PCR to facilitate blunt end cloning of amplification products. PCR was performed with AmpliTaq polymerase (Stratagene) and Epicentre Failsafe PCR premix buffer H (Epicentre, Madison, Wis.) with eight amplification cycles at a hybridization temperature of 37° C. and then 30 additional cycles at a hybridization temperature of 72° C.

After gel purification, EGS1 and EGS2 were subcloned by blunt ended ligation into the HincII site of pUC19 and nucleotide sequence confirmed. Plasmid containing EGS1 template was denoted pEGS1.1, and plasmid containing EGS2 was denoted pEGS2.1. Prior to transcription with T7 polymerase, these plasmids were linearized with restriction enzyme DraI cleaving a DraI site located at the 3' end of the EGS templates. DNA templates were removed by digestion with RNAse-free DNAse, and RNA transcripts of predicted size were evident without degradation when viewed on 3% ethidium stained agarose gels prior to incubation with target RNA.

For in vitro cleavage assay of mRNA transcript by candidate EGS, pIL-4r1.1 linearized with restriction enzyme FokI, at an internal site in the 544 nt cloned cDNA, was incubated with T7 RNA polymerase in the presence of ap32 ATP to generate a labeled target 399 nt RNA. This ap32 ATP-labeled 399 nt RNA contains IL-4r mRNA nucleotides 133 to 459 with 72 additional nucleotides of pCR2.1 topo leader sequence. Target RNA was gel purified on a 6% preparative sequencing gel and incubated with purified EGS in PA buffer (Guerrier-Takada and Altman, *Methods Enzymol*. 313:442-456 (2000); and Plehn-Dujowich and Altman, *PNAS USA* 95:7327-7332 (1998)). RNAse P was obtained from Dr. S. Altman, Yale MCDB, New Haven, Conn. Following incubation with EGS for 30V target mRNA was separated on a 6% sequencing gel, fixed and dried, and visualized by autoradiography.

For construction of in vivo expression plasmids for full-length EGS1 and anti-codon deleted human and murine EGS1, EGS sequences were excised from pEGS1.1 using HindIII and PstI and ligated into HindIII/PstI digested plasmid pMU6. pEGS1.1 contains full-length EGS1. Additional plasmids containing EGS-like sequences but lacking anti-codon loops denoted phIL4Re1.1, phIL4Rmute1.1, pmIL4Re1.1 and pmIL4Rmute1.1 were generated by direct ligation of double-stranded synthetic oligonucleotides containing embedded HindIII and PstI "sticky ends" after annealing complementary sense (S) and antisense (A) oligonucleotides into HindIII/PstI-digested plasmid pMU6. These plasmids were to serve for both conventional antisense RNA effects as well as non-specific effects of doublestranded RNA upon the IL-4 promoter (Kehoe, et al., *J. Immunol*. 167(5): 2496-2510 (2001). These additional EGS had a deleted anti-codon loop to facilitate cloning into expression vector with— D. H. Dreyfus et al. International Immunopharmacology 4 (2004) 1015-1027, out PCR used to generate full-length pEGS1.1. Deletion of anti-codon loop from other EGS has been found to increase the efficiency of RNAse P cleavage reactions without effects upon specificity, while mutation of the T loop eliminates RNAse P cleavage but not conventional antisense effects or non-specific effects of EGS RNA expression. All plasmid nucleotide sequences were confirmed after cloning into pMU6.

For in vivo assay of EGS, B-lymphoblastoid cell lines used in in vivo studies were cultured in RPMI 10% FCS supplemented with glutamine, penicillin and streptomycin. 45-2w11 cells were derived from m12-4-1 murine lymphoblastoid cells through stable transfection with a functional human IL-4 receptor α chain mRNA expression plasmid, expression of both murine and human IL-4 receptor α chain mRNA was confirmed by PCR in these cells. Human B-lymphoblastoid Ramos cells previously shown responsive to human IL-4. For each experiment, approximately $10^5$ exponentially growing cells were transfected with reporter plasmids and EGS encoding plasmids using electroporation at 950 AF, 186 V, 250 V. Human IL4 reporter gene containing the human IL4 5' sequences fused to luciferase in Plasmid PGL-2 (Promega) (Georas, et al., *Blood* 92:4529-4538 (1998)). NFnB luciferase reporter contains multiple copies of a consensus response site fused to luciferase reporter plasmid PGL-2 (Promega, Madison, Wis.). Cells were transfected with plasmids as described and incubated for 40 h at 37° C., then additional reagents ionomycin (500 nm), PMA (25 ng/Al), and/or human IL-4 (10 ng/Al) were added to the medium and cells were incubated for an additional 8 h at 37° C. Cells were frozen after removal of supernatant and thawed for luciferase assay on approximately $2.5 \times 10^4$ cells (one quarter of total transfected cells) either single or dual luciferase assay (Promega) using manufacturers suggested conditions.

Cells for experiments using dual luciferase assay were also transfected with 10 ng of pRL/SV40 expressing *Renilla* Luciferase under control of an SV40 promoter. Results in Dual and Single Luciferase assays were similar.

Luciferase data are expressed as arbitrary luciferase units derived by subtracting background from observed luciferase activity measured over a 60-s interval. For graphic representation, NFnB luciferase reporter luciferase units were divided by a factor of 10 to facilitate comparison with IL-4 reporter results.

Data were analyzed using Student's T test with four independent experiments used to generate each data point shown.

Results

T1 Nuclease Mapping of Human Interleukin-4 Receptor a mRNA.

Partial digestion of the receptor mRNA with T1 nuclease indicated that significant mRNA secondary structure was present in the first several hundred nucleotides of the mRNA (see FIG. 2). RNAse T1 cleaves RNA after guanine (G) residues of the RNA that are exposed in solution and single-stranded, but not after G residues that are buried in the RNA secondary structure or base paired into double-stranded regions.

Partial digestion fragments form a ladder after size fractionation by gel-electrophoresis of reaction products in which dark bands represent open sites in the target RNA while absent bands represent noncleaved regions de to secondary structures. To determine the exact nucleotide position of sensitive sites, a ladder of base digested target RNA with each nucleotide position present is electrophoresed alongside the target mRNA ladder.

Many G residues in the human interleukin-4 receptor a mRNA were not at all accessible to T1. Notably, T1 sensitive sites in the human interleukin-4 receptor a mRNA were relatively clustered in the 5' region of the mRNA in the vicinity of the mRNA start codon (see FIG. 2). In contrast, all G residues in the pCR2.1 leader fused to the target mRNA 5' region were cleaved and formed dark bands as would be expected for a synthetic sequence without predicted secondary structures. The functional significance of human interleukin-4 receptor a mRNA secondary structure could correspond to binding sites for regulatory factors.

Synthesis In Vitro of EGS Targeting Sites within Human Interleukin-4 Receptor α mRNA.

T1 mapping of the human IL-4r mRNA revealed several sites near the start site if the mRNA matching the RNAse P consensus GNNNNNU that were accessible to RNAse T1 and thus apparently in single-stranded conformation (see FIG. 2). EGS denoted EGS1 and EGS2 designed to form structures resembling precursors to a human tRNA when bound to human interleukin-4 receptor α mRNA (FIG. 3B) based upon standard Watson-Crick base pairing. Oligonucleotide primers denoted EGS501 and EGS301 were used to generate EGS1 cDNA and oligonucleotides EGS502 and EGS302 were used to generate EGS2 cDNA by PCR from a human tyrosine tRNA cDNA. A promoter for T7 RNA polymerase was fused to the 5' region of the EGS cDNA in order to express the EGS in vitro. A PstI site in E501 and 502 and a HindIII site in E301 and 302 (see FIG. 3b) were included for subsequent EGS subcloning into in vivo expression vectors. EGS301 and EGS302 also contained DraI restriction sites for blunt end linearization of the plasmid at the 3' terminus of the EGS cDNA to terminate in vitro T7 transcription. The modified DraI site can also serve as a terminator sequence in vivo studies since it resembles a transcription termination site for RNA polymerase III.

Characterization of EGS in an In Vitro Assay of RNAse P-dependent Substrate Cleavage.

An assay for site-specific cleavage of human interleukin-4 receptor a mRNA was prepared by end labeling and purifying a defined 32P labeled fragment of the human interleukin-4 receptor a mRNA transcribed from pIL-4R.1. The labeled mRNA fragment and purified EGS RNA was incubated with the presence of purified RNAse P under conditions described previously (Plehn-Dujowich and Altman, *PNAS USA* 95:7327-7332 (1998). The purified human interleukin-4 receptor a mRNA transcript of 399 nt was noted to undergo site-specific RNAse P-mediated cleavage in vitro to yield predicted fragments of 119 and 280 nt, respectively, in the presence of EGS1EGS1. As a control for activity of RNAse P control-labeled tRNA denoted TsupS1 was also incubated with RNAse P under identical conditions to yield predicted fragments of 82 and 28 nt. Site-specific cleavage of IL-4 receptor α chain mRNA by EGS1 after incubation in PA buffer with RNAse P was show using radioactively labeled RNA substrate after gel electrophoresis (6% polyacrylamide/ 8M urea sequencing gel). A 119 nt 5' fragment of mRNA encoding IL-4 receptor α chain mRNA increases with increasing ratio of EGS1 molar ratio to target mRNA when incubated with a constant concentration of RNAse P. A 3' fragment is also evident although partly obscured by a comigrating background band.

Cleavage of human interleukin-4 receptor α mRNA was evident at the lowest molar ratio of EGS1 to target RNA (15 to 1 ratio). Cleavage was dependent upon concentration of EGS1 with apparent saturation of the reaction at approximately 1000:1 ratio of EGS to target. No cleavage of the target was detected with either EGS1 alone or RNAse P alone.

Figures 3A, 3B:
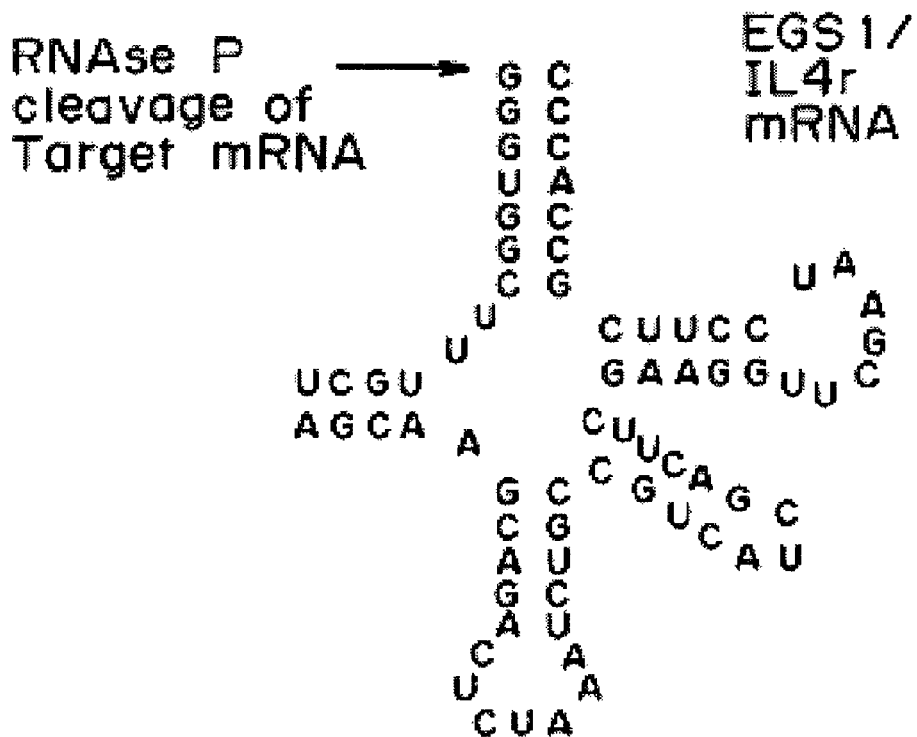
FIG. 3a is the predicted structure and cleavage site of EGS1 (SEQ ID NO:102) bound to human IL-4 receptor α chain mRNA (SEQ ID NO:103) with 5 and 3' complementary regions. These sequences are based upon conventional Watson-Crick base pairing rules but have not been demonstrated to occur in vitro or in vivo in this work.
FIG. 3b are the oligonucleotides EGS501 (SEQ ID NO:94) and EGS301 (SEQ ID NO:95) used to generate a template for in vitro transcription of EGS1 by PCR from pTyr, a plasmid containing human wild type tyrosine tRNA cDNA. Similar oligonucleotides EGS502 and EGS302 were used to generate a template for transcription of EGS2.

EGS2 was completely inactive in cleavage of the target at all concentrations shown at the level of detection of this assay although the EGS2 target site both lay within a T1 sensitive region of the target (see FIG. 2) and EGS2 could in theory base pair with IL-4r mRNA to form a tRNA-like structure (see FIG. 3b). Further analysis of the EGS2 sequence in vitro suggested that EGS2 could base pair with itself in addition to the target mRNA, possibly accounting for its inactivity.

For in vivo studies, the EGS1 sequence was cloned into a polymerase III expression plasmid denoted pMU6 in a plasmid denoted pEGS1.1. Cells transfected with pEGS11.1 showed similar transfection efficiency to the empty pMU6 vector and no evidence of toxicity since transfected cells expressed similar amounts of green fluorescent protein (GFP) in about 5-10% of cells as determined by cotransfection of a GFP expression vector. Since only 5-10% of cells were transfected, it was apparent that any changes in IL4 receptor mRNA or protein expression would be difficult to detect without cell sorting or construction of stable cell lines due to the presence of many untransfected cells. A luciferase-based assay of IL-4 receptor function that did not involve cell sorting or manipulations has been devised.

Figure 4A:
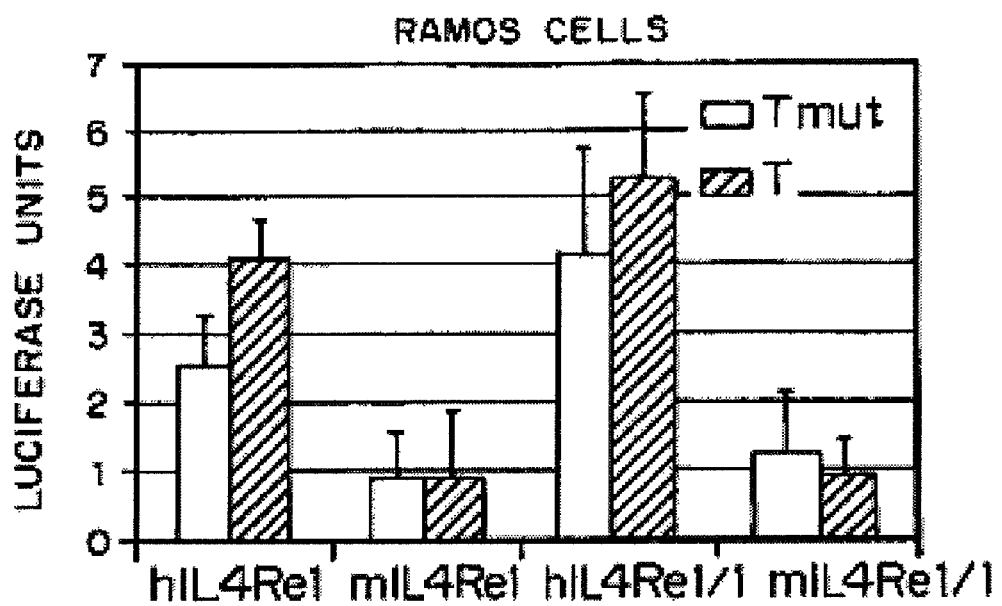
FIGS. 4a and 4b shows human Ramos and murine 45/2w11 cells exhibit RNAse Pdependent and IL-4-independent activation of IL-4 gene in presence of co-transfected EGS1 sequences, measured as luciferase units.

Others have demonstrated that the human IL-4 gene is negatively regulated by IL-4/Stat-6-mediated signaling. IL-4-activated Stat-6 binding to a site in the IL-4 gene competes with IL-4-independent activation of the gene by NF-AT (Georas, et al., *Blood* 92:4529-4538 1998). Therefore, luciferase expression from a human IL-4 reporter gene could serve as a measure of IL-4 receptor functional status with increased IL-4-independent IL-4 gene expression a marker for decreased IL4 receptor Stat-6 activation. As a measure of IL-4, responsive human Ramos lymphoblastoid cells were transfected with either EGS1 or control plasmids and incubated for 40 h followed by stimulation of cells with ionomycin or IL-4 for an additional 8-h period and then luciferase activity was determined. The initial 40-h incubation period was necessary to detect decreased function of receptor expected to occur over time due to EGS inactivation of the receptor mRNA. As shown in FIG. 4a, EGS1-related sequences transfected into human Ramos cells demonstrated that EGS sequences increased transcription of the IL-4 reporter gene. With ionomycin co-stimulation of cells, the overall dosedependent effects of EGS1.1 were similar although of greater magnitude than unstimulated cells.

To determine whether effects upon the IL-4 luciferase reporter were dependent upon both RNAse P and specific sequences in the EGS, it was necessary to construct in vivo expression plasmids with either a mutated T loop or murine sequences not complementary to human target mRNA.

Mutation of the EGS T loop (denoted Tmut) eliminates activity of RNAse P without altering conventional antisense effects of expressed complementary RNA. Altering the complementary sequences of the EGS to the murine sequence with a functional T loop controls for non-specific effects of the T loop or other vector sequences. As shown in FIG. 4a, activation of the IL-4 promoter in Ramos cells was in part dependent upon RNAse P and completely dependent upon specific sequences complementary to human interleukin-4 receptor a mRNA transcript.

Figure 4B:
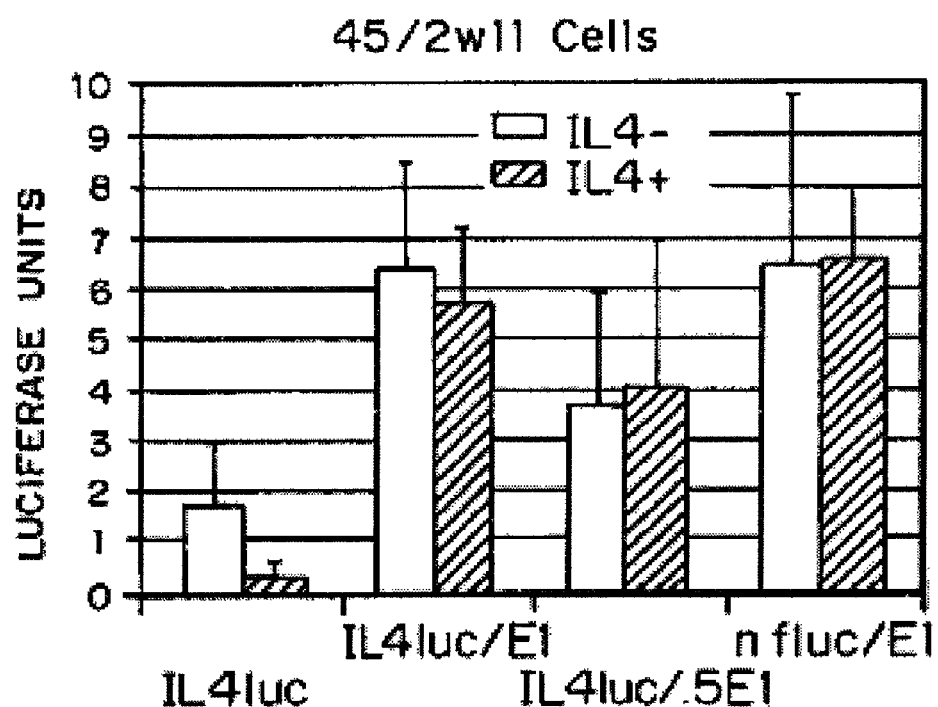

As expected, IL-4 decreased transcription of the human IL-4 promoter in Ramos cells (see FIG. 4a). Murine 2w11 cells with a transfected active human IL-4 reporter gene demonstrated that IL-4 gene expression was significantly increased with increasing amounts of co-transfected EGS1 expression plasmid both in the presence or absence of human IL-4 (see FIG. 4b). Similar results were evident in Ramos cells and in ionomycin or ionomycin PMA stimulated cells. In some experiments, cells were also transfected with a reporter gene for NF-κB, a luciferase reporter that is not directly regulated by IL-4 or ionmycin to determine the degree to which nonspecific effects of EGS were evident (see FIG. 4b). EGS1 co-transfection did not block activation of the NF-κB reporter, and both NF-nB reporter and IL-4 reporter gene responses were largely IL-4 independent in this assay (see FIG. 4b).

EGS capable of cleaving interleukin-4 receptor a mRNA are described. EGS1 expressed in vitro, directs efficient RNAse P-mediated cleavage of mRNA for the human IL-4r mRNA in vitro. The ability of EGS1 to catalyze RNAse P-mediated site-specific cleavage of mRNA demonstrates that a structure similar to that shown in FIG. 3 forms between EGS and target mRNA since RNAse P will not cleave unless such a structure is present. The inability of EGS2 to cleave target mRNA in vivo confirms that the complexities of base pairing between EGS and mRNA and/or RNAse P are sufficient that activity of an EGS cannot be assumed without additional in vivo or in vitro analysis.

Further support for in vivo activity of EGS1 was evident in an assay devised to determine whether EGS1 and related sequences were able to cause RNA P-dependent effects upon an IL-4 reporter gene. Since others have demonstrated that IL-4-mediated signaling in lymphoblastoid cells blocks IL-4-independent NF-AT-dependent activation of the IL-4 gene, it was hypothesized that inactivation of basal IL-4 signaling in lymphoblastoid cells would be evident as increased IL-4-independent transcription of an IL-4 luciferase gene. Results in two independent IL-4 responsive cell lines were consistent with results expected from inactivation of basal IL-4 receptor signaling, and were not consistent with non-specific effects such as cell death due to expression of EGS which would not be consistent with increased expression of a reporter gene (see FIGS. 4A and 4B). These results were also sequence dependent in vivo since they were not evident with an EGS targeting the murine interleukin-4 receptor α mRNA transcript that differs at only two nucleotides from the human within targeted sequences.

These experiments demonstrate that EGS1 and related sequences are a new class of reagents for modifying IL-4 and IL-13 signaling. EGS1 can be optimized for more effective cleavage of mRNA by, for example, deletion of the anticodon loop of the tRNA region of the EGS. EGS can be generated in eukaryotic cells by gene therapy with expression vectors or by epigenetic therapy with truncated nuclease resistant oligonucleotides. Stable transfection of cells with EGS expression vectors can lead to prolonged and possibly regulated inactivation of targeted mRNA, but can potentially cause oncogenic changes in cells. Epigenetic therapy with small nuclease resistant oligonucleotides has the advantage of targeting mRNA without a requirement for potentially oncogenic expression vectors.

Example 2

EGS Targeting Influenza Virus

Small nuclease resistant EGS were designed against a conserved target in the influenza transcriptosome (shown in Table 1). It has been shown that the influenza elongation factor EF-1 can be targeted most effectively with an EGS expressed from a retroviral vector that binds to underlined sequences in proximity to the EF-1 start site (AUG start codon shown in italics) AUGGAAAGAAUAAAAGAACUAAG (SEQ ID NO:93) (Plehn-Dujowich and Altman, *PNAS USA* 95:7327-7332 (1998)). EGS, EGS controls and fluorescein labeled EGS can be designed that are stable to digestion by nucleases and small enough to enter cells readily using substituted bases. Multiple similar targets in a least 4 conserved influenza genes have been identified (see Table 2). There is a high degree of target site conservation between influenza gene targets as described in genes from the H1N1 influenza strains circulating circa 1998, H1N1 strains circulating currently in the wild and H5N1 avian pandemic strains circulating currently. These data strongly suggest that an EGS effective against a target will be effective for a wide variety of influenza over prolonged intervals of time, in contrast to vaccines targeting rapidly mutating external viral proteins.

Organ specific cDNA libraries and purified cellular proteins obtained from mice and are analyzed for evidence of non-specific gene targeting effects, inflammation through Toll receptors or activation of cellular apoptosis pathways through p53/p21. This analysis uses a combination of gene chips for analysis of off targeting effects, specific PCR of relevant genes, Northern and Western blotting of whole proteins and or/EMSA of Nuclear protein extracts to look for altered expression or function of key regulatory proteins and transcription factors such as p21 and NF-κB. Gene chip whole genome screens are readily available which examine off targeting effects at the transcriptional level of virtually the entire transcriptosome (more than 20,000 expressed sequence tags and controls, Affymetrix, Santa Clara, Calif.) and are well known to one of ordinary skill in the art. Specific gene chips for 100-150 inflammatory cytokines and receptors (OligoGEArray, Superarray Bioscience, Frederick Mass.) and approximately 250 cellular apoptosis and developmental genes known to be altered by RNAi (DualChip, Eppendorf) are available. Custom DNA chips can also be designed and produced by (Affymetrix, Santa Clara, Calif.) or other techniques known to one of skill in the art.

Stability and quantitative tissue distribution of retained EGS are assessed by sequence analysis of EGS recovered from tissues or cells using PCR with primers specific for the 5' and 3' termini of EGS. Evidence of integration of EGS into the host genome can be determined using PCR of genomic DNA with one primer specific for EGS and a second for host repetitive sequences and southern blotting of whole chromosomes separated by pulsed field electrophoresis and probed with labeled EGS.

Stable human epithelial and lymphoblastoid cell lines can be transfected with anti-influenza EGS and relevant control molecules by methods known to one of ordinary skill in the art. Cells are processed to obtain cDNA and evidence of off targeting will be determined using gene chips and other techniques as described herein, as well as highly sensitive culture based assays for inflammatory cytokine production at the protein level (Elispot, Cell Sciences, Canton, Mass.). Transfection can utilize lipid carriers including both carriers designed for experimental transfection of cells with nucleic acids as well as synthetic human pulmonary surfactant (Exosurf) to mimic uptake of EGS in the lung. Stability of EGS and RNAi is determined by quantitative PCR using EGS and RNAi specific primers.

A number of characterized human IL4 and IL13 responsive cell epithelial cell lines are available both from the ATCC (American Type Culture Collection) that are responsive to IL4/IL13 and other inflammatory cytokines. Human Jurkat human T-lymphoblastoid and Ramos B-lymphoblastoid cell lines responsive to IL4 and other lymphokines are also available. Stability and off targeting of EGS can be approximated in a model of both human unstimulated epithelial and hematopoetic cells as well as in cells in an inflammatory state induced by IL4 and IL13 and other inflammatory cytokines such as would be present in the asthmatic lung, known to be at increased risk of influenza pathogenesis. Effects of EGS on viral replication and stability of EGS are established in these human cell lines by PCR, Northern and Western Blotting quantitation of viral gene expression and other sensitive measures in both non-inflammatory and inflammatory cell states known to one of ordinary skill in the art.

For in vivo analysis, EGS are administered intra-nasally in saline into the nasal passages of mice at a range of concentrations to achieve an intra-pulmonary concentration of 1 micromolar. EGS are administered first in the presence of sham infection with influenza, and if no significant pathology due to EGS is evident mice, are exposed to EGS and co-infected with influenza. Outcomes such as mortality, weight loss and recovery are used as measures of efficacy of EGS against influenza in vivo.

EGS and appropriate controls are instilled into the nasal passage of live mice and other animals as a model of effects and pharmacokinetics of EGS in the presence of co-morbid conditions. Murine models of altered physiologic states such as infection with other respiratory viral infections can also be utilized to look for altered metabolism, tissue distribution, off targeting or other pathology revealed by co-morbid states. Evidence of off targeting is determined using gene chips and other techniques as described for murine cells. Similar experiments can be performed in poultry (chicks or ducklings) which are the wild reservoir of influenza to determine metabolism of EGS in this alternative target of RNA enzyme therapy. Evidence of RNAi off targeting will be determined for comparison to EGS.

A model of the effects of asthma and IL4/IL13 on hematopoetic and non-hematopoetic cells in the murine lung has been described (Kelly-Welch, et al., *J. Immunol.* 172(7): 4545-4555 (2004)). EGS targeting asthma inflammatory cytokines such as IL4/IL13 has also been described (Dreyfus, et al., *Int. Immunopharmacol.* 4(8):1015-1027 (2004)). These models can be used to determine whether some of the pathogenesis of influenza can be blocked by EGS therapy to block IL4 and IL13. Influenza is a particular risk for patients with asthma and related inflammatory lung disease. Live attenuated vaccines for influenza are contraindicated in patients with asthma and patients with asthma may have exacerbation of asthma even after vaccination with conventional killed vaccines.

Small nuclease resistant EGS are described that target the human transcriptosome relevant to allergic inflammation and the influenza virus. Mice exposed to standard (non-pandemic) influenza prior to and after allergic sensitization to confirm that influenza, like other respiratory viruses causes increased asthma like pathology mediated through IL4/IL13 (Umetsu, *Nat. Med.* 10(3):232-234 (2004) and Dahl, et al., *Nat. Immunol.* 5(3):337-343 (2004)). Using these mouse models, EGS targeting IL4/13 are expected to be sufficient to block some of these pathogenic effects. These mouse models can also be used to determine whether combined therapy with EGS against IL4/13 and influenza genes is tolerated and effective, providing additional therapy for influenza in patients with asthma and related respiratory diseases. Organ specific tissue samples that are generated are used to prepare protein and cDNA libraries of asthmatic mice treated with EGS for further analysis. Preparation of organ and tissue samples for pathology studies and extraction of mRNA for preparation of cDNA libraries are performed using methods known to one or ordinary skill in the art.

For human studies, EGS for prophylaxis and/or therapy of influenza are given to healthy adult human volunteers of both sexes via either inhalation or nasal irrigation. EGS dosage and pharmokinetics of EGS are monitored by analysis of epithelial cells from saline sputum induction and hematopoetic cells obtained by phlebotomy as in both the murine model of influenza and asthma as well as human epithelial and lymphoblastoid cell lines. Primary epithelial cells obtained and monitored by saline sputum induction are secondarily infected with influenza in vitro to confirm efficacy of EGS in primary human cells. Pulmonary function is monitored including exhaled nitric oxide studies as well as conventional pulmonary studies such as airway responsiveness to inhaled methacholine as markers of non-specific inflammation induced by EGS.

Those skilled in the art will recognize, or be able to ascertain using no more than routine experimentation, many equivalents to the specific embodiments of the invention described herein. Such equivalents are intended to be encompassed by the following claims.

I claim:

1. A composition comprising a nuclease resistant external guide sequence comprising the nucleotide sequence of SEQ ID NO: 6 and a pharmaceutically acceptable carrier, wherein the external guide sequence binds to a cleavage site on a target RNA wherein the target RNA comprises a sequence that encodes an IL-4/IL-13 signaling pathway molecule and wherein the external guide sequence guides RNase P to cleave the target RNA, thereby degrading the target RNA.

2. The external guide sequence composition of claim 1 wherein the external guide sequence is formulated for administration via inhalation.

3. A composition comprising the external guide sequence of claim 1 in a dosage form for pulmonary administration.

4. The composition of claim 1 wherein the external guide sequence binds to an mRNA encoding a cytokine receptor, wherein the cytokine receptor is IL-4 receptor α chain.

5. The external guide sequence composition of claim 1, wherein the external guide sequence has a chemical modification added to the 3' end of the nucleotide sequence, wherein the chemical modification decreases susceptibility of the nucleotide sequence from exonuclease degradation.

* * * * *

SEQUENCE LISTING

<160> NUMBER OF SEQ ID NOS: 105

<210> SEQ ID NO 1
<211> LENGTH: 19
<212> TYPE: RNA
<213> ORGANISM: artificial sequence
<220> FEATURE:
<223> OTHER INFORMATION: murine targeting sequence of
      IL-4-receptor-alpha mRNA

<400> SEQUENCE: 1
auggggcggc uuugcacca                                                     19

<210> SEQ ID NO 2
<211> LENGTH: 19
<212> TYPE: RNA
<213> ORGANISM: Artificial sequence
<220> FEATURE:
<223> OTHER INFORMATION: human targeting sequence of IL-4-receptor-alpha
      mRNA

<400> SEQUENCE: 2 auggggugge uuugcucug                                                     19

<210> SEQ ID NO 3
<211> LENGTH: 35
<212> TYPE: RNA
<213> ORGANISM: Artificial sequence
<220> FEATURE:
<223> OTHER INFORMATION: murine IL-4 receptor-alpha EGS
<220> FEATURE:
<221> NAME/KEY: misc_feature
<222> LOCATION: (1)..(12)
<223> OTHER INFORMATION: 2'-O-methyl modification
<220> FEATURE:
<221> NAME/KEY: misc_feature
<222> LOCATION: (13)..(13)
<223> OTHER INFORMATION: deoxy modification
<220> FEATURE:
<221> NAME/KEY: misc_feature
<222> LOCATION: (14)..(14)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
<221> NAME/KEY: misc_feature
<222> LOCATION: (19)..(35)
<223> OTHER INFORMATION: 2'-O-methyl modification

<400> SEQUENCE: 3
uggugcagaa gguuagaauc cuucgccgcc cacca                                   35

<210> SEQ ID NO 4
<211> LENGTH: 35
<212> TYPE: RNA
<213> ORGANISM: Artificial Sequence
<220> FEATURE:
<223> OTHER INFORMATION: murine IL-4 receptor-alpha reversed T loop
      control EGS
<220> FEATURE:
<221> NAME/KEY: misc_feature
<222> LOCATION: (1)..(13)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
<221> NAME/KEY: misc_feature

```
<222> LOCATION: (18)..(18)
<223> OTHER INFORMATION: 2'-O-methyl modification
<220> FEATURE:
<221> NAME/KEY: misc_feature
<222> LOCATION: (19)..(19)
<223> OTHER INFORMATION: deoxy modification
<220> FEATURE:
<221> NAME/KEY: misc_feature
<222> LOCATION: (20)..(35)
<223> OTHER INFORMATION: 2'-O-methyl modification

<400> SEQUENCE: 4
uggugcagaa gguaagauuc cuucgccgcc cacca                         35

<210> SEQ ID NO 5
<211> LENGTH: 35
<212> TYPE: RNA
<213> ORGANISM: Artificial sequence
<220> FEATURE:
<223> OTHER INFORMATION: murine IL-4 receptor-alpha active EGS
<220> FEATURE:
<221> NAME/KEY: misc_feature
<222> LOCATION: (1)..(12)
<223> OTHER INFORMATION: 2'-O-methyl modification
<220> FEATURE:
<221> NAME/KEY: misc_feature
<222> LOCATION: (13)..(13)
<223> OTHER INFORMATION: deoxy modification
<220> FEATURE:
<221> NAME/KEY: misc_feature
<222> LOCATION: (14)..(14)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
<221> NAME/KEY: misc_feature
<222> LOCATION: (19)..(35)
<223> OTHER INFORMATION: 2'-O-methyl modification

<400> SEQUENCE: 5
uggugcagaa gguuagaauc cuucgccgcc cacca                         35

<210> SEQ ID NO 6
<211> LENGTH: 35
<212> TYPE: RNA
<213> ORGANISM: Artificial sequence
<220> FEATURE:
<223> OTHER INFORMATION: human IL-4-receptor-alpha active EGS
<220> FEATURE:
<221> NAME/KEY: misc_feature
<222> LOCATION: (1)..(12)
<223> OTHER INFORMATION: 2'-O-methyl modification
<220> FEATURE:
<221> NAME/KEY: misc_feature
<222> LOCATION: (13)..(13)
<223> OTHER INFORMATION: deoxy modification
<220> FEATURE:
<221> NAME/KEY: misc_feature
<222> LOCATION: (14)..(14)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
<221> NAME/KEY: misc_feature
<222> LOCATION: (19)..(35)
<223> OTHER INFORMATION: 2'-O-methyl modification

<400> SEQUENCE: 6
cagagcagaa gguuagaauc cuucgccacc cacca                         35
```

```
<210> SEQ ID NO 7
<211> LENGTH: 35
<212> TYPE: RNA
<213> ORGANISM: Artificial sequence
<220> FEATURE:
<223> OTHER INFORMATION: human IL-4 receptor-alpha reversed T loop
      control EGS
<220> FEATURE:
<221> NAME/KEY: misc_feature
<222> LOCATION: (1)..(13)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
<221> NAME/KEY: misc_feature
<222> LOCATION: (18)..(18)
<223> OTHER INFORMATION: 2'-O-methyl modification
<220> FEATURE:
<221> NAME/KEY: misc_feature
<222> LOCATION: (19)..(19)
<223> OTHER INFORMATION: deoxy modification
<220> FEATURE:
<221> NAME/KEY: misc_feature
<222> LOCATION: (20)..(35)
<223> OTHER INFORMATION: 2'-O-methyl modification

<400> SEQUENCE: 7
cagagcagaa gguaagauuc cuucgccacc cacca                       35

<210> SEQ ID NO 8
<211> LENGTH: 35
<212> TYPE: RNA
<213> ORGANISM: Artificial sequence
<220> FEATURE:
<223> OTHER INFORMATION: human IL-4-receptor-alpha active EGS
<220> FEATURE:
<221> NAME/KEY: misc_feature
<222> LOCATION: (1)..(12)
<223> OTHER INFORMATION: 2'-O-methyl modification
<220> FEATURE:
<221> NAME/KEY: misc_feature
<222> LOCATION: (13)..(13)
<223> OTHER INFORMATION: deoxy modification
<220> FEATURE:
<221> NAME/KEY: misc_feature
<222> LOCATION: (14)..(14)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
<221> NAME/KEY: misc_feature
<222> LOCATION: (19)..(35)
<223> OTHER INFORMATION: 2'-O-methyl modification

<400> SEQUENCE: 8
cagagcagaa gguuagaauc cuucgccacc cacca                       35

<210> SEQ ID NO 9
<211> LENGTH: 18
<212> TYPE: RNA
<213> ORGANISM: Artificial sequence
<220> FEATURE:
<223> OTHER INFORMATION: murine targeting sequence of STAT6 mRNA

<400> SEQUENCE: 9
augucucugu ggggccua                                          18

<210> SEQ ID NO 10
<211> LENGTH: 18
<212> TYPE: RNA
```

```
<213> ORGANISM: Artificial sequence
<220> FEATURE:
<223> OTHER INFORMATION: human targeting sequence of STAT6 mRNA

<400> SEQUENCE: 10
augucucugu ggggucug                                                 18

<210> SEQ ID NO 11
<211> LENGTH: 35
<212> TYPE: RNA
<213> ORGANISM: Artificial sequence
<220> FEATURE:
<223> OTHER INFORMATION: murine STAT6 active EGS
<220> FEATURE:
<221> NAME/KEY: misc_feature
<222> LOCATION: (1)..(12)
<223> OTHER INFORMATION: 2'-O-methyl modification
<220> FEATURE:
<221> NAME/KEY: misc_feature
<222> LOCATION: (13)..(13)
<223> OTHER INFORMATION: deoxy modification
<220> FEATURE:
<221> NAME/KEY: misc_feature
<222> LOCATION: (14)..(14)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
<221> NAME/KEY: misc_feature
<222> LOCATION: (19)..(35)
<223> OTHER INFORMATION: 2'-O-methyl modification

<400> SEQUENCE: 11
uaggcccgaa gguuagaauc cuuccagaga cacca                              35

<210> SEQ ID NO 12
<211> LENGTH: 35
<212> TYPE: RNA
<213> ORGANISM: Artificial sequence
<220> FEATURE:
<223> OTHER INFORMATION: murine STAT6 reversed T loop control EGS
<220> FEATURE:
<221> NAME/KEY: misc_feature
<222> LOCATION: (1)..(13)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
<221> NAME/KEY: misc_feature
<222> LOCATION: (18)..(18)
<223> OTHER INFORMATION: 2'-O-methyl modification
<220> FEATURE:
<221> NAME/KEY: misc_feature
<222> LOCATION: (19)..(19)
<223> OTHER INFORMATION: deoxy modification
<220> FEATURE:
<221> NAME/KEY: misc_feature
<222> LOCATION: (20)..(35)
<223> OTHER INFORMATION: 2'-O-methyl modification

<400> SEQUENCE: 12
uaggcccgaa gguaagauuc cuuccagaga cacca                              35

<210> SEQ ID NO 13
<211> LENGTH: 35
<212> TYPE: RNA
<213> ORGANISM: Artificial sequence
<220> FEATURE:
<223> OTHER INFORMATION: murine STAT6 active EGS
<220> FEATURE:
```

```
<221> NAME/KEY: misc_feature
<222> LOCATION: (1)..(12)
<223> OTHER INFORMATION: 2'-O-methyl modification
<220> FEATURE:
<221> NAME/KEY: misc_feature
<222> LOCATION: (13)..(13)
<223> OTHER INFORMATION: deoxy modification
<220> FEATURE:
<221> NAME/KEY: misc_feature
<222> LOCATION: (14)..(14)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
<221> NAME/KEY: misc_feature
<222> LOCATION: (19)..(35)
<223> OTHER INFORMATION: 2'-O-methyl modification

<400> SEQUENCE: 13
uaggcccgaa gguuagaauc cuuccagaga cacca                              35

<210> SEQ ID NO 14
<211> LENGTH: 35
<212> TYPE: RNA
<213> ORGANISM: artificial sequence
<220> FEATURE:
<223> OTHER INFORMATION: human STAT6 active EGS
<220> FEATURE:
<221> NAME/KEY: misc_feature
<222> LOCATION: (1)..(12)
<223> OTHER INFORMATION: 2'-O-methyl modification
<220> FEATURE:
<221> NAME/KEY: misc_feature
<222> LOCATION: (13)..(13)
<223> OTHER INFORMATION: deoxy modification
<220> FEATURE:
<221> NAME/KEY: misc_feature
<222> LOCATION: (14)..(14)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
<221> NAME/KEY: misc_feature
<222> LOCATION: (19)..(35)
<223> OTHER INFORMATION: 2'-O-methyl modification

<400> SEQUENCE: 14
cagacccgaa gguuagaauc cuuccagaga cacca                              35

<210> SEQ ID NO 15
<211> LENGTH: 35
<212> TYPE: RNA
<213> ORGANISM: artificial sequence
<220> FEATURE:
<223> OTHER INFORMATION: human STAT6 reversed T loop control EGS
<220> FEATURE:
<221> NAME/KEY: misc_feature
<222> LOCATION: (1)..(13)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
<221> NAME/KEY: misc_feature
<222> LOCATION: (18)..(18)
<223> OTHER INFORMATION: 2'-O-methyl modification
<220> FEATURE:
<221> NAME/KEY: misc_feature
<222> LOCATION: (19)..(19)
<223> OTHER INFORMATION: deoxy modification
<220> FEATURE:
```

```
<221> NAME/KEY: misc_feature
<222> LOCATION: (20)..(35)
<223> OTHER INFORMATION: 2'-O-methyl modification

<400> SEQUENCE: 15
cagacccgaa gguaagauuc cuuccagaga cacca                                    35

<210> SEQ ID NO 16
<211> LENGTH: 35
<212> TYPE: RNA
<213> ORGANISM: artificial sequence
<220> FEATURE:
<223> OTHER INFORMATION: human STAT6 active EGS
<220> FEATURE:
<221> NAME/KEY: misc_feature
<222> LOCATION: (1)..(12)
<223> OTHER INFORMATION: 2'-O-methyl modification
<220> FEATURE:
<221> NAME/KEY: misc_feature
<222> LOCATION: (13)..(13)
<223> OTHER INFORMATION: deoxy modification
<220> FEATURE:
<221> NAME/KEY: misc_feature
<222> LOCATION: (14)..(14)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
<221> NAME/KEY: misc_feature
<222> LOCATION: (19)..(35)
<223> OTHER INFORMATION: 2'-O-methyl modification

<400> SEQUENCE: 16
cagacccgaa gguuagaauc cuuccagaga cacca                                    35

<210> SEQ ID NO 17
<211> LENGTH: 13
<212> TYPE: DNA
<213> ORGANISM: artificial sequence
<220> FEATURE:
<223> OTHER INFORMATION: human targeting sequence IL-4-receptor alpha

<400> SEQUENCE: 17
gggtggcttt gct                                                            13

<210> SEQ ID NO 18
<211> LENGTH: 54
<212> TYPE: DNA
<213> ORGANISM: artificial sequence
<220> FEATURE:
<223> OTHER INFORMATION: sense strand IL-4-receptor alpha synthetic
      oligonucleotide

<400> SEQUENCE: 18
gagcaacgtc atcgacttcg aaggttcgaa tccttcgcca cccaccattt ttaa               54

<210> SEQ ID NO 19
<211> LENGTH: 62
<212> TYPE: DNA
<213> ORGANISM: artificial sequence
<220> FEATURE:
<223> OTHER INFORMATION: antisense strand IL-4-receptor alpha synthetic
      oligonucleotide

<400> SEQUENCE: 19
agctttaaaa atggtgggtg gcgaaggatt cgaaccttcg aagtcgatga cgttgctctg         60
ca                                                                        62
```

<210> SEQ ID NO 20
<211> LENGTH: 53
<212> TYPE: DNA
<213> ORGANISM: artificial sequence
<220> FEATURE:
<223> OTHER INFORMATION: sense strand IL-4-receptor alpha mutant
      synthetic oligonucleotide

<400> SEQUENCE: 20
gagcaacgtc atcgacttcg aagggatccg ccttcgccac ccaccatttt taa     53

<210> SEQ ID NO 21
<211> LENGTH: 62
<212> TYPE: DNA
<213> ORGANISM: artificial sequence
<220> FEATURE:
<223> OTHER INFORMATION: antisense strand of IL-4-receptor alpha mutant
      synthetic oligonucleotide

<400> SEQUENCE: 21
agctttaaaa atggtgggtg gcgaaggcgg atcccttcg aagtcgatga cgttgctctg     60
ca                                                                   62

<210> SEQ ID NO 22
<211> LENGTH: 13
<212> TYPE: DNA
<213> ORGANISM: artificial sequence
<220> FEATURE:
<223> OTHER INFORMATION: murine target sequence for IL-4-receptor-alpha

<400> SEQUENCE: 22
gggtggcttt gct                                                       13

<210> SEQ ID NO 23
<211> LENGTH: 54
<212> TYPE: DNA
<213> ORGANISM: artificial sequence
<220> FEATURE:
<223> OTHER INFORMATION: sense strand murine IL-4-receptor-alpha
      synthetic oligonucleotide

<400> SEQUENCE: 23
gtgcaacgtc atcgacttcg aaggttcgaa tccttcgccg cccaccattt ttaa           54

<210> SEQ ID NO 24
<211> LENGTH: 62
<212> TYPE: DNA
<213> ORGANISM: artificial sequence
<220> FEATURE:
<223> OTHER INFORMATION: antisense strand muring IL-4-receptor alpha
      synthetic oligonucleotide

<400> SEQUENCE: 24
agctttaaaa atggtgggcg gcgaaggatt cgaaccttcg aagtcgatga cgttgcactg     60
ca                                                                   62

<210> SEQ ID NO 25
<211> LENGTH: 54
<212> TYPE: DNA
<213> ORGANISM: artificial sequence
<220> FEATURE:
<223> OTHER INFORMATION: sense strand muring IL-4-receptor-alpha mutant
      synthetic oligonucleotide

<400> SEQUENCE: 25
gtgcaacgtc atcgacttcg aaggggatcc gccttcgccg cccaccattt ttaa           54

```
<210> SEQ ID NO 26
<211> LENGTH: 62
<212> TYPE: DNA
<213> ORGANISM: artificial sequence
<220> FEATURE:
<223> OTHER INFORMATION: antisense strand murine IL-4-receptor-alpha
      mutant synthetic oligonucleotide

<400> SEQUENCE: 26
agctttaaaa atggtgggcg gcgaaggcgg atcccctcg aagtcgatga cgttgcactg       60
ca                                                                     62

<210> SEQ ID NO 27
<211> LENGTH: 18
<212> TYPE: DNA
<213> ORGANISM: artificial sequence
<220> FEATURE:
<223> OTHER INFORMATION: murine targeting sequence for AR1

<400> SEQUENCE: 27
atgccgccgt acatctcg                                                    18

<210> SEQ ID NO 28
<211> LENGTH: 18
<212> TYPE: DNA
<213> ORGANISM: artificial sequence
<220> FEATURE:
<223> OTHER INFORMATION: human targeting sequence for AR1

<400> SEQUENCE: 28
atgccgccct ccatctca                                                    18

<210> SEQ ID NO 29
<211> LENGTH: 35
<212> TYPE: RNA
<213> ORGANISM: artificial sequence
<220> FEATURE:
<223> OTHER INFORMATION: murine AR1 active EGS
<220> FEATURE:
<221> NAME/KEY: misc_feature
<222> LOCATION: (1)..(12)
<223> OTHER INFORMATION: 2'-O-methyl modification
<220> FEATURE:
<221> NAME/KEY: misc_feature
<222> LOCATION: (13)..(13)
<223> OTHER INFORMATION: deoxy modification
<220> FEATURE:
<221> NAME/KEY: misc_feature
<222> LOCATION: (14)..(14)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
<221> NAME/KEY: misc_feature
<222> LOCATION: (19)..(35)
<223> OTHER INFORMATION: 2'-O-methyl modification

<400> SEQUENCE: 29
cgagauggaa gguuagaauc cuuccggcgg cacca                                 35

<210> SEQ ID NO 30
<211> LENGTH: 35
<212> TYPE: RNA
<213> ORGANISM: artificial sequence
<220> FEATURE:
<223> OTHER INFORMATION: murine AR1 reversed T loop control EGS
<220> FEATURE:
```

```
<221> NAME/KEY: misc_feature
<222> LOCATION: (1)..(13)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
<221> NAME/KEY: misc_feature
<222> LOCATION: (18)..(18)
<223> OTHER INFORMATION: 2'-O-methyl modification
<220> FEATURE:
<221> NAME/KEY: misc_feature
<222> LOCATION: (19)..(19)
<223> OTHER INFORMATION: deoxy modification
<220> FEATURE:
<221> NAME/KEY: misc_feature
<222> LOCATION: (20)..(35)
<223> OTHER INFORMATION: 2'-O-methyl modification

<400> SEQUENCE: 30
cgagauggaa gguaagauuc cuuccggcgg cacca                                35

<210> SEQ ID NO 31
<211> LENGTH: 35
<212> TYPE: RNA
<213> ORGANISM: artificial sequence
<220> FEATURE:
<223> OTHER INFORMATION: murine AR1 active EGS
<220> FEATURE:
<221> NAME/KEY: misc_feature
<222> LOCATION: (1)..(12)
<223> OTHER INFORMATION: 2'-O-methyl modification
<220> FEATURE:
<221> NAME/KEY: misc_feature
<222> LOCATION: (13)..(13)
<223> OTHER INFORMATION: deoxy modification
<220> FEATURE:
<221> NAME/KEY: misc_feature
<222> LOCATION: (14)..(14)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
<221> NAME/KEY: misc_feature
<222> LOCATION: (19)..(35)
<223> OTHER INFORMATION: 2'-O-methyl modification

<400> SEQUENCE: 31
cgagauggaa gguuagaauc cuuccggcgg cacca                                35

<210> SEQ ID NO 32
<211> LENGTH: 35
<212> TYPE: RNA
<213> ORGANISM: artificial sequence
<220> FEATURE:
<223> OTHER INFORMATION: human AR1 active EGS
<220> FEATURE:
<221> NAME/KEY: misc_feature
<222> LOCATION: (1)..(12)
<223> OTHER INFORMATION: 2'-O-methyl modification
<220> FEATURE:
<221> NAME/KEY: misc_feature
<222> LOCATION: (13)..(13)
<223> OTHER INFORMATION: deoxy modification
<220> FEATURE:
<221> NAME/KEY: misc_feature
<222> LOCATION: (14)..(14)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
```

```
<221> NAME/KEY: misc_feature
<222> LOCATION: (19)..(35)
<223> OTHER INFORMATION: 2'-O-methyl modification

<400> SEQUENCE: 32
ugagauggaa gguuagaauc cuucgggcgg cacca                         35

<210> SEQ ID NO 33
<211> LENGTH: 21
<212> TYPE: DNA
<213> ORGANISM: artificial sequence
<220> FEATURE:
<223> OTHER INFORMATION: murine targeting sequence of RAG1

<400> SEQUENCE: 33
atggctgcct ccttgccgtc t                                        21

<210> SEQ ID NO 34
<211> LENGTH: 21
<212> TYPE: DNA
<213> ORGANISM: artificial sequence
<220> FEATURE:
<223> OTHER INFORMATION: human targeting sequence for RAG 1

<400> SEQUENCE: 34
atggcagcct ctttcccacc c                                        21

<210> SEQ ID NO 35
<211> LENGTH: 35
<212> TYPE: RNA
<213> ORGANISM: artificial sequence
<220> FEATURE:
<223> OTHER INFORMATION: murine RAG1 active EGS
<220> FEATURE:
<221> NAME/KEY: misc_feature
<222> LOCATION: (1)..(12)
<223> OTHER INFORMATION: 2'-O-methyl modification
<220> FEATURE:
<221> NAME/KEY: misc_feature
<222> LOCATION: (13)..(13)
<223> OTHER INFORMATION: deoxy modification
<220> FEATURE:
<221> NAME/KEY: misc_feature
<222> LOCATION: (14)..(14)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
<221> NAME/KEY: misc_feature
<222> LOCATION: (19)..(35)
<223> OTHER INFORMATION: 2'-O-methyl modification

<400> SEQUENCE: 35
cggcaaggaa gguuagaauc cuucggcagc cacca                         35

<210> SEQ ID NO 36
<211> LENGTH: 35
<212> TYPE: RNA
<213> ORGANISM: artificial sequence
<220> FEATURE:
<223> OTHER INFORMATION: murine RAG1 reversed T loop control EGS
<220> FEATURE:
<221> NAME/KEY: misc_feature
<222> LOCATION: (1)..(12)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
```

```
<221> NAME/KEY: misc_feature
<222> LOCATION: (18)..(18)
<223> OTHER INFORMATION: 2'-O-methyl modification
<220> FEATURE:
<221> NAME/KEY: misc_feature
<222> LOCATION: (19)..(19)
<223> OTHER INFORMATION: deoxy modification
<220> FEATURE:
<221> NAME/KEY: misc_feature
<222> LOCATION: (20)..(35)
<223> OTHER INFORMATION: 2'-O-methyl modification

<400> SEQUENCE: 36
cggcaaggaa gguaagauuc cuucggcagc cacca                                35

<210> SEQ ID NO 37
<211> LENGTH: 35
<212> TYPE: RNA
<213> ORGANISM: artificial sequence
<220> FEATURE:
<223> OTHER INFORMATION: murine RAG1 active EGS
<220> FEATURE:
<221> NAME/KEY: misc_feature
<222> LOCATION: (1)..(12)
<223> OTHER INFORMATION: 2'-O-methyl modification
<220> FEATURE:
<221> NAME/KEY: misc_feature
<222> LOCATION: (13)..(13)
<223> OTHER INFORMATION: deoxy modification
<220> FEATURE:
<221> NAME/KEY: misc_feature
<222> LOCATION: (14)..(14)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
<221> NAME/KEY: misc_feature
<222> LOCATION: (19)..(35)
<223> OTHER INFORMATION: 2'-O-methyl modification

<400> SEQUENCE: 37
cggcaaggaa gguuagaauc cuucggcagc cacca                                35

<210> SEQ ID NO 38
<211> LENGTH: 35
<212> TYPE: RNA
<213> ORGANISM: artificial sequence
<220> FEATURE:
<223> OTHER INFORMATION: human RAG1 active EGS
<220> FEATURE:
<221> NAME/KEY: misc_feature
<222> LOCATION: (1)..(12)
<223> OTHER INFORMATION: 2'-O-methyl modification
<220> FEATURE:
<221> NAME/KEY: misc_feature
<222> LOCATION: (13)..(13)
<223> OTHER INFORMATION: deoxy modification
<220> FEATURE:
<221> NAME/KEY: misc_feature
<222> LOCATION: (14)..(14)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification
<220> FEATURE:
<221> NAME/KEY: misc_feature
<222> LOCATION: (19)..(35)
<223> OTHER INFORMATION: 2'-O-methyl modification

<400> SEQUENCE: 38
ugggaaagaa gguuagaauc cuucggcugc cacca                                35
```

-continued

```
<210> SEQ ID NO 39
<211> LENGTH: 17
<212> TYPE: RNA
<213> ORGANISM: artificial sequence
<220> FEATURE:
<223> OTHER INFORMATION: human IL-4-receptor alpha targeting sequence

<400> SEQUENCE: 39
gaaggucuug caggagc                                                    17

<210> SEQ ID NO 40
<211> LENGTH: 25
<212> TYPE: RNA
<213> ORGANISM: artificial sequence
<220> FEATURE:
<223> OTHER INFORMATION: human STAT6 targeting sequence

<400> SEQUENCE: 40
augucucugu ggggcucugg ucucc                                            25

<210> SEQ ID NO 41
<211> LENGTH: 23
<212> TYPE: RNA
<213> ORGANISM: artificial sequence
<220> FEATURE:
<223> OTHER INFORMATION: human IL13 targeting sequence

<400> SEQUENCE: 41
auggcgcuuu uguugaccac ggu                                              23

<210> SEQ ID NO 42
<211> LENGTH: 23
<212> TYPE: RNA
<213> ORGANISM: artificial sequence
<220> FEATURE:
<223> OTHER INFORMATION: human IL13 targeting sequence

<400> SEQUENCE: 42
auggcgcuuu uguugaccac ggu                                              23

<210> SEQ ID NO 43
<211> LENGTH: 15
<212> TYPE: RNA
<213> ORGANISM: artificial sequence
<220> FEATURE:
<223> OTHER INFORMATION: human CD40 targeting sequence

<400> SEQUENCE: 43
guuuuucuua ucacc                                                       15

<210> SEQ ID NO 44
<211> LENGTH: 13
<212> TYPE: RNA
<213> ORGANISM: artificial sequence
<220> FEATURE:
<223> OTHER INFORMATION: human CD40 targeting sequence

<400> SEQUENCE: 44
gaaggcuuug uga                                                         13

<210> SEQ ID NO 45
<211> LENGTH: 17
<212> TYPE: DNA
<213> ORGANISM: artificial sequence
<220> FEATURE:
<223> OTHER INFORMATION: human CD40 targeting sequence
```

<400> SEQUENCE: 45
gataccauuu caacuuu                                                      17

<210> SEQ ID NO 46
<211> LENGTH: 20
<212> TYPE: RNA
<213> ORGANISM: artificial sequence
<220> FEATURE:
<223> OTHER INFORMATION: human CD40 receptor targeting sequence

<400> SEQUENCE: 46
augguucguc ugccucugca                                                   20

<210> SEQ ID NO 47
<211> LENGTH: 17
<212> TYPE: RNA
<213> ORGANISM: artificial sequence
<220> FEATURE:
<223> OTHER INFORMATION: human CD40 receptor targeting sequence

<400> SEQUENCE: 47
gucugccucu gcagugc                                                      17

<210> SEQ ID NO 48
<211> LENGTH: 18
<212> TYPE: RNA
<213> ORGANISM: artificial sequence
<220> FEATURE:
<223> OTHER INFORMATION: human CD40 receptor targeting sequence

<400> SEQUENCE: 48
gccaugguuc gucugccu                                                     18

<210> SEQ ID NO 49
<211> LENGTH: 21
<212> TYPE: RNA
<213> ORGANISM: artificial sequence
<220> FEATURE:
<223> OTHER INFORMATION: human C3d receptor targeting sequence

<400> SEQUENCE: 49
gcgggccugc ucgggguuuu c                                                 21

<210> SEQ ID NO 50
<211> LENGTH: 21
<212> TYPE: RNA
<213> ORGANISM: artificial sequence
<220> FEATURE:
<223> OTHER INFORMATION: human C3d receptor targeting sequence

<400> SEQUENCE: 50
ggggsuuucu uggcucucgu c                                                 21

<210> SEQ ID NO 51
<211> LENGTH: 18
<212> TYPE: RNA
<213> ORGANISM: artificial sequence
<220> FEATURE:
<223> OTHER INFORMATION: human A-1 receptor targeting sequence

<400> SEQUENCE: 51
augccgcccu ccaucuca                                                     18

<210> SEQ ID NO 52
<211> LENGTH: 18
<212> TYPE: RNA

<213> ORGANISM: artificial sequence
<220> FEATURE:
<223> OTHER INFORMATION: murine A-1 receptor targeting sequence

<400> SEQUENCE: 52
augccgccgu acaucucg                                                        18

<210> SEQ ID NO 53
<211> LENGTH: 21
<212> TYPE: RNA
<213> ORGANISM: artificial sequence
<220> FEATURE:
<223> OTHER INFORMATION: human TGF beta receptor 1 targeting sequence

<400> SEQUENCE: 53
gggaccaugg aggcggcggu c                                                    21

<210> SEQ ID NO 54
<211> LENGTH: 25
<212> TYPE: RNA
<213> ORGANISM: artificial sequence
<220> FEATURE:
<223> OTHER INFORMATION: human TGF beta receptor 1 targeting sequence

<400> SEQUENCE: 54
auggaggcgg cggucgcugc uccgc                                                25

<210> SEQ ID NO 55
<211> LENGTH: 27
<212> TYPE: RNA
<213> ORGANISM: artificial sequence
<220> FEATURE:
<223> OTHER INFORMATION: human TGF beta receptor 2 targeting sequence

<400> SEQUENCE: 55
augggucggg ggcugcucag gggccug                                              27

<210> SEQ ID NO 56
<211> LENGTH: 21
<212> TYPE: RNA
<213> ORGANISM: artificial sequence
<220> FEATURE:
<223> OTHER INFORMATION: human TGF beta cytokine targeting sequence

<400> SEQUENCE: 56
augccgcccu ccgggcugcg g                                                    21

<210> SEQ ID NO 57
<211> LENGTH: 20
<212> TYPE: RNA
<213> ORGANISM: artificial sequence
<220> FEATURE:
<223> OTHER INFORMATION: human TGF beta transcription factor targeting
      sequence

<400> SEQUENCE: 57
auggacaaua ugucuauuac                                                      20

<210> SEQ ID NO 58
<211> LENGTH: 21
<212> TYPE: RNA
<213> ORGANISM: artificial sequence
<220> FEATURE:
<223> OTHER INFORMATION: human TGF beta transcription factor targeting
      sequence

<400> SEQUENCE: 58

-continued gaacaaaugg acaauauguc u                                          21

<210> SEQ ID NO 59
<211> LENGTH: 25
<212> TYPE: RNA
<213> ORGANISM: artificial sequence
<220> FEATURE:
<223> OTHER INFORMATION: human EGF receptor targeting sequence

<400> SEQUENCE: 59
augcgacccu ccgggacggc cgggg                                      25

<210> SEQ ID NO 60
<211> LENGTH: 23
<212> TYPE: RNA
<213> ORGANISM: artificial sequence
<220> FEATURE:
<223> OTHER INFORMATION: human EGF receptor targeting sequence

<400> SEQUENCE: 60
gcagcgaugc gacccuccgg gac                                        23

<210> SEQ ID NO 61
<211> LENGTH: 20
<212> TYPE: RNA
<213> ORGANISM: artificial sequence
<220> FEATURE:
<223> OTHER INFORMATION: human IL-10 receptor targeting sequence

<400> SEQUENCE: 61
augcugccgu gccucguagu                                            20

<210> SEQ ID NO 62
<211> LENGTH: 20
<212> TYPE: RNA
<213> ORGANISM: artificial sequence
<220> FEATURE:
<223> OTHER INFORMATION: human IL-10 receptor targeting sequence

<400> SEQUENCE: 62
guagugcugc uggcggcgcu 20

<210> SEQ ID NO 63
<211> LENGTH: 18
<212> TYPE: RNA
<213> ORGANISM: artificial sequence
<220> FEATURE:
<223> OTHER INFORMATION: human IL-10 cytokine targeting sequence

<400> SEQUENCE: 63
augcacagcu cagcacug 18

<210> SEQ ID NO 64
<211> LENGTH: 20
<212> TYPE: RNA
<213> ORGANISM: artificial sequence
<220> FEATURE:
<223> OTHER INFORMATION: human RAG1 targeting sequence

<400> SEQUENCE: 64
auggcagccu cuuucccacc 20

<210> SEQ ID NO 65
<211> LENGTH: 20
<212> TYPE: RNA
<213> ORGANISM: artificial sequence
<220> FEATURE:

-continued

```
<223> OTHER INFORMATION: murine RAG1 targeting sequence

<400> SEQUENCE: 65
auggcugccu ccauugccgu                                              20

<210> SEQ ID NO 66
<211> LENGTH: 22
<212> TYPE: RNA
<213> ORGANISM: artificial sequence
<220> FEATURE:
<223> OTHER INFORMATION: human NFkB p65 targeting sequence

<400> SEQUENCE: 66
auggacgaac uguuccccu ca                                            22

<210> SEQ ID NO 67
<211> LENGTH: 22
<212> TYPE: RNA
<213> ORGANISM: artificial sequence
<220> FEATURE:
<223> OTHER INFORMATION: murine NFkB p65 targeting sequence

<400> SEQUENCE: 67
auggacgauc uguuucccu ca                                            22

<210> SEQ ID NO 68
<211> LENGTH: 27
<212> TYPE: RNA
<213> ORGANISM: artificial sequence
<220> FEATURE:
<223> OTHER INFORMATION: human NFkB p65 targeting sequence

<400> SEQUENCE: 68
auggacgaac uguccccu caucuuc                                        27

<210> SEQ ID NO 69
<211> LENGTH: 27
<212> TYPE: RNA
<213> ORGANISM: artificial sequence
<220> FEATURE:
<223> OTHER INFORMATION: murine NFkB p65 targeting sequence

<400> SEQUENCE: 69
auggacgauc uguuucccu caucuuu                                       27

<210> SEQ ID NO 70
<211> LENGTH: 28
<212> TYPE: RNA
<213> ORGANISM: artificial sequence
<220> FEATURE:
<223> OTHER INFORMATION: human NFkB p50 targeting sequence

<400> SEQUENCE: 70
auggagaguu gcuacaaccc aggucugg                                     28

<210> SEQ ID NO 71
<211> LENGTH: 28
<212> TYPE: RNA
<213> ORGANISM: artificial sequence
<220> FEATURE:
<223> OTHER INFORMATION: human NFkB p50 targeting sequence

<400> SEQUENCE: 71
auggagaguu gcuacaaccc aggucugg                                     28

<210> SEQ ID NO 72
```

```
<211> LENGTH: 20
<212> TYPE: RNA
<213> ORGANISM: artificial sequence
<220> FEATURE:
<223> OTHER INFORMATION: H1N1 elongation factor targeting sequence

<400> SEQUENCE: 72
auggaaagaa uaaaagaacu                                                      20

<210> SEQ ID NO 73
<211> LENGTH: 20
<212> TYPE: RNA
<213> ORGANISM: artificial sequence
<220> FEATURE:
<223> OTHER INFORMATION: H5N1 elongation factor targeting sequence

<400> SEQUENCE: 73
auggagagaa uaaaagaauu                                                      20

<210> SEQ ID NO 74
<211> LENGTH: 20
<212> TYPE: RNA
<213> ORGANISM: artificial sequence
<220> FEATURE:
<223> OTHER INFORMATION: H1N1 elongation factor targeting sequence

<400> SEQUENCE: 74
gucgcagucu cgcacccgcg                                                      20

<210> SEQ ID NO 75
<211> LENGTH: 20
<212> TYPE: RNA
<213> ORGANISM: artificial sequence
<220> FEATURE:
<223> OTHER INFORMATION: H5N1 elongation factor targeting sequence

<400> SEQUENCE: 75
gucacagucc cgcacucgcg                                                      20

<210> SEQ ID NO 76
<211> LENGTH: 20
<212> TYPE: RNA
<213> ORGANISM: artificial sequence
<220> FEATURE:
<223> OTHER INFORMATION: H1N1 elongation factor targeting sequence

<400> SEQUENCE: 76
guacacauca ggaagacagg                                                      20

<210> SEQ ID NO 77
<211> LENGTH: 20
<212> TYPE: RNA
<213> ORGANISM: artificial sequence
<220> FEATURE:
<223> OTHER INFORMATION: H1N1 nucleocapsid targeting sequnce

<400> SEQUENCE: 77
gaacagaugg agacugaugg                                                      20

<210> SEQ ID NO 78
<211> LENGTH: 20
<212> TYPE: RNA
<213> ORGANISM: artificial sequence
<220> FEATURE:
<223> OTHER INFORMATION: H5N1 nucleocapsid targeting sequence

<400> SEQUENCE: 78
```

-continued

```
gaacagaugg aaacugaugg                                              20

<210> SEQ ID NO 79
<211> LENGTH: 21
<212> TYPE: RNA
<213> ORGANISM: artificial sequence
<220> FEATURE:
<223> OTHER INFORMATION: H1N1 nucleocapsid targeting sequence

<400> SEQUENCE: 79
gccagaaugc cacugaaauc a                                            21

<210> SEQ ID NO 80
<211> LENGTH: 21
<212> TYPE: RNA
<213> ORGANISM: artificial sequence
<220> FEATURE:
<223> OTHER INFORMATION: H5N1 nucleocapsid targeting sequence

<400> SEQUENCE: 80
gccagaaugc uacugagauc a                                            21

<210> SEQ ID NO 81
<211> LENGTH: 21
<212> TYPE: RNA
<213> ORGANISM: artificial sequence
<220> FEATURE:
<223> OTHER INFORMATION: H1N1 acidic polymerase targeting sequence

<400> SEQUENCE: 81
auggaagacu uugugcgcac a                                            21

<210> SEQ ID NO 82
<211> LENGTH: 21
<212> TYPE: RNA
<213> ORGANISM: artificial sequence
<220> FEATURE:
<223> OTHER INFORMATION: H5N1 acidic polymerase targeting sequence

<400> SEQUENCE: 82
auggaagacu uugugcgcac a                                            21

<210> SEQ ID NO 83
<211> LENGTH: 21
<212> TYPE: RNA
<213> ORGANISM: artificial sequence
<220> FEATURE:
<223> OTHER INFORMATION: H1N1 acidic polymerase targeting sequence

<400> SEQUENCE: 83
auggaagacu uugugcgcac a                                            21

<210> SEQ ID NO 84
<211> LENGTH: 21
<212> TYPE: RNA
<213> ORGANISM: artificial sequence
<220> FEATURE:
<223> OTHER INFORMATION: H5N1 acidic polymerase targeting sequence

<400> SEQUENCE: 84
auggaagacu uugugcgcac a                                            21

<210> SEQ ID NO 85
<211> LENGTH: 21
<212> TYPE: RNA
<213> ORGANISM: artificial sequence
<220> FEATURE:
```

```
<223> OTHER INFORMATION: H1N1 acidic polymerase targeting sequence

<400> SEQUENCE: 85
gcgacaaugc uucaauccaa u                                              21

<210> SEQ ID NO 86
<211> LENGTH: 21
<212> TYPE: RNA
<213> ORGANISM: artificial sequence
<220> FEATURE:
<223> OTHER INFORMATION: H5N1 acidic polymerase targeting sequence

<400> SEQUENCE: 86
gcgacaaugc uucaauccaa u                                              21

<210> SEQ ID NO 87
<211> LENGTH: 21
<212> TYPE: RNA
<213> ORGANISM: artificial sequence
<220> FEATURE:
<223> OTHER INFORMATION: H1N1 acidic polymerase targeting sequence

<400> SEQUENCE: 87
gcuucaaucc aaugaucguc g                                              21

<210> SEQ ID NO 88
<211> LENGTH: 21
<212> TYPE: RNA
<213> ORGANISM: artificial sequence
<220> FEATURE:
<223> OTHER INFORMATION: H5N1 acidic polymerase targeting sequence

<400> SEQUENCE: 88
gcuucaaucc aaugauuguc g                                              21

<210> SEQ ID NO 89
<211> LENGTH: 21
<212> TYPE: RNA
<213> ORGANISM: artificial sequence
<220> FEATURE:
<223> OTHER INFORMATION: H1N1 non-structural protein targeting sequence

<400> SEQUENCE: 89
gucaagcuuu cagguagacu g                                              21

<210> SEQ ID NO 90
<211> LENGTH: 21
<212> TYPE: RNA
<213> ORGANISM: artificial sequence
<220> FEATURE:
<223> OTHER INFORMATION: H5N1 non-structural protein targeting sequence

<400> SEQUENCE: 90
gucaagcuuu cagguagacu g                                              21

<210> SEQ ID NO 91
<211> LENGTH: 21
<212> TYPE: RNA
<213> ORGANISM: artificial sequence
<220> FEATURE:
<223> OTHER INFORMATION: H1N1 non-structural protein targeting sequence

<400> SEQUENCE: 91
gguagacugu uuccuuuggc a                                              21

<210> SEQ ID NO 92
```

```
<211> LENGTH: 21
<212> TYPE: RNA
<213> ORGANISM: artificial sequence
<220> FEATURE:
<223> OTHER INFORMATION: H5N1 non-structural protein targeting sequence

<400> SEQUENCE: 92
gguagacugc uuucuuuggc a                                              21

<210> SEQ ID NO 93
<211> LENGTH: 23
<212> TYPE: RNA
<213> ORGANISM: artificial sequence
<220> FEATURE:
<223> OTHER INFORMATION: influenza elongation factor EF-1 targeting
      sequence

<400> SEQUENCE: 93
auggaaagaa uaaaagaacu aag                                            23

<210> SEQ ID NO 94
<211> LENGTH: 43
<212> TYPE: DNA
<213> ORGANISM: artificial sequence
<220> FEATURE:
<223> OTHER INFORMATION: primer

<400> SEQUENCE: 94
taatacgact cactatagct gcagagcaag cagactctaa atc                      43

<210> SEQ ID NO 95
<211> LENGTH: 37
<212> TYPE: DNA
<213> ORGANISM: artificial sequence
<220> FEATURE:
<223> OTHER INFORMATION: primer

<400> SEQUENCE: 95
aagctttaaa aatggtgggt ggcgaaggat tcgaacc                             37

<210> SEQ ID NO 96
<211> LENGTH: 43
<212> TYPE: DNA
<213> ORGANISM: artificial sequence
<220> FEATURE:
<223> OTHER INFORMATION: primer

<400> SEQUENCE: 96
taatacgact cactatagct gcagcctgag cagactctaa atc                      43

<210> SEQ ID NO 97
<211> LENGTH: 37
<212> TYPE: DNA
<213> ORGANISM: artificial sequence
<220> FEATURE:
<223> OTHER INFORMATION: primer

<400> SEQUENCE: 97
aagctttaaa aatggtgtcc tgcgaaggat tcgaacc                             37

<210> SEQ ID NO 98
<211> LENGTH: 92
<212> TYPE: RNA
<213> ORGANISM: artificial sequence
<220> FEATURE:
<223> OTHER INFORMATION: sequence of endogenous human tyrosine tRNA
      precursor RNA
<220> FEATURE:
```

```
<221> NAME/KEY: misc_feature
<222> LOCATION: (1)..(3)
<223> OTHER INFORMATION: n is any base

<400> SEQUENCE: 98
nnnguggugg gguucccgag cggccaaagg gagcagacuc uaaaucugcc gucaucgacu      60
ucgaagguuc gaauccuucc cccaccacac ca                                   92

<210> SEQ ID NO 99
<211> LENGTH: 22
<212> TYPE: RNA
<213> ORGANISM: artificial sequence
<220> FEATURE:
<223> OTHER INFORMATION: target mRNA containing consensus GNNNNNNU
<220> FEATURE:
<221> NAME/KEY: misc_feature
<222> LOCATION: (1)..(22)
<223> OTHER INFORMATION: n is any base

<400> SEQUENCE: 99
nnnngnnnnn nunnnnnnnn nn                                              22

<210> SEQ ID NO 100
<211> LENGTH: 59
<212> TYPE: RNA
<213> ORGANISM: artificial sequence
<220> FEATURE:
<223> OTHER INFORMATION: external guide sequence
<220> FEATURE:
<221> NAME/KEY: misc_feature
<222> LOCATION: (1)..(59)
<223> OTHER INFORMATION: n is any base

<400> SEQUENCE: 100
nnnnagcaga cucuaaaucu gccgucaucg acuucgaagg uucgaauccu ucnnnnnnc      59

<210> SEQ ID NO 101
<211> LENGTH: 199
<212> TYPE: RNA
<213> ORGANISM: artificial sequence
<220> FEATURE:
<223> OTHER INFORMATION: human IL-4 receptor alpha chain mRNA

<400> SEQUENCE: 101
agaucaggag uucgagacca gccuggugcc uuggcaucuc ccaauggggu ggcuuugcuc      60
ugggcuccug uucccuguga gcugccuggu ccugcugcag guggcaagcu cugggaacau     120
gaaggucuug caggagccca ccugcgucuc cgacuacaug agcaucucua cuugcgagug     180
gaagaugaau uggucccac                                                  199

<210> SEQ ID NO 102
<211> LENGTH: 59
<212> TYPE: RNA
<213> ORGANISM: artificial sequence
<220> FEATURE:
<223> OTHER INFORMATION: IL-4 receptor alpha EGS

<400> SEQUENCE: 102
cccaccgcuu ccuaagcuug gaagcuucag cuacugccgu cuaaaucuca gacgaacga      59

<210> SEQ ID NO 103
<211> LENGTH: 13
<212> TYPE: RNA
<213> ORGANISM: human

<400> SEQUENCE: 103
```

```
ggguggcuuu gcu                                                    13

<210> SEQ ID NO 104
<211> LENGTH: 19
<212> TYPE: DNA
<213> ORGANISM: artificial sequence
<220> FEATURE:
<223> OTHER INFORMATION: primer

<400> SEQUENCE: 104
agatcaggag ttcgagacc                                              19

<210> SEQ ID NO 105
<211> LENGTH: 21
<212> TYPE: DNA
<213> ORGANISM: artificial sequence
<220> FEATURE:
<223> OTHER INFORMATION: primer

<400> SEQUENCE: 105
gttttcactc caaatgttga c                                           21
```